United States Patent
Kalla et al.

(10) Patent No.: US 9,416,128 B2
(45) Date of Patent: Aug. 16, 2016

(54) FUSED HETEROCYCLIC COMPOUNDS AS ION CHANNEL MODULATORS

(71) Applicant: Gilead Sciences, Inc., Foster City, CA (US)

(72) Inventors: Rao Kalla, Cupertino, CA (US); Thao Perry, San Jose, CA (US); Jeff Zablocki, Los Altos, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 14/573,854

(22) Filed: Dec. 17, 2014

(65) Prior Publication Data

US 2015/0175595 A1    Jun. 25, 2015

Related U.S. Application Data

(60) Provisional application No. 61/918,247, filed on Dec. 19, 2013.

(51) Int. Cl.
*C07D 413/06* (2006.01)
*C07D 417/06* (2006.01)

(52) U.S. Cl.
CPC ............ *C07D 417/06* (2013.01); *C07D 413/06* (2013.01)

(58) Field of Classification Search
CPC .................... C07D 417/06; C07D 413/06
USPC ................ 544/89, 97; 514/230.5, 229.5
See application file for complete search history.

(56) References Cited

U.S. PATENT DOCUMENTS 9,199,988 B2 * 12/2015 Smethurst ............ C07D 413/04
2010/0113514 A1  5/2010 Abelman et al.

FOREIGN PATENT DOCUMENTS

WO    WO-2012154760 A1    11/2012
WO    WO-2013/006485 A1    1/2013

OTHER PUBLICATIONS

Search Report and Written Opinion for PCT/US2014/070920 dated Feb. 9, 2015.

* cited by examiner

*Primary Examiner* — Kahsay Habte
(74) *Attorney, Agent, or Firm* — Francis O. Ginah

(57) ABSTRACT

The present disclosure relates to compounds that are sodium channel inhibitors and to their use in the treatment of various disease states, including cardiovascular diseases and diabetes. In particular embodiments, the structure of the compounds is given by Formula I:

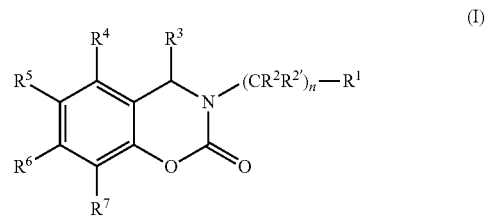

wherein n, $R^1$, $R^2$, $R^{2'}$, $R^3$, $R^4$, $R^5$, $R^6$ and $R^7$ are as described herein, and to methods for the preparation and use of the compounds and to pharmaceutical compositions containing the same.

38 Claims, No Drawings

FUSED HETEROCYCLIC COMPOUNDS AS ION CHANNEL MODULATORS

CROSS-REFERENCE TO RELATED APPLICATIONS

This application claims benefit under 35 U.S.C. §119(e) to U.S. Provisional Application Ser. No. 61/918,247, filed on Dec. 19, 2013, the entirety of which is incorporated herein by reference.

FIELD

The present disclosure relates to novel compounds and to their use in the treatment of diseases including cardiovascular diseases, diabetes, neurological diseases and related diseases. The disclosure also relates to pharmaceutical compositions comprising such compounds.

The late sodium current (INaL) or Late $I_{Na}$ is a sustained component of the fast Na+ current of cardiac myocytes and neurons. Many common neurological and cardiac conditions are associated with abnormal INaL enhancement, which contributes to the pathogenesis of both electrical and contractile dysfunction in mammals, particularly humans. See, for example, Pathophysiology and Pharmacology of the Cardiac "Late Sodium Current", Pharmacology and Therapeutics 119 (2008) 326-339. Accordingly, compounds that selectively inhibit INaL in mammals, particularly humans are useful in treating such disease states. Thus, it is desirable to discover novel compounds that inhibit/block INaL.

SUMMARY

Accordingly, the present disclosure provides novel compounds which are useful as late sodium channel blockers. In one embodiment, the disclosure provides a compound of Formula I:

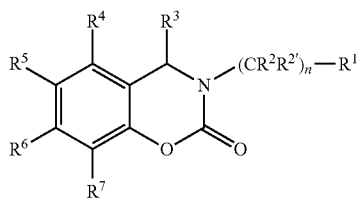

(I)

wherein $R^1$ is a 5 or 6 membered aryl, heteroaryl or heterocyclic group wherein each heteroaryl or heterocyclic group contains from 1 to 3 heteroatoms independently selected from the group consisting of nitrogen, oxygen and sulfur; and wherein the aryl, heteroaryl or heterocyclic group is optionally substituted with 1 or 2 groups independently selected from the group consisting of —$C_1$-$C_6$ alkyl, —$C_3$-$C_6$ cycloalkyl, $C_1$-$C_6$ alkyl$C_3$-$C_6$ cycloalkyl, halogen, —$C_1$-$C_6$ haloalkyl, —$OC_1$-$C_6$ alkyl, —$OC_1$-$C_6$ haloalkyl, and —$C(O)C_1$-$C_6$ alkyl;

$R^2$ and $R^{2'}$ are at each occurrence independently H or —$C_1$-$C_6$ alkyl; or one set of $R^2$ and $R^{2'}$ combine with the carbon atom to which they are both attached to form a $C_3$-$C_6$ cycloalkyl group;

$R^3$ is H, —$C_1$-$C_6$ alkyl or $C_3$-$C_6$ cycloalkyl, $R^4$ is H, —$C_1$-$C_6$ alkyl, —$OC_1$-$C_6$ alkyl, —$OC_1$-$C_6$haloalkyl, —$C_3$-$C_6$ cycloalkyl, or halo;

$R^5$ is a 5 or 6 membered aryl, heteroaryl or heterocyclic group optionally substituted with one, two or three groups independently selected from the group consisting of —$C_1$-$C_6$ alkyl, —$C_2$-$C_6$ alkenyl, —$C_2$-$C_6$ alkynyl, $C_3$-$C_6$ cycloalkyl, $C_1$-$C_6$ alkyl$C_3$-$C_6$ cycloalkyl, —$C_1$-$C_6$haloalkyl, —$OC_1$-$C_6$ alkyl, —$OC_1$-$C_6$ haloalkyl, —O-aryl, and halo; wherein the cycloalkyl group is optionally substituted with —$C_1$-$C_6$ alkyl or —$C_1$-$C_6$ haloalkyl; and wherein the substituent —O-aryl group is optionally substituted with —$C_1$-$C_6$ alkyl, halo, $C_1$-$C_6$ haloalkyl, —$OC_1$-$C_6$ alkyl, or —$OC_1$-$C_6$ haloalkyl; and wherein two substituents on the aryl, heteroaryl, or heterocyclic ring of $R^5$ optionally combine to form a 8-12 membered bicyclic ring optionally containing one or two oxygen atoms; and wherein the bicyclic ring is optionally substituted with 1 or 2 groups independently selected from the group consisting of —$C_1$-$C_6$ alkyl, —$C_1$-$C_6$ haloalkyl, —$OC_1$-$C_6$ alkyl, —$OC_1$-$C_6$ haloalkyl, —$C_3$-$C_6$ cycloalkyl, and halo;

$R^6$ is H, —$C_1$-$C_6$ alkyl, —$C_1$-$C_6$ haloalkyl, —$OC_1$-$C_6$ alkyl, —$OC_1$-$C_6$ haloalkyl, or halo; or $R^6$ combines with the aryl, heteroaryl or heterocyclic ring of $R^5$ to form a tetracyclic ring optionally substituted with 1 or 2 groups independently selected from $C_1$-$C_6$ alkyl, —$C_1$-$C_6$ haloalkyl, —$OC_1$-$C_6$ alkyl, —$OC_1$-$C_6$ haloalkyl, —$C_3$-$C_6$ cycloalkyl, and halo;

$R^7$ is H, —$C_1$-$C_6$ alkyl, —$C_1$-$C_6$ haloalkyl, —$OC_1$-$C_6$ alkyl, —$C_1$-$C_6$ haloalkyl, or halo;

n=1-4;

or a pharmaceutically acceptable salt thereof.

Some embodiments of the present disclosure provide a method of using the compounds of Formula I described herein, in the treatment of a disease or condition in a mammal, particularly a human that is amenable to treatment by a late sodium channel blocker. Such diseases include cardiovascular diseases such as atrial arrhythmias (e.g. atrial fibrillation), ventricular arrhythmias (e.g. ventricular tachycardia or ventricular fibrillation), heart failure (e.g. congestive heart failure, diastolic heart failure, systolic heart failure, or acute heart failure), Prinzmetal's (variant) angina, stable angina, unstable angina, exercise induced angina, congestive heart disease, ischemia, recurrent ischemia, reperfusion injury, myocardial infarction, acute coronary syndrome, Long QT syndromes (LQT1, LQT2, LQT3, LQT4 or LQT5), hypertrophic cardiomyopathy (HCM), peripheral arterial disease and inteimittent claudication. Such diseases may also include diabetes and conditions related to diabetes, e.g. diabetic peripheral neuropathy. Such diseases may also include conditions affecting the neuromuscular system resulting in pain, seizures or paralysis. Therefore, it is contemplated that the compounds of the disclosure and their pharmaceutically acceptable salt, ester, stereoisomer, mixture of stereoisomers and/or tautomer forms are potentially useful as medicaments for the treatment of the aforementioned diseases.

In certain embodiments, the disclosure provides pharmaceutical compositions comprising a therapeutically effective amount of a compound of the disclosure (e.g. a compound of Formula I or additional embodiments described herein, and at least one pharmaceutically acceptable excipient.

DETAILED DESCRIPTION

1. Definitions and General Parameters

As used in the present specification, the following words and phrases are generally intended to have the meanings as set forth below, except to the extent that the context in which they are used indicates otherwise.

The term "alkyl" refers to a mono radical branched or unbranched saturated hydrocarbon chain having (unless otherwise specified) from 1 to 12 carbon atoms, or from 1 to 6 carbon atoms, or from 1 to 4 carbon atoms, or from 1 to 3 carbon atoms or as specified. For example, the term $C_1$-$C_6$ alkyl denotes alkyl groups having from 1 to six carbon atoms including straight and branched chain groups. Similarly, the term $C_0$-$C_6$ alkyl or as indicated denotes a bond ($C_0$) or alkyl groups having from 1 to six carbon atoms including straight and branched chain groups, Thus alkyl groups are exemplified by groups such as methyl, ethyl, n-propyl, iso-propyl, n-butyl, iso-butyl, t-butyl, n-hexyl, n-decyl, dodecyl, and the like.

The term "optionally substituted alkyl" refers to an alkyl group as defined above, lacking a substituent or having 1, 2, 3, 4 or 5 substituents, (in some embodiments, 1, 2 or 3 substituents) or as indicated, selected from the groups indicated such as alkenyl, alkynyl, alkoxy, cycloalkyl, cycloalkenyl, cycloalkoxy, or groups as disclosed herein.

The term "alkylene" refers to a diradical of a branched or unbranched saturated hydrocarbon chain, in some embodiments, having from 1 to 12 carbon atoms (e.g. 1-10 carbon atoms or 1, 2, 3, 4, 5 or 6 carbon atoms). This term is exemplified by groups such as methylene (—$CH_2$—), ethylene (—$CH_2CH_2$—), the propylene isomers (e.g., —$CH_2CH_2CH_2$— and —$CH(CH_3)CH_2$—), and the like. As used herein, an alkyl radical further substituted with more than one substituent is to be treated as an alkylene radical. Thus, an optionally substituted alkyl radical when substituted is equivalent to an alkylene group.

The term "set of $R^2$ and $R^{2'}$" refers to the particular $R^2$ and $R^{2'}$ attached to a particular carbon atom in the chain —$(CR^2R^{2'})_n$—, where n is an integer as defined herein. Thus, one set of $R^2$ and $R^{2'}$ cyclizing to form a cycloalkyl group with the carbon atom to which they are both attached will produce only one cycloalkyl group.

The term "optionally substituted alkylene" refers to an alkylene group as defined above that is unsubstituted or further substituted with 1 to 5 substituents (in some embodiments, 1, 2 or 3 substituents) as defined for substituted alkyl.

The term "aralkyl" or "arylalkyl" refers to an aryl group covalently linked to an alkyl or alkylene group, where aryl, alkyl and alkylene are as defined herein. "Optionally substituted aralkyl" refers to an optionally substituted aryl group covalently linked to an optionally substituted alkyl or alkylene group. Such aralkyl groups are exemplified by benzyl, phenylethyl, 3-(4-methoxyphenyl)propyl, and the like. Similarly, the term "alkylaryl" refers to an alkyl or alkylene group covalently bonded to an aryl group (reading from left to right). "Optionally substituted alkylaryl" refers to an optionally substituted alkyl or alkylene group covalently linked to an optionally substituted aryl group. Such alkylaryl groups are exemplified by methylphenyl, methylenephenyl, and the like.

The term "—O-aryl" refers to an aryl group covalently attached to a named or defined anchor or core group via an oxygen linker.

The term "hydroxy" or "hydroxyl" refers to a group —OH.

The terms "—O—($C_1$-$C_n$)alkyl" and "($C_{1-n}$)alkoxy" are used interchangeably herein, wherein n is an integer, either alone or in combination with another radical. Either term is intended to mean an oxygen atom further bonded to an alkyl radical having 1 to n carbon atoms as defined above. Examples of —O—($C_1$-$C_n$)alkyl include but are not limited to methoxy (—$OCH_3$), ethoxy (—$OCH_2CH_3$), propoxy (—$OCH_2CH_3CH_3$), 1-methylethoxy (iso-propoxy; —$OCH(CH_3)_2$) and 1,1-dimethylethoxy (tert-butoxy; —O—C—($CH_3$)$_3$). When a —O—($C_1$-$C_n$)alkyl radical is substituted, it is understood to be substituted on the ($C_1$-$C_n$)alkyl portion thereof, such that the substitution would give rise to a chemically stable compound, such as are recognized by those skilled in the art. Thus, the term "alkoxy" refers to the group —OR, where R is alkyl and where alkyl including optionally substituted alkyl is as defined herein.

The term "$C_1$-$C_n$ haloalkyl" refers to an alkyl group having from 1 to n carbon atoms and substituted by halogen atoms as indicated or allowed. For example, the term "$C_1$-$C_6$ haloalkyl" refers to an alkyl group having from 1 to 6 carbon atoms covalently bonded to from 1 to 6, or from 1 to 3, halogen(s), where alkyl and halogen are defined herein. In some embodiments, $C_{1-6}$ haloalkyl includes, by way of example, trifluoromethyl, difluoromethyl, fluoromethyl, 2,2,2-trifluoroethyl, 2,2-difluoroethyl, 2-fluoroethyl, 3,3,3-trifluoropropyl, 3,3-difluoropropyl, 3-fluoropropyl. Other haloalkyl groups e.g. $C_1$-$C_3$ haloalkyl follow the same principle except for the length of carbon atoms and the possible number of halogen atoms attached thereto.

The term "$C_3$-$C_n$ cycloalkyl" refers to cyclic alkyl groups of from 3 to the integer n carbon atoms, or as indicated. For example the term "$C_3$-$C_8$ cycloalkyl" has from 3 to 8 carbon atoms having a single cyclic ring. Such cycloalkyl groups include, by way of example, single ring structures such as cyclopropyl, cyclobutyl, cyclopentyl, cyclooctyl and the like.

The term "substituted cycloalkyl" refers to cycloalkyl or cycloalkenyl groups having 1, 2, 3, 4 or 5 substituents (in some embodiments, 1, 2 or 3 substituents), selected from the group consisting of alkyl, alkenyl, alkynyl, alkoxy, cycloalkyl, cycloalkenyl, cycloalkoxy, or as disclosed herein.

The term "bicyclic" refers to fused two-ring structures having saturated or unsaturated carbon atoms and optionally having within the ring one or more heteroatoms selected from oxygen, nitrogen ad sulfur. Bicyclic groups include for example, adamantanyl and bicyclo[2.2.1]heptanyl or cyclic alkyl groups to which is fused an aryl group, such as for example, indanyl and the like, provided that the point of attachment is through the cyclic group. Thus as defined, bicyclic groups may be carbocyclic or heterocyclic and may include fused aryl or fused heteroaryl groups.

The term "aryl" refers to an aromatic carbocyclic group of 6 to 18 carbon atoms having a single ring (e.g., phenyl) or multiple rings (e.g., biphenyl) or multiple condensed (fused) rings (e.g., naphthyl, fluorenyl and anthryl). In some embodiments, aryls include phenyl, fluorenyl, naphthyl, anthryl, and the like.

Unless otherwise constrained by the definition for the aryl substituent, such aryl groups can optionally be substituted with 1, 2, 3, 4 or 5 substituents (in some embodiments, 1, 2 or 3 substituents), as indicated.

The term "aryloxy" refers to the group aryl-O— or —O-aryl, wherein the group is attached via the oxygen atom to the remaining portion (core or anchor) of the molecule and wherein the aryl group is as defined above, and includes optionally substituted aryl groups as also defined above.

The terms "heterocyclyl," "heterocycle," and "heterocyclic" are used synonymously unless otherwise indicated and refer to a monoradical saturated group having a single ring or multiple condensed rings, having (unless otherwise specified) from 3 to 18 carbon atoms and from 1 to 6 hetero atoms, or from 1 to 4 heteroatoms, selected from nitrogen, sulfur, phosphorus, and/or oxygen within the ring. In some embodiments, the heterocyclyl," "heterocycle," or "heterocyclic" group is linked to the remainder of the molecule through one of the heteroatoms within the ring.

Unless otherwise constrained by the definition for the heterocyclic substituent, such heterocyclic groups can be optionally substituted with 1 to 5 substituents (in some embodiments, 1, 2 or 3 substituents), selected from the group consisting of alkyl, alkenyl, alkynyl, alkoxy, cycloalkyl, cycloalkenyl, cycloalkoxy, cycloalkenyloxy, or as described herein.

The term "heteroaryl" refers to a group comprising single or multiple rings comprising 5 to 15 carbon atoms and 1 to 4 heteroatoms selected from oxygen, nitrogen and sulfur within at least one ring. The term "heteroaryl" is generic to the terms "aromatic heteroaryl" and "partially saturated heteroaryl". The term "aromatic heteroaryl" refers to a heteroaryl in which at least one ring is aromatic, regardless of the point of attachment. Examples of aromatic heteroaryls include pyrrole, thiophene, pyridine, quinoline, pteridine.

Unless otherwise constrained by the definition for the heteroaryl substituent, such heteroaryl groups can be optionally substituted with 1 to 5 substituents (in some embodiments, 1, 2 or 3 substituents) as indicated. Such heteroaryl groups can have a single ring (e.g., pyridyl or furyl) or multiple condensed rings (e.g., indolizinyl, benzothiazole or benzothienyl). Examples of nitrogen-containing heterocyclyls and heteroaryls include, but are not limited to, pyrrole, imidazole, pyrazole, pyridine, pyrazine, pyrimidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, and the like as well as N-alkoxynitrogen containing heteroaryl compounds.

The term "amino" refers to the group —NH$_2$.

The term "substituted amino" refers to a group of the type —NRR where each R is independently selected from the group consisting of hydrogen, alkyl, cycloalkyl, aryl, bicyclic, heteroaryl and heterocyclyl or as defined, provided that both R groups are not hydrogen or a group —Y—Z, in which Y is optionally substituted alkylene and Z is alkenyl, cycloalkenyl or alkynyl. Unless otherwise constrained by the definition, all substituents may optionally be further substituted by 1, 2 or 3 substituents as defined or disclosed.

The term "alkyl amine" refers to R—NH$_2$ in which R is optionally substituted alkyl.

The term "dialkyl amine" refers to R—NHR in which each R is independently an optionally substituted alkyl.

The term "trialkyl amine" refers to NR$_3$ in which each R is independently an optionally substituted alkyl.

The term "cyano" refers to the group —CN.

The term "carboxy" refers to a group —C(O)—OH.

The term "ester" or "carboxyester" refers to the group —C(O)OR, where R is alkyl, cycloalkyl, aryl, heteroaryl or heterocyclyl, which may be optionally further substituted by alkyl, alkoxy, halogen, CF$_3$, amino, substituted amino, cyano or —S(O)—R$^a$, in which R$^a$ is alkyl, aryl or heteroaryl and n is 0, 1 or 2.

The term "acyl" denotes the group —C(O)R, in which R is hydrogen, alkyl, cycloalkyl, heterocyclyl, aryl or heteroaryl.

The term "carboxyalkyl" refers to the groups —C(O)O-alkyl or —C(O)O-cycloalkyl, where alkyl and cycloalkyl are as defined herein, and may be optionally further substituted by alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)$_n$R$^a$, in which R$^a$ is alkyl, aryl or heteroaryl and n is 0, 1 or 2.

The term "acyloxy" refers to the group —OC(O)—R, in which R is alkyl, cycloalkyl, heterocyclyl, aryl or heteroaryl. Unless otherwise constrained by the definition, all substituents may optionally be further substituted by 1, 2 or 3 substituents selected from the group consisting of alkyl, alkenyl, alkynyl, carboxy, carboxyalkyl, aminocarbonyl, hydroxy, alkoxy, halogen, CF$_3$, amino, substituted amino, cyano, cycloalkyl, heterocyclyl, aryl, heteroaryl, and —S(O)—R$^a$, in which R$^a$ is alkyl, aryl or heteroaryl and n is 0, 1 or 2.

The term "carbamates" or "carbamic ester" refer to compounds of the general formula R$_2$NCOOR wherein each R is the same or different. A cyclic carbamate is formed when an R group from the amino group is bonded with the ester R group.

The term "halogen" or "halo" refers to fluoro, bromo, chloro and iodo.

Optional" or "optionally" means that the subsequently described event or circumstance may or may not occur, and that the description includes instances where said event or circumstance occurs and instances in which it does not.

A "substituted" group includes embodiments in which a monoradical substituent is bound to a single atom of the substituted group (e.g. forming a branch), and also includes embodiments in which the substituent may be a diradical bridging group bound to two adjacent atoms of the substituted group, thereby forming a fused ring on the substituted group.

Where a given group (moiety) is described herein as being attached to a second group and the site of attachment is not explicit, the given group may be attached at any available site of the given group to any available site of the second group. For example, an "alkyl-substituted phenyl", where the attachment sites are not explicit, may have any available site of the lower alkyl group attached to any available site of the phenyl group. In this regard, an "available site" is a site of the group at which a hydrogen atom of the group may be replaced with a substituent.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. Also not included are infinite numbers of substituents, whether the substituents are the same or different. In such cases, the maximum number of such substituents is three. Each of the above definitions is thus constrained by a limitation that, for example, substituted aryl groups are limited to -substituted aryl-(substituted aryl)-substituted aryl.

A compound of Formula I is intended to encompass the compounds of the disclosure, and the pharmaceutically acceptable salts, pharmaceutically acceptable esters, isomers, tautomers, solvates, isotopes, hydrates, polymorphs, and prodrugs of such compounds unless otherwise specified. Additionally, the compounds of the disclosure may possess one or more asymmetric centers, and may be produced as a racemic mixture or as individual enantiomers or diastereoisomers. The number of stereoisomers present in any given compound of a given formula depends upon the number of asymmetric centers present (there are $2^n$ stereoisomers possible where n is the number of asymmetric centers). The individual stereoisomers may be obtained by resolving a racemic or non-racemic mixture of an intermediate at some appropriate stage of the synthesis or by resolution of the compound by conventional means. The individual stereoisomers (including individual enantiomers and diastereoisomers) as well as racemic and non-racemic mixtures of stereoisomers are encompassed within the scope of the present disclosure, all of which are intended to be depicted by the structures of this specification unless otherwise specifically indicated.

"Isomers" are different compounds that have the same molecular formula. Isomers include stereoisomers, enantiomers and diastereomers.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture. The term "(±)" is used to designate a racemic mixture where appropriate.

"Diastereoisomers" are stereoisomers that have at least two asymmetric atoms, but which are not mirror-images of each other.

The absolute stereochemistry is specified according to the Cahn Ingold Prelog R S system. When the compound is a pure enantiomer the stereochemistry at each chiral carbon may be specified by either R or S. Resolved compounds whose absolute configuration is unknown are designated (+) or (−) depending on the direction (dextro- or laevorotary) that they rotate the plane of polarized light at the wavelength of the sodium D line.

Some of the compounds may exist as tautomeric isomers. Tautomeric isomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

The terms "therapeutically effective amount," and "therapeutically effective dose," are synonymous and refer to an amount of a compound that is sufficient to effect treatment, as defined below, when administered to a mammal, particularly a human, in need of such treatment taken as prescribed or administered by a competent caregiver. The therapeutically effective amount will vary depending upon the subject and disease condition being treated, the weight and age of the subject, the severity of the disease condition, the manner of administration and the like, which can readily be determined by one of ordinary skill in the art.

The term "polymorphs" refers to different crystal structures of a crystalline compound. The different polymorphs may result from differences in crystal packing (packing polymorphism) or differences in packing between different conformers of the same molecule (conformational polymorphism).

The term "prodrug" refers to compounds of Formula I that include chemical groups which, in vivo, can be converted and/or can be split off from the remainder of the molecule to provide for the active drug, a pharmaceutically acceptable salt thereof or a biologically active metabolite thereof.

Deuterium labeled or substituted therapeutic compounds of the disclosure may have improved DMPK (drug metabolism and pharmacokinetic) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a non-isotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

The term "treatment" or "treating" means administration of a compound(s) of the invention, by or at the direction of a competent caregiver, to a mammal, particularly a human, having a disease or in need of said administration for purposes including:
  (i) preventing the disease, that is, causing the clinical symptoms of the disease not to develop;
  (ii) inhibiting the disease, that is, arresting the development of clinical symptoms; and/or
  (iii) relieving the disease, that is, causing the regression of clinical symptoms.

In some cases, the compounds of this disclosure are capable of forming acid and/or base salts.

The term "pharmaceutically acceptable salt" of a given compound refers to salts that retain the biological effectiveness and properties of the given compound, and which are not biologically or otherwise undesirable. Pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, mono, di or tri cycloalkyl amines, mono, di or tri arylamines or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

As used herein, "pharmaceutically acceptable carrier" or "pharmaceutically acceptable excipient" includes any and all acceptable solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

"Coronary diseases" or "cardiovascular diseases" refer to diseases of the cardio vasculature arising from any one or more than one of, for example, heart failure (including congestive heart failure, diastolic heart failure and systolic heart failure), acute heart failure, ischemia, recurrent ischemia, myocardial infarction, arrhythmias, angina (including exercise-induced angina, variant angina, stable angina, unstable angina), acute coronary syndrome, diabetes and intermittent claudication.

"Intermittent claudication" means the pain associated with peripheral artery disease. "Peripheral artery disease" or PAD is a type of occlusive peripheral vascular disease (PVD). PAD affects the arteries outside the heart and brain. The most common symptom of PAD is a painful cramping in the hips, thighs or calves when walking, climbing stairs or exercising. The pain is called intermittent claudication. When listing the symptom intermittent claudication, it is intended to include both PAD and PVD.

Arrhythmia refers to any abnormal heart rate. Bradycardia refers to abnormally slow heart rate whereas tachycardia refers to an abnormally rapid heart rate. As used herein, the treatment of arrhythmia is intended to include the treatment of supra ventricular tachycardias such as atrial fibrillation, atrial flutter, AV nodal reentrant tachycardia, atrial tachycardia, ventricular fibrillation (VF), or the ventricular tachycardia (VT). VT includes idiopathic ventricular tachycardia, pre-excitation syndrome and Torsade de Pointes (TdP).

2. Nomenclature

Names of compounds of the present disclosure are provided using ACD/Name software for naming chemical compounds (Advanced Chemistry Development, Inc., Toronto, Canada). Other compounds or radicals may be named with common names or systematic or non-systematic names. The naming and numbering of the compounds of the disclosure is illustrated with a representative compound of Formula I:

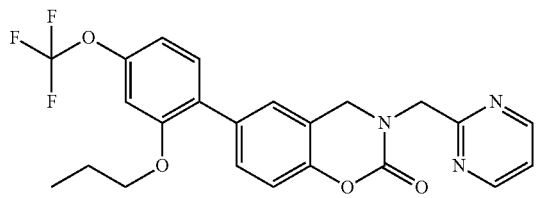 [SMILES: CCCOc1cc(OC(F)(F)F)ccc1-c1ccc2c(c1)CN(Cc1ncccn1)C(=O)O2]

which is named: 6-(2-propoxy-4-(trifluoromethoxy)phenyl)-3-(pyrimidin-2-ylmethyl)-3,4-dihydro-2H-benzo[e][1,3]oxazin-2-one.

3. Compounds

Accordingly, typical embodiments of the present disclosure provide novel compounds that function as late sodium channel blockers. In one embodiment, the disclosure provides compounds of Formula I:

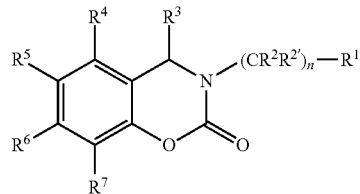

wherein $R^1$ is a 5 or 6 membered aryl, heteroaryl or heterocyclic group wherein each heteroaryl or heterocyclic group contains from 1 to 3 heteroatoms independently selected from the group consisting of nitrogen, oxygen and sulfur; and wherein the aryl, heteroaryl or heterocyclic group is optionally substituted with 1 or 2 groups independently selected from the group consisting of $—C_1$-$C_6$ alkyl, $—C_3$-$C_6$ cycloalkyl, $C_1$-$C_6$ alkyl$C_3$-$C_6$ cycloalkyl, halogen, $—C_1$-$C_6$ haloalkyl, $—OC_1$-$C_6$ alkyl, $—OC_1$-$C_6$ haloalkyl, and $—C(O)C_1$-$C_6$ alkyl;

$R^2$ and $R^{2'}$ are at each occurrence independently H or $—C_1$-$C_6$ alkyl; or one set of $R^2$ and $R^{2'}$ combine with the carbon atom to which they are both attached to form a $C_3$-$C_6$ cycloalkyl group;

$R^3$ is H, $—C_1$-$C_6$ alkyl, or $C_3$-$C_6$ cycloalkyl, $R^4$ is H, $—C_1$-$C_6$ alkyl, $—OC_1$-$C_6$ alkyl, $—OC_1$-$C_6$ haloalkyl, $—C_3$-$C_6$ cycloalkyl, or halo;

$R^5$ is a 5 or 6 membered aryl, heteroaryl or heterocyclic group optionally substituted with one, two or three groups independently selected from the group consisting of $—C_1$-$C_6$ alkyl, $—C_2$-$C_6$ alkenyl, $—C_2$-$C_6$ alkynyl, $C_3$-$C_6$ cycloalkyl, $C_1$-$C_6$ alkyl$C_3$-$C_6$ cycloalkyl, $—C_1$-$C_6$haloalkyl, $—OC_1$-$C_6$ alkyl, $—OC_1$-$C_6$ haloalkyl, $—O$-aryl, and halo; wherein the cycloalkyl group is optionally substituted with $—C_1$-$C_6$ alkyl or $—C_1$-$C_6$ haloalkyl; and wherein the substituent $—O$-aryl group is optionally substituted with $—C_1$-$C_6$ alkyl, halo, $C_1$-$C_6$ haloalkyl, $—OC_1$-$C_6$ alkyl, or $—OC_1$-$C_6$ haloalkyl; and wherein two substituents on the aryl, heteroaryl, or heterocyclic ring of $R^5$ optionally combine to form a 8-12 membered bicyclic ring optionally containing one or two oxygen atoms; and wherein the bicyclic ring is optionally substituted with 1 or 2 groups independently selected from the group consisting of $—C_1$-$C_6$ alkyl, $—C_1$-$C_6$ haloalkyl, $—OC_1$-$C_6$ alkyl, $—OC_1$-$C_6$ haloalkyl, $—C_3$-$C_6$ cycloalkyl, and halo;

$R^6$ is H, $—C_1$-$C_6$ alkyl, $—C_1$-$C_6$ haloalkyl, $—OC_1$-$C_6$ alkyl, $—OC_1$-$C_6$haloalkyl, or halo; or $R^6$ combines with the aryl, heteroaryl or heterocyclic ring of $R^5$ to form a tetracyclic ring optionally substituted with 1 or 2 groups independently selected from $C_1$-$C_6$ alkyl, $—C_1$-$C_6$ haloalkyl, $—OC_1$-$C_6$ alkyl, $—OC_1$-$C_6$ haloalkyl, $—C_3$-$C_6$ cycloalkyl, and halo;

$R^7$ is H, $—C_1$-$C_6$ alkyl, $—C_1$-$C_6$ haloalkyl, $—OC_1$-$C_6$ alkyl, $—C_1$-$C_6$ haloalkyl, or halo;

n=1-4;

or a pharmaceutically acceptable salt thereof.

In yet another embodiment, the disclosure provides compounds of formula (I)

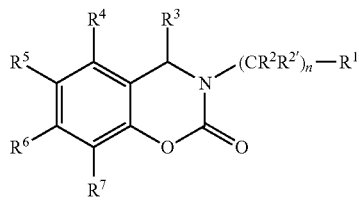

wherein $R^1$ is a pyrimidinyl, pyridinyl, imidazolyl, thiazolyl, oxazolyl, or triazolyl group optionally substituted with 1 or 2 groups independently selected from the group consisting of $C_1$-$C_6$ alkyl, $C_3$-$C_6$ cycloalkyl, halogen, $C_1$-$C_6$ haloalkyl, $C_1$-$C_6$ alkoxy, —$OC_1$-$C_6$ haloalkyl, and —$C(O)C_1$-$C_6$ alkyl;

$R^2$ and $R^{2'}$ are at each occurrence independently H or $C_1$-$C_6$ alkyl; or one set of $R^2$ and $R^{2'}$ combines with the carbon atom to which they are both attached to form a cycloalkyl group having from 3 to 6 carbon atoms;

$R^3$ is H or —$C_1$-$C_6$ alkyl;

$R^4$ is H, —$C_1$-$C_6$ alkyl, or halo;

$R^5$ is a phenyl group substituted with one or two groups independently selected from the group consisting of —$C_1$-$C_6$ alkyl, $C_3$-$C_6$ cycloalkyl, —$C_1$-$C_6$ alkyl$C_3$-$C_6$ cycloalkyl, —$C_1$-$C_6$haloalkyl, —$OC_1$-$C_6$ alkyl, —$OC_1$-$C_6$ haloalkyl, —O-aryl, and halo; wherein the cycloalkyl group is optionally substituted with $C_1$-$C_6$ alkyl or $C_1$-$C_6$ haloalkyl; wherein the substituent —O-aryl group is optionally substituted with $C_1$-$C_6$ alkyl, halo, $C_1$-$C_6$haloalkyl, —$OC_1$-$C_6$ alkyl, or —$OC_1$-$C_6$ haloalkyl; wherein two substituents on the phenyl ring of $R^5$ optionally combine to form a bicyclic ring optionally containing one or two oxygen atoms; and wherein the bicyclic ring is optionally substituted with 1 or 2 groups independently selected from the group consisting of —$C_1$-$C_6$ alkyl and halogen;

$R^6$ is H, —$C_1$-$C_6$ alkyl, —$C_1$-$C_6$haloalkyl, —$OC_1$-$C_6$ alkyl, —$OC_1$-$C_6$haloalkyl, or halo; or $R^6$ combines with the phenyl ring of $R^5$ to form a tetracyclic ring optionally substituted with 1 or 2 groups independently selected from $C_1$-$C_6$ alkyl, —$OC_1$-$C_6$ alkyl, —$OC_1$-$C_6$haloalkyl, —$C_3$-$C_6$ cycloalkyl, and halo;

$R^7$ is H, —$C_1$-$C_6$ alkyl, —$C_1$-$C_6$haloalkyl, —$OC_1$-$C_6$ alkyl, —$C_1$-$C_6$haloalkyl, or halo;

n=1-4;

or a pharmaceutically acceptable salt thereof.

In one embodiment, the present disclosure provides a compound of formula (I)

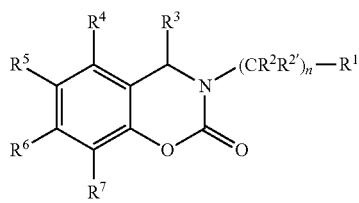

wherein:

$R^1$ is a pyrimidinyl, pyridinyl, imidazolyl, thiazolyl, oxazolyl, or triazolyl group optionally substituted with 1 or 2 groups independently selected from the group consisting of $C_1$-$C_3$ alkyl, and $C_3$-$C_6$ cycloalkyl;

$R^2$ and $R^{2'}$ are at each occurrence independently H or $C_1$-$C_3$ alkyl; or one set of $R^2$ and $R^{2'}$ optionally combine with the carbon atom to which they are both attached to form a cycloalkyl group having from 3 to 6 carbon atoms;

$R^3$ is H or —$C_1$-$C_6$ alkyl;

$R^4$ is H, or —$C_1$-$C_6$ alkyl;

$R^5$ is a phenyl group substituted with one or two groups independently selected from the group consisting of —$C_1$-$C_3$ alkyl, $C_3$-$C_6$ cycloalkyl, —$C_1$-$C_6$ alkyl$C_3$-$C_6$ cycloalkyl, —$C_1$-$C_3$ haloalkyl, —$OC_1$-$C_3$ alkyl, —$OC_1$-$C_3$ haloalkyl, —O-aryl, and halo;

$R^6$ is H, —$C_1$-$C_3$ alkyl, —$C_1$-$C_3$haloalkyl, —$OC_1$-$C_6$ alkyl, —$OC_1$-$C_3$ haloalkyl, or halo; or $R^6$ combines with the phenyl ring of $R^5$ to form a tetracyclic ring optionally substituted with 1 or 2 groups independently selected from $C_1$-$C_6$ alkyl, —$OC_1$-$C_6$alkyl, —$OC_1$-$C_6$haloalkyl, —$C_3$-$C_6$ cycloalkyl, and halo;

$R^7$ is H, —$C_1$-$C_3$ alkyl, —$C_1$-$C_3$haloalkyl, —$OC_1$-$C_3$ alkyl, —$C_1$-$C_3$haloalkyl, or halo;

n=1-2;

or a pharmaceutically acceptable salt thereof.

In yet another embodiment, the disclosure provides a compound of formula (I)

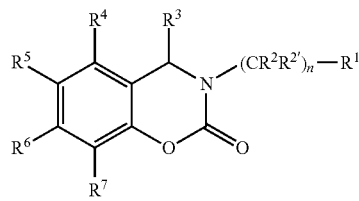

wherein $R^1$ is a pyrimidinyl, pyridinyl, imidazolyl, thiazolyl, oxazolyl, or triazolyl group optionally substituted with 1 or 2 groups independently selected from the group consisting of $C_1$-$C_3$ alkyl, and $C_3$-$C_6$ cycloalkyl;

$R^2$ and $R^{2'}$ are at each occurrence independently H or $C_1$-$C_3$ alkyl; or one set of $R^2$ and $R^{2'}$ optionally combine with the carbon atom to which they are both attached to form a cycloalkyl group having from 3 to 6 carbon atoms;

$R^3$ is H or —$C_1$-$C_6$ alkyl;

$R^4$ is H, or —$C_1$-$C_6$ alkyl;

$R^5$ is a phenyl group substituted with one or two groups independently selected from the group consisting of —$C_1$-$C_3$ alkyl, $C_3$-$C_6$ cycloalkyl, —$C_1$-$C_6$ alkyl$C_3$-$C_6$ cycloalkyl, —$C_1$-$C_3$haloalkyl, —$OC_1$-$C_3$ alkyl, —$OC_1$-$C_3$ haloalkyl, —O-aryl, and halo;

$R^6$ is H, —$C_1$-$C_3$ alkyl, —$C_1$-$C_3$ haloalkyl, —$OC_1$-$C_6$ alkyl, —$OC_1$-$C_3$ haloalkyl, or halo; or $R^6$ combines with the phenyl ring of $R^5$ to form a tetracyclic ring optionally substituted with 1 or 2 groups independently selected from $C_1$-$C_6$ alkyl, —$OC_1$-$C_6$ alkyl, —$OC_1$-$C_6$haloalkyl, —$C_3$-$C_6$ cycloalkyl, and halo;

$R^7$ is H, —$C_1$-$C_3$ alkyl, —$C_1$-$C_3$ haloalkyl, —$OC_1$-$C_3$ alkyl, —$C_1$-$C_3$ haloalkyl, or halo;

n=1-2;

or a pharmaceutically acceptable salt thereof.

In yet another embodiment is provided a compound of formula I

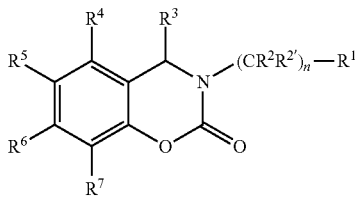

wherein,

R¹ is a pyrimidinyl, pyridinyl, imidazolyl, or thiazolyl group optionally substituted with 1 or 2 groups independently selected from the group consisting of $C_1$-$C_3$ alkyl, $C_3$-$C_6$ cycloalkyl and halo;

$R^2$ and $R^{2'}$ are at each occurrence independently H or $C_1$-$C_3$ alkyl; or one set of $R^2$ and $R^2$ optionally combine with the carbon atom to which they are both attached to form a cyclopropyl group;

$R^3$ is H or —$C_1$-$C_6$ alkyl;

$R^4$ is H;

$R^5$ is a phenyl group substituted with one or two groups independently selected from the group consisting of —$C_1$-$C_3$ alkyl, —$C_1$-$C_3$ haloalkyl, —$OC_1$-$C_3$ alkyl, —$OC_1$-$C_3$ haloalkyl, and halo;

$R^6$ is H, or —$C_1$-$C_3$ alkyl;

$R^7$ is H, or —$C_1$-$C_3$ alkyl;

n=1-2;

or a pharmaceutically acceptable salt thereof.

In one embodiment, $R^1$ is pyridinyl, pyrimidinyl, imidazolyl or thiazolyl. In another embodiment, $R^1$ is pyrimidinyl or pyridinyl. In yet another embodiment, $R^1$ is thiazolyl or imidazolyl. In yet another embodiment, $R^1$ is selected from the group consisting of:

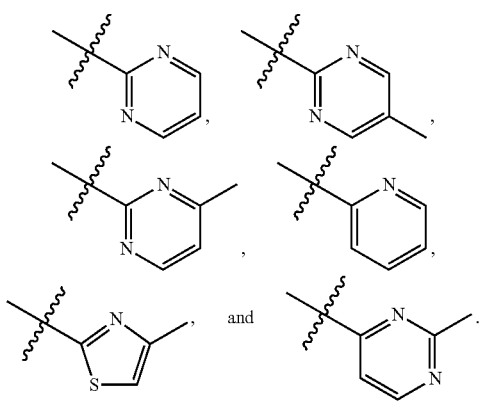

In one embodiment, n is 1, 2 or 3. In another embodiment, n is 1 or 2. In yet another embodiment, n is 1.

In one embodiment $(CR^2R^{2'})_n$ constitutes —$CH_2$—. In another embodiment, $(CR^2R^{2'})_n$ constitutes —$CH_2CH_2$—, or —$CH_2CH_2CH_2$—. In yet another embodiment, $(CR^2R^{2'})_n$ constitutes

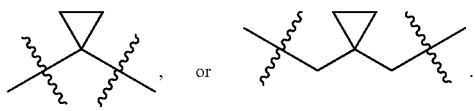 [SMILES: *C1(*)CC1 ; *CC1(C*)CC1]

In one embodiment $R^3$ is H or $C_1$-$C_3$alkyl. In yet another embodiment $R^3$ is H or $CH_3$. In another embodiment, $R^3$ is H.

In one embodiment $R^4$ is H, —$C_1$-$C_3$ alkyl, —$OC_1$-$C_3$ alkyl, —$OC_1$-$C_3$haloalkyl, —$C_3$-$C_6$ cycloalkyl, or halo. In another embodiment, $R^4$ is H, —$C_1$-$C_3$ alkyl, or halo. In yet another embodiment, $R^4$ is H.

In one embodiment, $R^5$ is an aryl group optionally substituted with cycloalkyl, —$C_1$-$C_6$ alkyl$C_3$-$C_6$ cycloalkyl, or —O-aryl; wherein the cycloalkyl group is optionally substituted with $C_1$-$C_6$ alkyl or $C_1$-$C_6$ haloalkyl;

In one embodiment, $R^5$ is an aryl group substituted with two groups independently selected from the group consisting of —$C_1$-$C_3$ alkyl, —$C_1$-$C_3$haloalkyl, —$OC_1$-$C_3$ alkyl, cycloalkyl, —$C_1$-$C_6$ alkyl$C_3$-$C_6$ cycloalkyl, and —$OC_1$-$C_3$ haloalkyl; wherein the cycloalkyl group is optionally substituted with $C_1$-$C_6$ alkyl or $C_1$-$C_6$ haloalkyl; and wherein the two substituents on the aryl optionally combine to form a bicyclic ring optionally containing one or two oxygen atoms; and wherein the bicyclic ring is optionally substituted with 1 or 2 groups independently selected from the group consisting of —$C_1$-$C_6$ alkyl and halogen.

In one embodiment, $R^5$ is a phenyl group substituted with one or two groups independently selected from the group consisting of: —$C_1$-$C_3$ alkyl, $C_3$-$C_6$ cycloalkyl, —$C_1$-$C_3$ alkyl$C_3$-$C_6$ cycloalkyl, —$C_1$-$C_3$ haloalkyl, —$OC_1$-$C_3$ alkyl, —$OC_1$-$C_3$ haloalkyl and halo. In yet another embodiment, $R^5$ is a phenyl group substituted with one or two groups independently selected from the group consisting of —$C_1$-$C_3$ haloalkyl, —$OC_1$-$C_3$ alkyl, —$OC_1$-$C_3$ haloalkyl, and halo.

In yet another embodiment, $R^5$ is phenyl substituted with one or two groups independently selected from chloro, fluoro, methyl, trifluoromethyl, or trifluoromethoxy.

In one embodiment $R^6$ is selected from the group consisting of: H, —$C_1$-$C_3$ alkyl, —$C_1$-$C_6$ haloalkyl, —$OC_1$-$C_6$ alkyl, —$OC_1$-$C_6$ haloalkyl, or halo; or $R^6$ combines with the aryl ring of $R^5$ to form a tetracyclic ring optionally substituted with 1 or 2 groups independently selected from $C_1$-$C_6$ alkyl, —$OC_1$-$C_6$alkyl, —$OC_1$-$C_6$haloalkyl, —$C_3$-$C_6$ cycloalkyl, —COOH, and halo; In one embodiment, $R^6$ is selected from the group consisting of: H, —$C_1$-$C_3$ alkyl, —$C_1$-$C_3$ haloalkyl, —$OC_1$-$C_3$alkyl, —$OC_1$-$C_6$haloalkyl, or halo. In yet another embodiment, $R^6$ is H or $C_1$-$C_3$ alkyl, $C_1$-$C_3$ haloalkyl, or halo. In yet another embodiment, $R^6$ is H or $C_1$-$C_3$ alkyl.

In one embodiment $R^7$ is selected from the group consisting of: H, —$C_1$-$C_3$ alkyl, —$C_1$-$C_3$ haloalkyl, —$OC_1$-$C_3$ alkyl, —$OC_1$-$C_3$ haloalkyl, or halo. In another embodiment, $R^7$ is H, —$C_1$-$C_3$ alkyl, —$C_1$-$C_3$ haloalkyl, or halo. In yet another embodiment, $R^7$ is H or —$C_1$-$C_3$ alkyl or halo.

In one embodiment, the disclosure provides a compound according of formula (I) wherein:

$R^1$ is a pyridine, pyrimidine, imidazolyl, or thiazolyl group each optionally substituted with 1 or 2 groups independently selected from the group consisting of $C_1$-$C_6$ alkyl, $C_3$-$C_6$ cycloalkyl, halogen, $C_1$-$C_6$ haloalkyl, —$OC_1$-$C_6$ alkyl, —$OC_1$-$C_6$ haloalkyl, and —$C(O)C_1$-$C_6$ alkyl;

$R^2$ and $R^{2'}$ are at each occurrence independently H or $C_1$-$C_6$ alkyl; or one set of $R^2$ and $R^2$ combine with the carbon atom to which they are both attached to form a $C_3$-$C_6$ cycloalkyl group;

$R^3$ is H or —$C_1$-$C_6$ alkyl;

$R^4$ is H, or —$C_1$-$C_6$ alkyl;

$R^5$ is a phenyl group substituted with one or two groups independently selected from the group consisting of —$C_1$-$C_6$ alkyl, $C_3$-$C_6$ cycloalkyl, —$C_1$-$C_6$ alkyl$C_3$-$C_6$ cycloalkyl, —$C_1$-$C_6$haloalkyl, —$OC_1$-$C_6$ alkyl, —$OC_1$-$C_6$ haloalkyl, —O-aryl, and halo; wherein the cycloalkyl group is optionally substituted with $C_1$-$C_6$ alkyl or $C_1$-$C_6$ haloalkyl; wherein the substituent —O-aryl group is optionally substituted with $C_1$-$C_6$ alkyl, halo, $C_1$-$C_6$ haloalkyl, —$OC_1$-$C_6$ alkyl, or —$OC_1$-$C_6$ haloalkyl; wherein two substituents on the phenyl ring of $R^5$ optionally combine to form a bicyclic ring optionally containing one or two oxygen atoms; and wherein the bicyclic ring is optionally substituted with 1 or 2 groups independently selected from the group consisting of —$C_1$-$C_6$ alkyl and halogen;

$R^6$ is H, —$C_1$-$C_6$ alkyl, —$C_1$-$C_6$haloalkyl, —$OC_1$-$C_6$ alkyl, —$OC_1$-$C_6$ haloalkyl, or halo; or $R^6$ combines with the phenyl ring of $R^5$ to form a tetracyclic ring optionally substituted with 1 or 2 groups independently selected from $C_1$-$C_6$ alkyl, —$OC_1$-$C_6$ alkyl, —$OC_1$-$C_6$ haloalkyl, —$C_3$-$C_6$ cycloalkyl, and halo;

$R^7$ is H, —$C_1$-$C_6$ alkyl, —$C_1$-$C_6$ haloalkyl, —$OC_1$-$C_6$ alkyl, —$C_1$-$C_6$ haloalkyl, or halo;

n=1-2; or a pharmaceutically acceptable salt thereof.

In one embodiment, the disclosure provides a compound of formula (I) wherein, $R^1$ is a pyrimidinyl, pyridinyl, imidazolyl, thiazolyl, oxazolyl, or triazolyl group optionally substituted with 1 or 2 groups independently selected from the group consisting of $C_1$-$C_3$ alkyl, and $C_3$-$C_6$ cycloalkyl;

$R^2$ and $R^{2'}$ are at each occurrence independently H or $C_1$-$C_3$ alkyl; or one set of $R^2$ and $R^2$ optionally combine with the carbon atom to which they are both attached to form a $C_3$-$C_6$ cycloalkyl group;

$R^3$ is H or —$C_1$-$C_6$ alkyl;

$R^4$ is H, or —$C_1$-$C_6$ alkyl;

$R^5$ is a phenyl group substituted with one or two groups independently selected from the group consisting of —$C_1$-$C_3$ alkyl, $C_3$-$C_6$ cycloalkyl, —$C_1$-$C_6$ alkyl$C_3$-$C_6$ cycloalkyl, —$C_1$-$C_3$ haloalkyl, —$OC_1$-$C_3$ alkyl, —$OC_1$-$C_3$ haloalkyl, —O-aryl, and halo;

$R^6$ is H, —$C_1$-$C_3$ alkyl, —$C_1$-$C_3$ haloalkyl, —$OC_1$-$C_6$ alkyl, —$OC_1$-$C_3$ haloalkyl, or halo; or $R^6$ combines with the phenyl ring of $R^5$ to form a tetracyclic ring optionally substituted with 1 or 2 groups independently selected from $C_1$-$C_6$ alkyl, —$OC_1$-$C_6$ alkyl, —$OC_1$-$C_6$ haloalkyl, —$C_3$-$C_6$ cycloalkyl, and halo;

$R^7$ is H, —$C_1$-$C_3$ alkyl, —$C_1$-$C_3$ haloalkyl, —$OC_1$-$C_3$ alkyl, —$C_1$-$C_3$ haloalkyl, or halo;

n=1-4; or a pharmaceutically acceptable salt thereof.

In one embodiment, the disclosure provides a compound of formula (I) wherein, $R^1$ is a pyrimidinyl, pyridinyl, imidazolyl, thiazolyl, oxazolyl, or triazolyl group optionally substituted with 1 or 2 groups independently selected from the group consisting of $C_1$-$C_3$ alkyl, and $C_3$-$C_6$ cycloalkyl;

$R^2$ and $R^{2'}$ are at each occurrence independently H or $C_1$-$C_3$ alkyl; or one set of $R^2$ and $R^2$ optionally combine with the carbon atom to which they are both attached to form a $C_3$-$C_6$ cycloalkyl group;

$R^3$ is H or —$C_1$-$C_6$ alkyl;

$R^4$ is H, or —$C_1$-$C_6$ alkyl;

$R^5$ is a phenyl group substituted with one or two groups independently selected from the group consisting of —$C_1$-$C_3$ alkyl, $C_3$-$C_6$ cycloalkyl, —$C_1$-$C_6$ alkyl$C_3$-$C_6$ cycloalkyl, —$C_1$-$C_3$ haloalkyl, —$OC_1$-$C_3$ alkyl, —$OC_1$-$C_3$ haloalkyl, —O-aryl, and halo;

$R^6$ is H, —$C_1$-$C_3$ alkyl, —$C_1$-$C_3$ haloalkyl, —$OC_1$-$C_6$ alkyl, —$OC_1$-$C_3$ haloalkyl, or halo; or $R^6$ combines with the phenyl ring of $R^5$ to form a tetracyclic ring optionally substituted with 1 or 2 groups independently selected from $C_1$-$C_6$ alkyl, —$OC_1$-$C_6$ alkyl, —$OC_1$-$C_6$haloalkyl, —$C_3$-$C_6$ cycloalkyl, and halo;

$R^7$ is H, —$C_1$-$C_3$ alkyl, —$C_1$-$C_3$ haloalkyl, —$OC_1$-$C_3$ alkyl, —$C_1$-$C_3$ haloalkyl, or halo;

n=1-2; or a pharmaceutically acceptable salt thereof.

In one embodiment the disclosure provides a compound of formula (I) wherein:

$R^1$ is a pyridine, pyrimidine, imidazolyl, or thiazolyl group each optionally substituted with 1 or 2 groups independently selected from the group consisting of $C_1$-$C_6$ alkyl, $C_3$-$C_6$ cycloalkyl, halogen, $C_1$-$C_6$ haloalkyl, —$OC_1$-$C_6$ alkyl, —$OC_1$-$C_6$ haloalkyl, and —C(O)$C_1$-$C_6$ alkyl;

$R^2$ and $R^{2'}$ are at each occurrence independently H or $C_1$-$C_6$ alkyl; or one set of $R^2$ and $R^2$ combine with the carbon atom to which they are both attached to form a $C_3$-$C_6$ cycloalkyl group;

$R^3$ is H or —$C_1$-$C_6$ alkyl;

$R^4$ is H, or —$C_1$-$C_6$ alkyl;

$R^5$ is phenyl optionally substituted with one, two or three groups independently selected from the group consisting of —$C_1$-$C_6$ alkyl, —$C_0$-$C_6$ alkyl$C_3$-$C_6$ cycloalkyl, —$C_1$-$C_6$ haloalkyl, —$OC_1$-$C_6$ alkyl, —$OC_1$-$C_6$ haloalkyl, —O-aryl, and halo; wherein the cycloalkyl group is optionally substituted with —$C_1$-$C_6$ alkyl or —$C_1$-$C_6$ haloalkyl; and n is 1 or 2; or a pharmaceutically acceptable salt thereof.

In one embodiment, the disclosure provides a compound of formula (I) wherein:

$R^1$ is a 5-membered heterocyclic group;

one set of $R^2$ and $R^{2'}$ combine to form a cyclopropyl group;

$R^3$ and $R^4$ are each H;

$R^5$ is a phenyl group optionally substituted with one or two groups independently selected from $C_1$-$C_3$ alkyl, —$C_1$-$C_3$ haloalkyl, —$OC_1$-$C_3$ alkyl, —$OC_1$-$C_3$ haloalkyl, and halo;

$R^6$ and $R^7$ are both H; and n is 3; or a pharmaceutically acceptable salt thereof.

In one embodiment, the disclosure provides a compound of formula (I) wherein:

$R^1$ is a 5-membered heterocyclic group;

One set of $R^2$ and $R^{2'}$ combine to form a cyclopropyl group;

$R^3$ and $R^4$ are each H;

$R^5$ is a phenyl group optionally substituted with one or two groups independently selected from $C_1$-$C_3$ alkyl, —$C_1$-$C_3$ haloalkyl, —$OC_1$-$C_3$ alkyl, —$OC_1$-$C_3$ haloalkyl, and halo;

$R^6$ and $R^7$ are both H; and n is 2; or a pharmaceutically acceptable salt thereof.

In one embodiment, the disclosure provides a compound of formula (I) wherein:

$R^1$ is a 5-membered heterocyclic group;

One set of $R^2$ and $R^{2'}$ combine to form a cyclopropyl group;

$R^3$ and $R^4$ are each H;

$R^5$ is a phenyl group optionally substituted with one or two groups independently selected from $C_1$-$C_3$ alkyl, —$C_1$-$C_3$haloalkyl, —$OC_1$-$C_3$ alkyl, —$OC_1$-$C_3$ haloalkyl, and halo;

$R^6$ and $R^7$ are both H; and n is 1; or a pharmaceutically acceptable salt thereof In one embodiment the disclosure provides a compound of formula (I) wherein:

$R^1$ is a 6-membered heterocyclic $R^2$ and $R^{2'}$ are both H;

$R^3$ is H or $C_1$-$C_6$ alkyl;

$R^4$ is H or $C_1$-$C_6$ alkyl;

R⁵ is a phenyl group optionally substituted with one or two groups independently selected from $C_1$-$C_3$ alkyl, —$C_1$-$C_3$ haloalkyl, —$OC_1$-$C_3$ alkyl, —$OC_1$-$C_3$ haloalkyl, and halo R⁶ and R⁷ are both H; and n is 1; or a pharmaceutically acceptable salt thereof In one embodiment, the disclosure provides a compound of formula (I) wherein:

R¹ is a pyrimidinyl optionally substituted with $C_1$-$C_6$ alkyl;
R² and R²' are both H;
R³ is $CH_3$;
R⁴ is H;
R⁵ is a phenyl group optionally substituted with one or two groups independently selected from —$OCF_3$, halogen, $CH_3$, or —$OCH_3$;
R⁶ and R⁷ are both H; and
n is 1; or a pharmaceutically acceptable salt thereof.

One embodiment of the disclosure provides a compound of formula (I) wherein:

R¹ is a pyrimidinyl optionally substituted with $C_1$-$C_6$ alkyl;
R² and R²' are both H;
R³ is H;
R⁴ is H;
R⁵ is a phenyl group optionally substituted with one or two groups independently selected from —$OCF_3$, halogen, $CH_3$, or —$OCH_3$;
R⁶ and R⁷ are both H; and
n is 1 or a pharmaceutically acceptable salt thereof.

In one embodiment, the disclosure provides a compound of formula (I) wherein:

R¹ is thiazolyl optionally substituted with $C_1$-$C_6$ alkyl;
R² and R²' are both H;
R³ is H;
R⁴ is H;
R⁵ is a phenyl group optionally substituted with one or two groups independently selected from $CH_3$, —$OCF_3$, halogen, or —$OCH_3$;
R⁶ and R⁷ are both H; and
n is 1; or a pharmaceutically acceptable salt thereof.

In one embodiment, the disclosure provides a compound of formula (I) wherein:

R¹ is pyridinyl optionally substituted with $C_1$-$C_6$ alkyl;
R² and R²' are both H;
R³ is H;
R⁴ is H;
R⁵ is a phenyl group optionally substituted with one or two groups independently selected from $CH_3$, —$OCF_3$, halogen, or —$OCH_3$;
R⁶ and R⁷ are both H; and
n is 1; or a pharmaceutically acceptable salt thereof.

Compounds of the present disclosure include compounds comprising combination of embodiments of R¹, R², R²', R³, R⁴, R⁵, R⁶ and R⁷ as disclosed herein such that each combination of variables R¹-R⁷ represents an embodiment of a compound of the disclosure useful as disclosed herein.

In another embodiment, the present disclosure provides a compound or combination compounds disclosed herein for use in the manufacture of a medicament for treating a disease selected from diabetes, diabetic retinopathy, kidney disease, atrial arrhythmias, ventricular arrhythmias, heart failure, congestive heart failure, diastolic heart failure, systolic heart failure, acute heart failure, Prinzmetal's (variant) angina, stable angina, unstable angina, exercise induced angina, congestive heart disease, ischemia, recurrent ischemia, reperfusion injury, myocardial infarction, acute coronary syndrome, peripheral arterial disease, LQT syndrome, hypertrophic cardiomyopathy, pulmonary hypertension and intermittent claudication.

In another embodiment, the present disclosure provides for the use of a compound of Formula (I) in therapy.

In another embodiment, the present disclosure provides a compound or combination compounds disclosed herein for use in the manufacture of a medicament for treating a disease selected from diabetes, diabetic retinopathy, kidney disease, atrial arrhythmias, ventricular arrhythmias, heart failure, congestive heart failure, diastolic heart failure, systolic heart failure, acute heart failure, Prinzmetal's (variant) angina, stable angina, unstable angina, exercise induced angina, congestive heart disease, ischemia, recurrent ischemia, reperfusion injury, myocardial infarction, acute coronary syndrome, peripheral arterial disease, LQT syndrome, hypertrophic cardiomyopathy, pulmonary hypertension and intermittent claudication.

In one embodiment, the compound or compounds of the disclosure is selected from the group consisting of:

6-(2-propoxy-4-(trifluoromethoxy)phenyl)-3-(pyrimidin-2-ylmethyl)-3,4-dihydro-2H-benzo[e][1,3]oxazin-2-one, 3-(pyrimidin-2-ylmethyl)-8-(trifluoromethoxy)-3,4-dihydrofluoreno[3,2-e][1,3]oxazin-2(10H)-one, 6-(2-propoxy-4-(trifluoromethyl)phenyl)-3-(pyrimidin-2-ylmethyl)-3,4-dihydro-2H-benzo[e][1,3]oxazin-2-one, 6-(2,2-difluorobenzo[d][1,3]dioxol-5-yl)-3-(pyrimidin-2-ylmethyl)-3,4-dihydro-2H-benzo[e][1,3]oxazin-2-one, 3-(pyridin-2-ylmethyl)-6-(4-(trifluoromethyl)phenyl)-3,4-dihydro-2H-benzo[e][1,3]oxazin-2-one, 6-(3-methyl-4-(trifluoromethoxy)phenyl)-3-(pyridin-2-ylmethyl)-3,4-dihydro-2H-benzo[e][1,3]oxazin-2-one, 6-(2-methyl-4-(trifluoromethoxy)phenyl)-3-(pyridin-2-ylmethyl)-3,4-dihydro-2H-benzo[e][1,3]oxazin-2-one, 6-(2-methoxy-4-(trifluoromethoxy)phenyl)-3-(pyridin-2-ylmethyl)-3,4-dihydro-2H-benzo[e][1,3]oxazin-2-one, 6-(2-fluoro-4-(trifluoromethoxy)phenyl)-3-(pyridin-2-ylmethyl)-3,4-dihydro-2H-benzo[e][1,3]oxazin-2-one, 3-(pyridin-2-ylmethyl)-6-(4-(trifluoromethoxy)phenyl)-3,4-dihydro-2H-benzo[e][1,3]oxazin-2-one, 6-(2-propoxy-4-(trifluoromethyl)phenyl)-3-(2-(pyrimidin-2-yl)ethyl)-3,4-dihydro-2H-benzo[e][1,3]oxazin-2-one, 6-(2-methoxy-oz-3-(2-(pyrimidin-2-yl)ethyl)-3,4-dihydro-2H-benzo[e][1,3]oxazin-2-one, 6-(3-methyl-4-(trifluoromethoxy)phenyl)-3-(2-(pyrimidin-2-yl)ethyl)-3,4-dihydro-2H-benzo[e][1,3]oxazin-2-one, 6-(2-fluoro-4-(trifluoromethoxy)phenyl)-3-(2-(pyrimidin-2-yl)ethyl)-3,4-dihydro-2H-benzo[e][1,3]oxazin-2-one, 3-(2-(pyrimidin-2-yl)ethyl)-6-(4-(trifluoromethyl)phenyl)-3,4-dihydro-2H-benzo[e][1,3]oxazin-2-one, 3-(2-(pyrimidin-2-yl)ethyl)-6-(4-(trifluoromethoxy)phenyl)-3,4-dihydro-2H-benzo[e][1,3]oxazin-2-one, 3-((1-((2-methyl-1H-imidazol-1-yl)methyl)cyclopropyl)methyl)-6-(4-(trifluoromethoxy)phenyl)-3,4-dihydro-2H-benzo[e][1,3]oxazin-2-one, 3-((1-((2-methyl-1H-imidazol-1-yl)methyl)cyclopropyl)methyl)-6-(4-(trifluoromethyl)phenyl)-3,4-dihydro-2H-benzo[e][1,3]oxazin-2-one, 6-(2-fluoro-4-(trifluoromethoxy)phenyl)-3-((1-((2-methyl-1H-imidazol-1-yl)methyl)cyclopropyl)methyl)-3,4-dihydro-2H-benzo[e][1,3]oxazin-2-one, 3-((1-((2-methyl-1H-imidazol-1-yl)methyl)cyclopropyl)methyl)-6-(3-methyl-4-(trifluoromethoxy)phenyl)-3,4-dihydro-2H-benzo[e][1,3]oxazin-2-one, 6-(2-methoxy-4-(trifluoromethoxy)phenyl)-3-((1-((2-methyl-1H-imidazol-1-yl)methyl)cyclopropyl)methyl)-3,4-dihydro-2H-benzo[e][1,3]oxazin-2-one, 6-(2-methoxy-4-(trifluoromethoxy)phenyl)-3-(1-(pyridin-2-yl)cyclopropyl)-3,4-dihydro-2H-benzo[e][1,3]oxazin-2-one, 6-(3-methyl-4-(trifluoromethoxy)phenyl)-3 (1-(pyridin-2-yl)cyclopropyl)-3,4-dihydro-2H-benzo[e][1,3]oxazin-2-one, 6-(2-fluoro-4-(trifluoromethoxy)phenyl)-3-(1-(pyridin-2-yl)cyclopropyl)-3,4-dihydro-2H-benzo[e][1,3]oxazin-2-one, 3-(1-(pyridin-2-yl)cyclopropyl)-6-(4-(trifluoromethyl)phenyl)-3,4-dihydro-2H-benzo[e][1,3]oxazin-2-one, 3-(1-(pyridin-2-yl)cyclopropyl)-6-(4-(trifluoromethoxy)phenyl)-3,4-dihydro-2H-benzo[e][1,3]oxazin-2-one, 6-(2-fluoro-4-(trifluoromethoxy)phenyl)-3-((2-ethylpyrimidin-4-yl)methyl)-3,4-dihydro-2H-benzo[e][1,3]oxazin-2-one, 6-(2-methoxy-4-(trifluoromethoxy)phenyl)-3-((2-methylpyrimidin-4-yl)methyl)-3,4-dihydro-2H-benzo[e][1,3]oxazin-2-one, 6-(3-methyl-4-(trifluoromethoxy)phenyl)-3-((2-methylpyrimidin-4-yl)methyl)-3,4-dihydro-2H-benzo[e][1,3]oxazin-2-one, 3-((2-methylpyrimidin-4-yl)methyl)-6-(4-(trifluoromethoxy)phenyl)-3,4-dihydro-2H-benzo[e][1,3]oxazin-2-one, 6-(2-fluoro-4-(trifluoromethoxy)phenyl)-3-((5-methylpyrimidin-2-yl)methyl)-3,4-dihydro-2H-benzo[e][1,3]oxazin-2-one, 6-(3-methyl-4-(trifluoromethoxy)phenyl)-3-((5-methylpyrimidin-2-yl)methyl)-3,4-dihydro-2H-benzo[e][1,3]oxazin-2-one, 6-(2-methoxy-4-(trifluoromethoxy)phenyl)-3-((5-methylpyrimidin-2-yl)methyl)-3,4-dihydro-2H-benzo[e][1,3]oxazin-2-one, 3-((5-methylpyrimidin-2-yl)methyl)-6-(4-(trifluoromethyl)phenyl)-3,4-dihydro-2H-benzo[e][1,3]oxazin-2-one, 3-((5-methylpyrimidin-2-yl)methyl)-6-(4-(trifluoromethoxy)phenyl)-3,4-dihydro-2H-benzo[e][1,3]oxazin-2-one, 6-(2-fluoro-4-(trifluoromethoxy)phenyl)-4-methyl-3-(pyrimidin-2-ylmethyl)-3,4-dihydro-2H-benzo[e][1,3]oxazin-2-one, 4-methyl-6-(2-methyl-4-(trifluoromethoxy)phenyl)-3-(pyrimidin-2-ylmethyl)-3,4-dihydro-2H-benzo[e][1,3]oxazin-2-one, 4-methyl-6-(3-methyl-4-(trifluoromethoxy)phenyl)-3-(pyrimidin-2-ylmethyl)-3,4-dihydro-2H-benzo[e][1,3]oxazin-2-one, 6-(4-chloro-3-fluorophenyl)-4-methyl-3-(pyrimidin-2-ylmethyl)-3,4-dihydro-2H-benzo[e][1,3]oxazin-2-one, 6-(3,4-dichlorophenyl)-4-methyl-3-(pyrimidin-2-ylmethyl)-3,4-dihydro-2H-benzo[e][1,3]oxazin-2-one, 6-(2-methoxy-4-(trifluoromethoxy)phenyl)-4-methyl-3-(pyrimidin-2-ylmethyl)-3,4-dihydro-2H-benzo[e][1,3]oxazin-2-one, 7-methyl-3-(pyrimidin-2-ylmethyl)-6-(4-(trifluoromethyl)phenyl)-3,4-dihydro-2H-benzo[e][1,3]oxazin-2-one, 7-methyl-3-(pyrimidin-2-ylmethyl)-6-(4-(trifluoromethoxy)phenyl)-3,4-dihydro-2H-benzo[e][1,3]oxazin-2-one, 6-(4-chloro-3-fluorophenyl)-3-((4-methylthiazol-2-yl)methyl)-3,4-dihydro-2H-benzo[e][1,3]oxazin-2-one, 6-(2-methoxy-4-(trifluoromethoxy)phenyl)-3-((4-methylthiazol-2-yl)methyl)-3,4-dihydro-2H-benzo[e][1,3]oxazin-2-one, 6-(2-chloro-4-(trifluoromethoxy)phenyl)-3-((4-methylthiazol-2-yl)methyl)-3,4-dihydro-2H-benzo[e][1,3]oxazin-2-one, 6-(3,4-dichlorophenyl)-3-((4-methylthiazol-2-yl)methyl)-3,4-dihydro-2H-benzo[e][1,3]oxazin-2-one, 6-(2-fluoro-4-(trifluoromethoxy)phenyl)-3-((4-methylthiazol-2-yl)methyl)-3,4-dihydro-2H-benzo[e][1,3]oxazin-2-one, 6-(3-methyl-4-(trifluoromethoxy)phenyl)-3-((4-methylthiazol-2-yl)methyl)-3,4-dihydro-2H-benzo[e][1,3]oxazin-2-one, 6-(3-fluoro-4-(trifluoromethoxy)phenyl)-3-((4-methylthiazol-2-yl)methyl)-3,4-dihydro-2H-benzo[e][1,3]oxazin-2-one, 3-((4-methylthiazol-2-yl)methyl)-6-(4-(trifluoromethoxy)phenyl)-3,4-dihydro-2H-benzo[e][1,3]oxazin-2-one, 6-(3-fluoro-4-(trifluoromethoxy)phenyl)-3-(pyrimidin-2-ylmethyl)-3,4-dihydro-2H-benzo[e][1,3]oxazin-2-one, 6-(2-methoxy-4-(trifluoromethoxy)phenyl)-3-(pyrimidin-2-ylmethyl)-3,4-dihydro-2H-benzo[e][1,3]oxazin-2-one, 6-(2-methyl-4-(trifluoromethoxy)phenyl)-3-(pyrimidin-2-ylmethyl)-3,4-dihydro-2H-benzo[e][1,3]oxazin-2-one, 6-(2-fluoro-4-(trifluoromethoxy)phenyl)-3-(pyrimidin-2-ylmethyl)-3,4-dihydro-2H-benzo[e][1,3]oxazin-2-one, 8-fluoro-3-(pyrimidin-2-ylmethyl)-6-(4-(trifluoromethoxy)phenyl)-3,4-dihydro-2H-benzo[e][1,3]oxazin-2-one, 8-fluoro-6-(3-methyl-4-(trifluoromethoxy)phenyl)-3-(pyrimidin-2-ylmethyl)-3,4-dihydro-2H-benzo[e][1,3]oxazin-2-one, 6-(3-chloro-4-fluorophenyl)-3-(pyrimidin-2-ylmethyl)-3,4-dihydro-2H-benzo[e][1,3]oxazin-2-one, 6-(4-chloro-3-fluorophenyl)-3-(pyrimidin-2-ylmethyl)-3,4-dihydro-2H-benzo[e][1,3]oxazin-2-one, 6-(3-methyl-4-(trifluoromethoxy)phenyl)-3-(pyrimidin-2-ylmethyl)-3,4-dihydro-2H-benzo[e][1,3]oxazin-2-one, 3-((3-fluoropyridin-2-yl)methyl)-4-methyl-6-(4-(trifluoromethoxy)phenyl)-3,4-dihydro-2H-benzo[e][1,3]oxazin-2-one, 4-methyl-6-(3-phenoxyphenyl)-3-(pyrimidin-2-ylmethyl)-3,4-dihydro-2H-benzo[e][1,3]oxazin-2-one, 6-(2-fluoro-4-(trifluoromethyl)phenyl)-4-methyl-3-(pyrimidin-2-ylmethyl)-3,4-dihydro-2H-benzo[e][1,3]oxazin-2-one, 6-(3-(difluoromethoxy)phenyl)-4-methyl-3-(pyrimidin-2-ylmethyl)-3,4-dihydro-2H-benzo[e][1,3]oxazin-2-one, 4-methyl-3-(pyrimidin-2-ylmethyl)-6-(3-(trifluoromethoxy)phenyl)-3,4-dihydro-2H-benzo[e][1,3]oxazin-2-one, 1-(4-(4-methyl-2-oxo-3-(pyrimidin-2-ylmethyl)-3,4-dihydro-2H-benzo[e][1,3]oxazin-6-yl)phenyl)cyclopropanecarbonitrile, 4-methyl-3-(pyrimidin-2-ylmethyl)-6-(4-(trifluoromethyl)phenyl)-3,4-dihydro-2H-benzo[e][1,3]oxazin-2-one, 4-methyl-3-(pyrimidin-2-ylmethyl)-6-(4-(trifluoromethoxy)phenyl)-3,4-dihydro-2H-benzo[e][1,3]oxazin-2-one, 3-(pyrimidin-2-ylmethyl)-6-(4-(trifluoromethyl)phenyl)-3,4-dihydro-2H-benzo[e][1,3]oxazin-2-one, 3-(pyrimidin-2-ylmethyl)-6-(4-(trifluoromethoxy)phenyl)-3,4-dihydro-2H-benzo[e][1,3]oxazin-2-one, 3-(pyridin-4-ylmethyl)-6-(4-(trifluoromethyl)phenyl)-3,4-dihydro-2H-benzo[e][1,3]oxazin-2-one, 3-(pyridin-4-ylmethyl)-6-(4-(trifluoromethoxy)phenyl)-3,4-dihydro-2H-benzo[e][1,3]oxazin-2-one, 6-(2-propoxy-4-(trifluoromethoxy)phenyl)-3-(pyrimidin-2-ylmethyl)-3,4-dihydro-2H-benzo[e][1,3]oxazin-2-one, 3-(pyrimidin-2-ylmethyl)-8-(trifluoromethoxy)-3,4-dihydrofluoreno[3,2-e][1,3]oxazin-2(10H)-one, 6-(2-propoxy-4-(trifluoromethyl)phenyl)-3-(pyrimidin-2-ylmethyl)-3,4-dihydro-2H-benzo[e][1,3]oxazin-2-one 6-(2,2-difluorobenzo[d][1,3]dioxol-5-yl)-3-(pyrimidin-2-ylmethyl)-3,4-dihydro-2H-benzo[e][1,3]oxazin-2-one, 3-(pyridin-2-ylmethyl)-6-(4-(trifluoromethyl)phenyl)-3,4-dihydro-2H-benzo[e][1,3]oxazin-2-one, 6-(3-methyl-4-(trifluoromethoxy)phenyl)-3-(pyridin-2-ylmethyl)-3,4-dihydro-2H-benzo[e][1,3]oxazin-2-one, 6-(3-methyl-4-(trifluoromethoxy)phenyl)-3-(pyridin-2-ylmethyl)-3,4-dihydro-2H-benzo[e][1,3]oxazin-2-one, 6-(2-methoxy-4-(trifluoromethoxy)phenyl)-3-(pyridin-2-ylmethyl)-3,4-dihydro-2H-benzo[e][1,3]oxazin-2-one, 6-(2-fluoro-4-(trifluoromethoxy)phenyl)-3-(pyridin-2-ylmethyl)-3,4-dihydro-2H-benzo[e][1,3]oxazin-2-one 3-(pyridin-2-ylmethyl)-6-(4-(trifluoromethoxy)phenyl)-3,4-dihydro-2H-benzo[e][1,3]oxazin-2-one, 6-(2-propoxy-4-(trifluoromethyl)phenyl)-3-(2-(pyrimidin-2-yl)ethyl)-3,4-dihydro-2H-benzo[e][1,3]oxazin-2-one, 6-(2-methoxy-4-(trifluoromethoxy)phenyl)-3-(2-(pyrimidin-2-yeethyl)-3,4-dihydro-2H-benzo[e][1,3]oxazin-2-one, 6-(3-methyl-4-(trifluoromethoxy)phenyl)-3-(2-(pyrimidin-2-yl)ethyl)-3,4-dihydro-2H-benzo[e][1,3]oxazin-2-one, 6-(2-fluoro-4-(trifluoromethoxy)phenyl)-3-(2-(pyrimidin-2-yl)ethyl)-3,4-dihydro-2H-benzo[e][1,3]oxazin-2-one, 3-(2-(pyrimidin-2-yl)ethyl)-6-(4-(trifluoromethyl)phenyl)-3,4-dihydro-2H-benzo[e][1,3]oxazin-2-one, 3-(2-(pyrimidin-2-yl)ethyl)-6-(4-(trifluoromethoxy)phenyl)-3,4-dihydro-2H-benzo[e][1,3]oxazin-2-one 3-((1-((2-methyl-1H-imidazol-1-yl)methyl)cyclopropyl)methyl)-6-(4-(trifluoromethoxy)phenyl)-3,4-dihydro-2H-benzo[e][1,3]oxazin-2-one, 3-((1-((2-methyl-1H-imidazol-1-yl)methyl)cyclopropyl)methyl)-6-(4-(trifluoromethyl)phenyl)-3,4-dihydro-2H-benzo[e][1,3]oxazin-2-one, 6-(2-fluoro-4-(trifluoromethoxy)phenyl)-3-((1-((2-methyl-1H-imidazol-1-yl)methyl)cyclopropyl)methyl)-3,4-dihydro-2H-benzo[e][1,3]oxazin-2-one, 3-((1-((2-methyl-1H-imidazol-1-yl)methyl)cyclopropyl)methyl)-6-(3-methyl-4-(trifluoromethoxy)phenyl)-3,4-dihydro-2H-benzo[e][1,3]oxazin-2-one, 6-(2-methoxy-4-(trifluoromethoxy)phenyl)-3-((1-((2-methyl-1H-imidazol-1-yl)methyl)cyclopropyl)methyl)-3,4-dihydro-2H-benzo[e][1,3]oxazin-2-one, 6-(2-methoxy-4-(trifluoromethoxy)phenyl)-3-(1-(pyridin-2-yl)cyclopropyl)-3,4-dihydro-2H-benzo[e][1,3]oxazin-2-one, 6-(3-methyl-4-(trifluoromethoxy)phenyl)-3-(1-(pyridin-2-yl)cyclopropyl)-3,4-dihydro-2H-benzo[e][1,3]oxazin-2-one, 6-(2-fluoro-4-(trifluoromethoxy)phenyl)-3-(1-(pyridin-2-yl)cyclopropyl)-3,4-dihydro-2H-benzo[e][1,3]oxazin-2-one, 3-(1-(pyridin-2-yl)cyclopropyl)-6-(4-(trifluoromethyl)phenyl)-3,4-dihydro-2H-benzo[e][1,3]oxazin-2-one, 3-(1-(pyridin-2-yl)cyclopropyl)-6-(4-(trifluoromethoxy)phenyl)-3,4-dihydro-2H-benzo[e][1,3]oxazin-2-one, 6-(2-fluoro-4-(trifluoromethoxy)phenyl)-3-((2-methylpyrimidin-4-yl)methyl)-3,4-dihydro-2H-benzo[e][1,3]oxazin-2-one, 6-(2-methoxy-4-(trifluoromethoxy)phenyl)-3-((2-methylpyrimidin-4-yl)methyl)-3,4-dihydro-2H-benzo[e][1,3]oxazin-2-one, 6-(3-methyl-4-(trifluoromethoxy)phenyl)-3-((2-methylpyrimidin-4-yl)methyl)-3,4-dihydro-2H-benzo[e][1,3]oxazin-2-one, 3-((2-methylpyrimidin-4-yl)methyl)-6-(4-(trifluoromethoxy)phenyl)-3,4-dihydro-2H-benzo[e][1,3]oxazin-2-one, 6-(2-fluoro-4-(trifluoromethoxy)phenyl)-3-((5-methylpyrimidin-2-yl)methyl)-3,4-dihydro-2H-benzo[e][1,3]oxazin-2-one, 6-(3-methyl-4-(trifluoromethoxy)phenyl)-3-((5-methylpyrimidin-2-yl)methyl)-3,4-dihydro-2H-benzo[e][1,3]oxazin-2-one, 6-(2-methoxy-4-(trifluoromethoxy)phenyl)-3-((5-methylpyrimidin-2-yl)methyl)-3,4-dihydro-2H-benzo[e][1,3]oxazin-2-one, 3-((5-methylpyrimidin-2-yl)methyl)-6-(4-(trifluoromethyl)phenyl)-3,4-dihydro-2H-benzo[e][1,3]oxazin-2-one, 3-((5-methylpyrimidin-2-yl)methyl)-6-(4-(trifluoromethoxy)phenyl)-3,4-dihydro-2H-benzo[e][1,3]oxazin-2-one, 6-(2-fluoro-4-(trifluoromethoxy)phenyl)-4-methyl-3-(pyrimidin-2-ylmethyl)-3,4-dihydro-2H-benzo[e][1,3]oxazin-2-one, 4-methyl-6-(2-methyl-4-(trifluoromethoxy)phenyl)-3-(pyrimidin-2-ylmethyl)-3,4-dihydro-2H-benzo[e][1,3]oxazin-2-one, 4-methyl-6-(3-methyl-4-(trifluoromethoxy)phenyl)-3-(pyrimidin-2-ylmethyl)-3,4-dihydro-2H-benzo[e][1,3]oxazin-2-one, 6-(4-chloro-3-fluorophenyl)-4-methyl-3-(pyrimidin-2-ylmethyl)-3,4-dihydro-2H-benzo[e][1,3]oxazin-2-one 6-(3,4-dichlorophenyl)-4-methyl-3-(pyrimidin-2-ylmethyl)-3,4-dihydro-2H-benzo[e][1,3]oxazin-2-one, 6-(2-methoxy-4-(trifluoromethoxy)phenyl)-4-methyl-3-(pyrimidin-2-ylmethyl)-3,4-dihydro-2H-benzo[e][1,3]oxazin-2-one, 7-methyl-3-(pyrimidin-2-ylmethyl)-6-(4-(trifluoromethyl)phenyl)-3,4-dihydro-2H-benzo[e][1,3]oxazin-2-one, 7-methyl-3-(pyrimidin-2-ylmethyl)-6-(4-(trifluoromethoxy)phenyl)-3,4-dihydro-2H-benzo[e][1,3]oxazin-2-one, 6-(4-chloro-3-fluorophenyl)-3-((4-methylthiazol-2-yl)methyl)-3,4-dihydro-2H-benzo[e][1,3]oxazin-2-one, 6-(2-methoxy-4-(trifluoromethoxy)phenyl)-3-((4-methylthiazol-2-yl)methyl)-3,4-dihydro-2H-benzo[e][1,3]oxazin-2-one, 6-(2-chloro-4-(trifluoromethoxy)phenyl)-3-((4-methylthiazol-2-yl)methyl)-3,4-dihydro-2H-benzo[e][1,3]oxazin-2-one, 6-(3,4-dichlorophenyl)-3-((4-methylthiazol-2-yl)methyl)-3,4-dihydro-2H-benzo[e][1,3]oxazin-2-one, 6-(2-fluoro-4-(trifluoromethoxy)phenyl)-3-((4-methylthiazol-2-yl)methyl)-3,4-dihydro-2H-benzo[e][1,3]oxazin-2-one, 6-(3-methyl-4-(trifluoromethoxy)phenyl)-3-((4-methylthiazol-2-yl)methyl)-3,4-dihydro-2H-benzo[e][1,3]oxazin-2-one, 6-(3-fluoro-4-(trifluoromethoxy)phenyl)-3-((4-methylthiazol-2-yl)methyl)-3,4-dihydro-2H-benzo[e][1,3]oxazin-2-one, 3-((4-methylthiazol-2-yl)methyl)-6-(4-(trifluoromethoxy)phenyl)-3,4-dihydro-2H-benzo[e][1,3]oxazin-2-one, 6-(3-fluoro-4-(trifluoromethoxy)phenyl)-3-(pyrimidin-2-ylmethyl)-3,4-dihydro-2H-benzo[e][1,3]oxazin-2-one, 6-(2-methoxy-4-(trifluoromethoxy)phenyl)-3-(pyrimidin-2-ylmethyl)-3,4-dihydro-2H-benzo[e][1,3]oxazin-2-one, 6-(2-methyl-4-(trifluoromethoxy)phenyl)-3-(pyrimidin-2-ylmethyl)-3,4-dihydro-2H-benzo[e][1,3]oxazin-2-one, 6-(2-fluoro-4-(trifluoromethoxy)phenyl)-3-(pyrimidin-2-ylmethyl)-3,4-dihydro-2H-benzo[e][1,3]oxazin-2-one, 8-fluoro-3-(pyrimidin-2-ylmethyl)-6-(4-(trifluoromethoxy)phenyl)-3,4-dihydro-2H-benzo[e][1,3]oxazin-2-one, 8-fluoro-6-(3-methyl-4-(trifluoromethoxy)phenyl)-3-(pyrimidin-2-ylmethyl)-3,4-dihydro-2H-benzo[e][1,3]oxazin-2-one, 6-(3-chloro-4-fluorophenyl)-3-(pyrimidin-2-ylmethyl)-3,4-dihydro-2H-benzo[e][1,3]oxazin-2-one, 6-(4-chloro-3-fluorophenyl)-3-(pyrimidin-2-ylmethyl)-3,4-dihydro-2H-benzo[e][1,3]oxazin-2-one,
6-(3-methyl-4-(trifluoromethoxy)phenyl)-3-(pyrimidin-2-ylmethyl)-3,4-dihydro-2H-benzo[e][1,3]oxazin-2-one,
3-((3-fluoropyridin-2-yl)methyl)-4-methyl-6-(4-(trifluoromethoxy)phenyl)-3,4-dihydro-2H-benzo[e][1,3]oxazin-2-one,
4-methyl-6-(3-phenoxyphenyl)-3-(pyrimidin-2-ylmethyl)-3,4-dihydro-2H-benzo[e][1,3]oxazin-2-one,
6-(2-fluoro-4-(trifluoromethyl)phenyl)-4-methyl-3-(pyrimidin-2-ylmethyl)-3,4-dihydro-2H-benzo[e][1,3]oxazin-2-one,
6-(3-(difluoromethoxy)phenyl)-4-methyl-3-(pyrimidin-2-ylmethyl)-3,4-dihydro-2H-benzo[e][1,3]oxazin-2-one,
4-methyl-3-(pyrimidin-2-ylmethyl)-6-(3-(trifluoromethoxy)phenyl)-3,4-dihydro-2H-benzo[e][1,3]oxazin-2-one,
1-(4-(4-methyl-2-oxo-3-(pyrimidin-2-ylmethyl)-3,4-dihydro-2H-benzo[e][1,3]oxazin-6-yl)phenyl)cyclopropanecarbonitrile,
4-methyl-3-(pyrimidin-2-ylmethyl)-6-(4-(trifluoromethyl)phenyl)-3,4-dihydro-2H-benzo[e][1,3]oxazin-2-one,
4-methyl-3-(pyrimidin-2-ylmethyl)-6-(4-(trifluoromethoxy)phenyl)-3,4-dihydro-2H-benzo[e][1,3]oxazin-2-one,
3-(pyrimidin-2-ylmethyl)-6-(4-(trifluoromethyl)phenyl)-3,4-dihydro-2H-benzo[e][1,3]oxazin-2-one,
3-(pyrimidin-2-ylmethyl)-6-(4-(trifluoromethoxy)phenyl)-3,4-dihydro-2H-benzo[e][1,3]oxazin-2-one,
3-(pyridin-4-ylmethyl)-6-(4-(trifluoromethyl)phenyl)-3,4-dihydro-2H-benzo[e][1,3]oxazin-2-one, and
3-(pyridin-4-ylmethyl)-6-(4-(trifluoromethoxy)phenyl)-3,4-dihydro-2H-benzo[e][1,3]oxazin-2-one;
or a pharmaceutically acceptable salt thereof.

4. Further Embodiments

In some embodiments, the compounds provided by the present disclosure may be effective in the treatment of conditions or diseases known to respond to administration of late sodium channel blockers, including but not limited to cardiovascular diseases such as atrial arrhythmias (e.g. atrial fibrillation), ventricular arrhythmias (e.g. ventricular fibrillation, or ventricular tachycardia), Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, and myocardial infarction. In some embodiments, compounds provided by the present disclosure may be used in the treatment of diseases affecting the neuromuscular system resulting in pain, itching, seizures, or paralysis, or in the treatment of diabetes or reduced insulin sensitivity, and disease states related to diabetes, such as diabetic, peripheral neuropathy.

Certain compounds of the disclosure may also possess a sufficient activity in modulating neuronal sodium channels, i.e., $Na_V$ 1.1., 1.2, 1.3, 1.5, 1.7, and/or 1.8, and may have appropriate pharmacokinetic properties such that they may be active with regard to the central and/or peripheral nervous system. Consequently, compounds of the present disclosure may also be useful in the treatment of epilepsy or pain or itching or headache of a neuropathic origin.

In one embodiment, this disclosure provides a method of treating a disease state in a mammal, particularly a human that is alleviable by treatment with an agent capable of reducing late sodium current, comprising administering to said mammal, particularly a human, in need thereof, a therapeutically effective dose of a compound of Formula I or other novel compounds or combination of compounds disclosed herein. In another embodiment, the disease state is a cardiovascular disease selected from one or more of atrial and ventricular arrhythmias, heart failure, Prinzmetal's (variant) angina, stable angina, unstable angina, exercise induced angina, congestive heart disease, ischemia, recurrent ischemia, reperfusion injury, myocardial infarction, acute coronary syndrome, peripheral arterial disease, pulmonary hypertension, and intermittent claudication.

In another embodiment, the disclosure provides a compound of formula (I) disclosed herein for the treatment of Long QT syndrome comprising administering an effective dose of said compound of formula (I) to a human in need thereof. Specifically, in one embodiment, the disclosure provides a compound useful for the treatment of Long QT syndrome selected from the group consisting of LQT1, LQT2, LQT3, LQT4, and LQT5, comprising administering an effective amount of said compound of formula (I) to a human in need thereof "Long QT Syndrome" or "LQTS" is caused by dysfunction of protein structures in the heart cells called ion channels or protein structures modulating the activity of ion channels. These channels control the flow of ions like potassium, sodium and calcium molecules. The flow of these ions in and out of the cells produces the electrical activity of the heart. Abnormalities of these channels can be acquired or inherited. The acquired form is usually caused by prescription medications, however, the inherited form occurs when a mutation develops in one of several genes that produce or "encode" one of the ion channels that control electrical repolarization. The mutant gene produces abnormal channels to be formed, and as these abnormal channels are dysfunctional and the electrical repolarization of the heart takes longer. This is manifested on the electrocardiogram (ECG, EKG) by a prolonged QT interval.

"QT prolongation", or a prolonged QT interval, makes the heart vulnerable to polymorphic ventricular tachycardias, one kind of which is a fast, abnormal heart rhythm known as Torsade de Pointes. The corrected QT interval (or "QTc") represents the QT interval normalized for a heart rate of 60 beats/min. There are several methods for calculating the QTc, such as Bazett's formula ($QT_B=QT/\sqrt{RR}$), Fridericia's formula ($QT_B=QT/\sqrt[3]{RR}$), or a regression-based approach ($QT_{LC}=QT+0.154(1-RR)$), where RR is the interval from the onset of one QRS complex to the onset of the next QRS complex.

Congenital LQTS is caused by mutations in at least one of fifteen genes with mutations in three genes accounting for approximately 70% of genotype positive cases (LQT1-LQT3):

| Disease | Gene | Chromosome | Ion Channel or Protein |
|---|---|---|---|
| LQT1 | KCNQ1 (KVLQT1) | 11p15.5 | $I_{Ks}$ subunit* |
| LQT2 | HERG | 7q35-46 | $I_{Kr}$ |
| LQT3 | SCN5A | 3q21-24 | $I_{Na}$ |
| LQT4 | ANKB | 4q25-27 | Ankyrin B |
| LQT5 | KCNE1 (MinK) | 21q22.1 | $I_{Ks}$ subunit |

*Homozygous carriers of novel mutations of KVLQT1 have Jervell, Lange-Nielsen syndrome. KVLQT1 and MinK co-assemble to form the IKs channel.

The LQT diseases and ion channels listed in the table above are the same for acquired LQTS as they are for inherited LQTS. The inherited form of LQTS occurs when a mutation develops in one of several genes that produce or "encode" one of the ion channels or ion channel modulators that control electrical repolarization. There are at least fifteen different forms of inherited LQTS, characterized as LQT1-LQT15.

They were originally characterized by the differing shape of the ECG trace, and have subsequently been associated with specific gene mutations. The LQT1 form is the most frequent, accounting for approximately 30-35% of the genotyped patients. LQT2 is next at about 25-30%, and LQT3, from SCN5A mutations accounts for about 5-10%. Patients with two mutations seem to account for less than 1% of all patients, but this may change as more patients are studied with the newer genetic techniques.

In another embodiment, the disclosure provides a compound of formula (I) disclosed herein for the treatment of hypertrophic cardiomyopathy (HCM), comprising administering a therapeutically effective amount of said compound of formula (I) to a human in need thereof. "Hypertrophic cardiomyopathy" is a disease in which the heart muscle (myocardium) becomes abnormally thick or hypertrophied. This thickened heart muscle can make it harder for the heart to pump blood. Hypertrophic cardiomyopathy may also affect the heart's electrical system. HCM is the most common genetic cardiac disease, affecting approximately 1 in 500 people. It is caused by autosomal-dominant mutations in genes encoding critical components of the cardiac sarcomere. HCM is recognized clinically as unexplained left ventricular (LV) hypertrophy (typically ≥15 mm thickness of the ventricular wall) in the absence of other cardiac or systemic conditions capable of producing the magnitude of hypertrophy observed. Typical symptoms include shortness of breath, angina, palpitations, fatigue and syncope. In a small percentage of patients, sudden cardiac death may be the first presentation. HCM is a leading cause of sudden cardiac death in young adults.

In another embodiment, the disease state suitable for treatment with a compound of formula I is diabetes or diabetic peripheral neuropathy. In a further embodiment, the disease state results in one or more of neuropathic pain, epilepsy, headache, seizures, or paralysis.

In one embodiment, this disclosure provides a method of treating diabetes in a mammal, particularly a human, comprising administering to a mammal, particularly human, in need thereof a therapeutically effective dose of a compound of Formula I or other novel compounds or combinations disclosed herein. Diabetes mellitus is a disease characterized by hyperglycemia; altered metabolism of lipids, carbohydrates and proteins; and an increased risk of complications from vascular disease. Diabetes is an increasing public health problem, as it is associated with both increasing age and obesity.

There are two major types of diabetes mellitus: 1) Type I, also known as insulin dependent diabetes (IDDM) and 2) Type II, also known as insulin independent or non-insulin dependent diabetes (NIDDM). Both types of diabetes mellitus are due to insufficient amounts of circulating insulin and/or a decrease in the response of peripheral tissue to insulin.

Type I diabetes results from the body's failure to produce insulin, the hormone that "unlocks" the cells of the body, allowing glucose to enter and fuel them. The complications of Type I diabetes include heart disease and stroke; retinopathy (eye disease); kidney disease (nephropathy); neuropathy (nerve damage); as well as maintenance of good skin, foot and oral health.

Type II diabetes results from the body's inability to either produce enough insulin or the cells inability to use the insulin that is naturally produced by the body. The condition where the body is not able to optimally use insulin is called insulin resistance. Type II diabetes is often accompanied by high blood pressure and this may contribute to heart disease. In patients with type II diabetes mellitus, stress, infection, and medications (such as corticosteroids) can also lead to severely elevated blood sugar levels. Accompanied by dehydration, severe blood sugar elevation in patients with type II diabetes can lead to an increase in blood osmolality (hyperosmolar state). This condition can lead to coma.

It has been suggested that ranolazine (RANEXA®, a selective inhibitor of late $I_{Na}$ (INaL)) may be an antidiabetic agent that causes β-cell preservation and enhances insulin secretion in a glucose-dependent manner in diabetic mice (see, Y. Ning et al. J Pharmacol Exp Ther. 2011, 337(1), 50-8). Therefore it is contemplated that compounds of Formula (I) or novel compounds or combinations disclosed herein may be useful as antidiabetic agents for the treatment of diabetes singly or in combination with ranolazine or other antidiabetic agents.

5. Pharmaceutical Compositions and Administration

Compounds provided in accordance with the present disclosure are usually administered in the form of pharmaceutical compositions. This disclosure therefore provides pharmaceutical compositions that contain, as the active ingredient, one or more of the compounds described herein, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such pharmaceutical compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, including for example, rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer. One of skill in the art is aware of methods and procedures for preparing and/or administering formulations described herein.

One mode for administration is parenteral, particularly by injection. The forms in which the novel compositions of the present disclosure may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present disclosure in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof. For parenteral administration, sterile injectable solutions are prepared containing a therapeutically effective amount, e.g., 0.1 mg to 700 mg, of a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

Oral administration is another route for administration of compounds in accordance with the present disclosure. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the disclosure can be formulated so as to provide quick, sustained or delayed release of the active ingredient(s) after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present disclosure employs transdermal delivery devices ("patches"). Such transdermal patches may be used to provide continuous or discontinuous infusion of the compounds of the present disclosure in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, or ampoule). The compounds are generally administered in a pharmaceutically effective amount. For oral administration, each dosage unit may contain from 1 mg to 1 g, or alternatively 100 mg to 500 mg, 200 mg to 400 mg, or 400 mg to 800 mg, of a compound described herein. For parenteral administration, a suitable dose may be from 0.1 mg to 700 mg, 1 mg to 300 mg, or alternatively, 5 mg to 100 mg, of a compound a compound described herein. It will be understood, however, that the amount of the compound actually administered usually will be determined by a physician, in view of the relevant circumstances, including the condition to be treated, the chosen route of administration, the actual compound(s) administered and its relative activity, the age, weight, and response of the individual patient, the severity of the patient's symptoms, and the like.

For preparing solid compositions such as tablets, the principal active ingredient is mixed with a pharmaceutical excipient to foiin a solid preformulation composition containing a homogeneous mixture of a compound of the present disclosure. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present disclosure may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

Combination Therapy

Patients being treated by administration of the late sodium channel blockers of the disclosure may exhibit diseases or conditions that benefit from treatment with other therapeutic agents. These diseases or conditions can be of cardiovascular nature or can be related to pulmonary disorders, metabolic disorders, gastrointestinal disorders and the like. Additionally, some coronary patients being treated by administration of the late sodium channel blockers of the disclosure exhibit conditions that can benefit from treatment with therapeutic agents that are antibiotics, analgesics, and/or antidepressants and anti-anxiety agents.

Cardiovascular Agent Combination Therapy

Cardiovascular related diseases or conditions that can benefit from a combination treatment of the late sodium channel blockers of the disclosure with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the late sodium channel blockers of the disclosure with therapeutic agents suitable for treating cardiovascular related conditions allows enhancement in the standard of care therapy the patient is currently receiving. In some embodiments, the late sodium channel blockers of the disclosure are co-administered with ranolazine (RANEXA®).

Anti-anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral®), atenolol (Tenormin®), betaxolol (Kerlone®), bisoprolol/hydrochlorothiazide (Ziac®), bisoprolol (Zebeta®), carteolol (Cartol®), esmolol (Brevibloc®), labetalol (Normodyne®, Trandate®), metoprolol (Lopressor®, Toprol® XL), nadolol (Corgard®), propranolol (Inderal®), sotalol (Betapace®), and timolol (Blocadren®).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc®, Lotrel®), bepridil (Vascor®), diltiazem (Cardizem®, Tiazac®), felodipine (Plendil®), nifedipine (Adalat®, Procardia®), nimodipine (Nimotop®), nisoldipine (Sular®), verapamil (Calan®, Isoptin®, Verelan®), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn®), furosemide (Lasix®), bumetanide (Bumex®), spironolactone (Aldactone®), and eplerenone (Inspra®).

Angiotensin converting enzyme (ACE) inhibitors reduce the workload on the heart by expanding the blood vessels and decreasing resistance to blood flow. Examples of ACE inhibitors include benazepril (Lotensin®), captopril (Capoten®), enalapril (Vasotec®), fosinopril (Monopril®), lisinopril (Prinivil®, Zestril®), moexipril (Univasc®), perindopril (Aceon®) quinapril (Accupril®), ramipril (Altace®), and trandolapril (Mavik®).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (Plavix®), prasugrel (Effient®), dipyridamole, cilostazol, persantine sulfinpyrazone, dipyridamole, indomethacin, and glycoprotein llb/llla inhibitors, such as abciximab, tirofiban, and eptifibatide (Integrelin®). Beta blockers and calcium channel blockers also have a platelet-inhibiting effect.

Anticoagulants prevent blood clots from growing larger and prevent the formation of new clots. Examples of anticoagulants include bivalirudin (Angiomax®), warfarin (Coumadin®), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of anti arrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of interest (see U.S. Patent Application Publication No. 2010/0056536 and U.S. Patent Application Publication No. 2011/0183990, the entirety of which are incorporated herein).

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot formation. Examples of antihypertensive agents include alpha-1-adrenergic antagonists, such as prazosin (Minipress®), doxazosin mesylate (Cardura®), prazosin hydrochloride (Minipress®), prazosin, polythiazide (Minizide®), and terazosin hydrochloride (Hytrin®); beta-adrenergic antagonists, such as propranolol (Inderal®), nadolol (Corgard®), timolol (Blocadren®), metoprolol (Lopressor®), and pindolol (Visken®); central alpha-adrenoceptor agonists, such as clonidine hydrochloride (Catapres®), clonidine hydrochloride and chlorthalidone (Clorpres®, Combipres®), guanabenz Acetate (Wytensin®), guanfacine hydrochloride (Tenex®), methyldopa (Aldomet®), methyldopa and chlorothiazide (Aldoclor®), methyldopa and hydrochlorothiazide (Aldoril®); combined alpha/beta-adrenergic antagonists, such as labetalol (Normodyne®, Trandate®), carvedilol (Coreg®); adrenergic neuron blocking agents, such as guanethidine (Ismelin®), reserpine (Serpasil®); central nervous system-acting antihypertensives, such as clonidine (Catapres®), methyldopa (Aldomet®), guanabenz (Wytensin®); anti-angiotensin II agents; ACE inhibitors, such as perindopril (Aceon®) captopril (Capoten®), enalapril (Vasotec®), lisinopril (Prinivil®, Zestril®); angiotensin- II receptor antagonists, such as candesartan (Atacand®), eprosartan (Teveten®), irbesartan (Avapro®), losartan (Cozaar®), telmisartan (Micardis®), valsartan (Diovan®); calcium channel blockers, such as verapamil (Calan®, Isoptin®), diltiazem (Cardizem®), nifedipine (Adalat®, Procardia®); diuretics; direct vasodilators, such as nitroprusside (Nipride®), diazoxide (Hyperstat® IV), hydralazine (Apresoline®), minoxidil (Loniten®), verapamil; and potassium channel activators, such as aprikalim, bimakalim, cromakalim, emakalim, nicorandil, and pinacidil. A patient suffering from hypertension may benefit from treatment with a combination therapy comprising administering to the patient a of formula I as disclosed herein in combination with at least one antihypertensive therapeutic agent.

Lipid Lowering Agents

Lipid lowering agents are used to lower the amounts of cholesterol or fatty sugars present in the blood. Examples of lipid lowering agents include bezafibrate (Bezalip®), ciprofibrate (Modalim®), and statins, such as atorvastatin (Lipitor®), fluvastatin (Lescol®), lovastatin (Mevacor®, Altocor®), mevastatin, pitavastatin (Livalo®, Pitava®) pravastatin (Lipostat®), rosuvastatin (Crestor®), and simvastatin (Zocor®).

In this disclosure, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient a compound of Formula I in combination with at least one therapeutic agent (potential combination therapy agents disclosed herein), to a patient in need thereof.

Pulmonary Disorders Combination Therapy

Pulmonary disorder refers to any disease or condition related to the lungs. Examples of pulmonary disorders include, without limitation, pulmonary hypertension, asthma, chronic obstructive pulmonary disease (COPD), bronchitis, and emphysema. Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire®, Bricanyl®), albuterol (Proventil®), salmeterol (Serevent®, Serevent Diskus®), theophylline, ipratropium bromide (Atrovenn, tiotropium (Spiriva®), methylprednisolone (Solu-Medrol®, Medrol®), magnesium, and potassium.

Pulmonary arterial hypertension (PAH) is a form of pulmonary disorder. Compounds useful for the treatment of PAH include the endothelin receptor antagonists, PDE5 receptor antagonists, etc. Examples of agent useful for the treatment of PAH include for example, ambrisentan (Letairis®), Bosentan (Tracleer®), macicentan (Opsumit®), riociguat (Adempas®), Epoprostinol sodium (Flolan®), tresprostinil (Remodulin ®, Tyvaso®), sildenafil (Revatio®), tadalafil (Adcirca®).

Compounds of the disclosure herein may be used for the treatment or prophylaxis of pulmonary disorders comprising administering a combination of said compound of the present disclosure and an agent or agents used to treat pulmonary disorders.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics. Compounds of the disclosure herein may be used for the treatment or prophylaxis of metabolic disorders comprising administering said compound of the present disclosure singly or in combination with an agent or agents used to treat metabolic disorders, to a patient in need thereof.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis. Compounds of the disclosure herein may be used for the treatment or prophylaxis of peripheral vascular disorders comprising administering said compound of the present disclosure singly or in combination with an agent or agents used to treat peripheral vascular disorders, to a patient in need thereof.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix®), lansoprazole (Prevacid®), esomeprazole (Nexium®), omeprazole (Prilosec®), rabeprazole; H2 blockers, such as cimetidine (Tagamet®), ranitidine (Zantac®), famotidine (Pepcid®), nizatidine (Axid®); prostaglandins, such as misoprostol (Cytotec®); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with a compound as disclosed herein.

Antibiotics

Antibiotics are therapeutic agents that kill, or stop the growth of, microorganisms, including both bacteria and fungi. Example of antibiotic agents include β-Lactam antibiotics, including penicillins (amoxicillin), cephalosporins, such as cefazolin, cefuroxime, cefadroxil (Duricef®), cephalexin (Keflex®), cephradine (Velosef®), cefaclor (Ceclor®), cefuroxime axtel (Ceftin®), cefprozil (Cefzil®), loracarbef (Lorabid®), cefixime (Suprax®), cefpodoxime proxetil (Vantin®), ceftibuten (Cedax®), cefdinir (Omnicef®), ceftriaxone (Rocephin®), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinones, such as linezolid; and sulfa antibiotics, such as sulfisoxazole. Compounds of the disclosure herein may be used for the treatment or prophylaxis of bacterial infections comprising administering said compound of the present disclosure singly or in combination with an agent or agents used to treat bacterial infections, to a patient in need thereof.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the late sodium channel blockers of the disclosure to treat neuropathic pain via inhibition of the $Na_V$ 1.7 and 1.8 sodium channels, combination with analgesics are particularly envisioned. See U.S. Patent Application Publication 20090203707.

Antidepressant and Anti-anxiety Agents

Antidepressant and anti-anxiety agents include those agents used to treat anxiety disorders, depression, and those used as sedatives and tranquilizers. Examples of antidepressant and anti-anxiety agents include benzodiazepines, such as diazepam, lorazepam, and midazolam; enzodiazepines; barbiturates; glutethimide; chloral hydrate; meprobamate; sertraline (Zoloft®, Lustral®, Apo-Sertral®, Asentra®, Gladem®, Serlift®, Stimuloton®); escitalopram (Lexapro®, Cipralex®); fluoxetine (Prozac®, Sarafem®, Fluctin®, Fontex®, Prodep®, Fludep®, Lovan); venlafaxine (Effexor® XR, Efexor®); citalopram (Celexa®, Cipramil®, Talohexane®); paroxetine (Paxil®, Seroxat®, Aropax®); trazodone (Desyrel®); amitriptyline (Elavil®); and bupropion (Wellbutrin®, Zyban®).

Accordingly, one aspect of the disclosure provides for a composition comprising the late sodium channel blockers of the disclosure and at least one therapeutic agent disclosed herein for combination treatment or prophylaxis. In an alternative embodiment, the composition comprises the late sodium channel blockers of the disclosure and at least two therapeutic agents herein for combination treatment or prophylaxis. In further alternative embodiments, the composition comprises the late sodium channel blockers of the disclosure and at least three therapeutic agents, the late sodium channel blockers of the disclosure and at least four therapeutic agents, or the late sodium channel blockers of the disclosure and at least five therapeutic agents.

The methods of combination therapy include co-administration of a single formulation containing the late sodium channel blockers of the disclosure and therapeutic agent or agents, essentially contemporaneous administration of more than one formulation comprising the late sodium channel blocker of the disclosure and therapeutic agent or agents, and consecutive administration of a late sodium channel blocker of the disclosure and therapeutic agent or agents, in any order, wherein preferably there is a time period where the late sodium channel blocker of the disclosure and therapeutic agent or agents simultaneously exert their therapeutic effect.

6. Synthesis of Example Compounds

The compounds of the disclosure may be prepared using methods disclosed herein and routine modifications thereof which will be apparent given the disclosure herein and methods well known in the art. Conventional and well-known synthetic methods may be used in addition to the teachings herein. The synthesis of compounds described herein, e.g. compounds having structures described by Formula I, II or other formulas or compounds disclosed herein, may be accomplished as described in the following examples. If available, reagents may be purchased commercially, e.g. from Sigma Aldrich or other chemical suppliers.

General Syntheses

Typical embodiments of compounds in accordance with the present disclosure may be synthesized using the general reaction schemes described below. It will be apparent that given a desired product for which the substituent groups are defined, the necessary starting materials generally may be determined by inspection based on the general scheme disclosed herein. Starting materials are typically obtained from commercial sources or synthesized using published methods. For synthesizing compounds which are embodiments of the present disclosure, inspection of the structure of the compound to be synthesized in relation to the schemes disclosed herein will provide the identity of each substituent group.=

Synthetic Reaction Parameters

The compounds of this disclosure can be prepared from readily available starting materials using, for example, the following general methods and procedures. It will be appreciated that where typical or preferred process conditions (i.e., reaction temperatures, times, mole ratios of reactants, solvents, pressures, etc.) are given; other process conditions may also be used unless otherwise stated. Optimum or suitable reaction conditions may vary with the particular reactants or solvent used, but such conditions may be determined by one skilled in the art by routine optimization procedures or by reference to the art.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts (1999) *Protecting Groups in Organic Synthesis*, 3rd Edition, Wiley, N.Y., and references cited therein.

Furthermore, the compounds of this disclosure may contain one or more chiral centers. Accordingly, if desired, such compounds can be prepared or isolated as pure stereoisomers, i.e., as individual enantiomers or diastereomers or as stereoisomer-enriched mixtures. All such stereoisomers (and enriched mixtures) are included within the scope of this disclosure, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents, and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989) organic Reactions, Volumes 1-40 (John Wiley, and Sons, 1991), March's Advanced Organic Chemistry, (John Wiley, and Sons, 5$^{th}$ Edition, 2001), and Larock's Comprehensive Organic Transformations (VCH Publishers Inc., 1989).

The terms "solvent," "inert organic solvent" or "inert solvent" refer to a solvent inert under the conditions of the reaction being described in conjunction therewith (including, for example, benzene, toluene, acetonitrile, tetrahydrofuran ("THF"), dimethylformamide ("DMF"), chloroform, methylene chloride (or dichloromethane), diethyl ether, methanol, pyridine and the like). Unless specified to the contrary, the solvents used in the reactions of the present disclosure are inert organic solvents, and the reactions are carried out under an inert gas, preferably nitrogen.

The term "q.s." means adding a quantity sufficient o achieve a stated function, e.g., to bring a solution to the desired volume (i.e., 100%).

Synthesis of the Compounds of Formula I

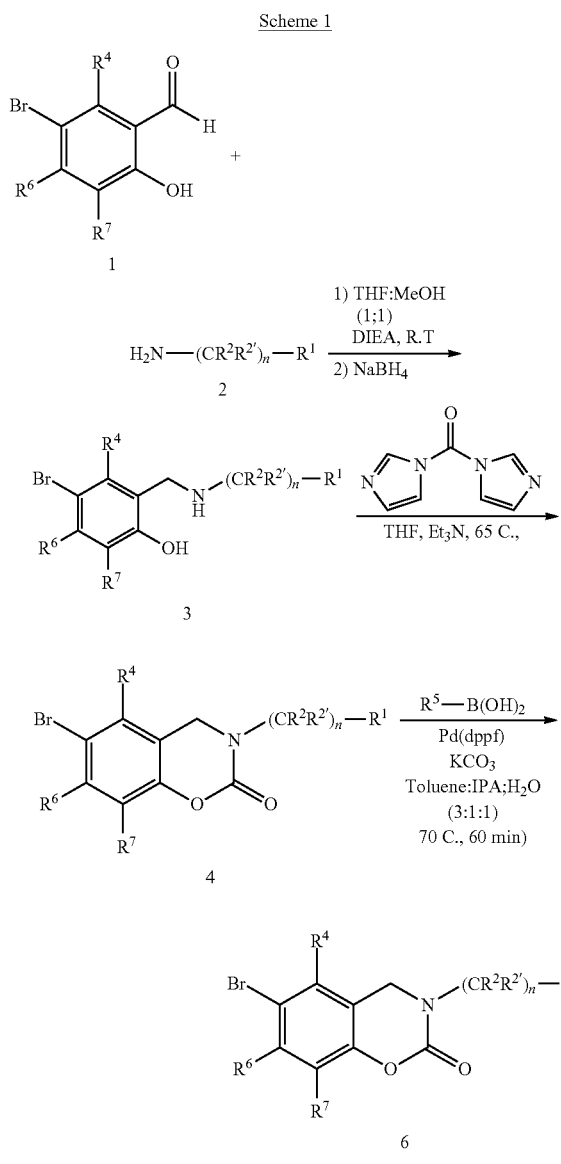

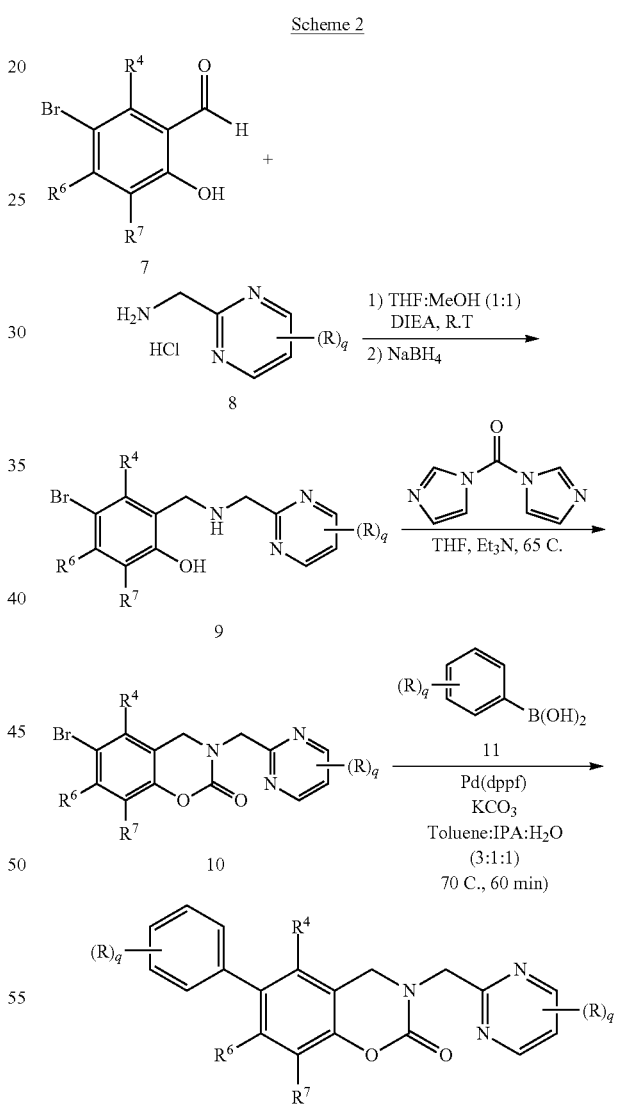

R is an optional substituent as disclosed herein and q is 1, 2 or 3.

In general, a salicyladehyde derivative of formula (1) having the desired $R^4$, $R^6$, and $R^7$ substituents is employed as a starting material with an appropriate leaving group e.g. a bromo or other suitable leaving group. The compound of formula (1) is reacted in a reductive amination reaction with an appropriate amine having the desired $(CR^2R^{2\prime})_n$—$R^1$ group of Formula (I) to form the secondary amine coupled product (3). One of ordinary skill in the art is aware of methods for accomplishing reductive amination reactions. The compound (3) is cyclized via a carbonyl insertion reaction using bisimidazolyl carbonyl (also referred to as carbonyl diimidazole (CDI)) in the presence of a suitable base (e.g. triethylamine) and a suitable solvent, e.g. tetrahydrofuran, to form the benzoisoxazinone compound 4. Palladium catalyzed (Suzuki) coupling of the intermediate (4) and a boronic acid or boronic ester source of the $R^5$ group affords the compound of formula (6) as shown.

One of skill in the art is aware that other $R^5$ groups having aryl, heteroaryl or heterocyclic cores according to the desired compound of formula (I) or other compounds or disclosed herein may be introduced as the boronic acid coupling partner or other coupling reaction partners to prepare a desired analog of compound (6) or compound of formula (I) having an aryl, heteroaryl, or heterocyclic $R^5$ group.

The preparation of compounds of formula (I) having a heterocyclic $R^1$ group e.g. imidazolyl, pyrimidine or thiazolyl may be accomplished by starting with an amine having a heterocyclic terminus. Scheme 2 below is a specific example of the above general scheme 1 showing the formation of compound (12) wherein $R^1$ is heterocyclic e.g. pyrimidinyl.

As shown in scheme 2 above, optionally substituted 2-hydroxy, 5-bromo benzaldehyde (7) is reacted with optionally substituted 2-aminomethylpyrimidine hydrochloride (8) under reductive amination conditions to provide the coupled amine product (9). For example, the reductive amination may be performed using a reducing agent such as sodium borohydride; in a suitable solvent or solvent mixtures, such as tetrahydrofuran or 1:1 THF/MeOH; a suitable base such as diisopropyl ethylamine; and under suitable temperature conditions e.g. about room temperature to provide the coupled product (9). The coupled product (9) is then reacted with carbonyldiimidazole (CDI) under known carbonyl insertion reaction conditions or as disclosed herein in the examples section. For example, the coupling may be performed in a suitable solvent such as tetrahydrofuran; a suitable base such as triethylamine; and under suitable temperature conditions e.g. about 65° C. to provide the carbamate product (10). The carbamate (10) is then reacted with an optionally substituted phenyl boronic acid (11) (or other aryl, heteroaryl, or heterocyclic boronic acid or ester) under suitable catalytic reaction conditions (e.g. Pd(dppf), $K_2CO_3$, Toluene/IPA/$H_2O$ mixture (3:1:1)) to afford the desired compound (12) or analog of formula (I) or other embodiment herein.

Optional Core Synthesis

In one embodiment, compounds of the disclosure may be made by reversing the source of aldehyde and amine to produce the reductive amination product. For example, scheme 3, highlights the use of reversed reductive amination partners to form compounds of formula (I) or other embodiment disclosed herein wherein $R^1$ is heterocyclic (e.g. optionally substituted thiazolyl). The scheme is also applicable to compounds of the disclosure wherein $R^1$ is aryl or heteroaryl. In scheme (3) the aldehyde (13) is reacted with the benzyl amine compound (14) under reductive amination conditions to provide compound (15). Compound (15) is carbonylated to form the cyclic carbamate (16) which is then coupled with an optionally substituted phenyl boronic acid (17) or ester (or optionally substituted heteroaryl or heterocyclic boronic acid or ester) via a Suzuki coupling reaction to obtain the compound (18).

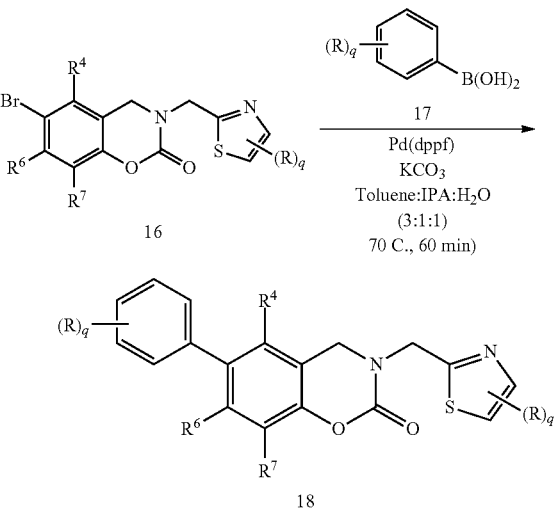

R is an optional substituent as disclosed herein and q is 1, 2 or 3.

Compounds of formula (I) or other embodiment disclosed herein wherein $R^3$ is alkyl or other disclosed substituent may be prepared by utilizing a corresponding ketone in place of the aldehyde.

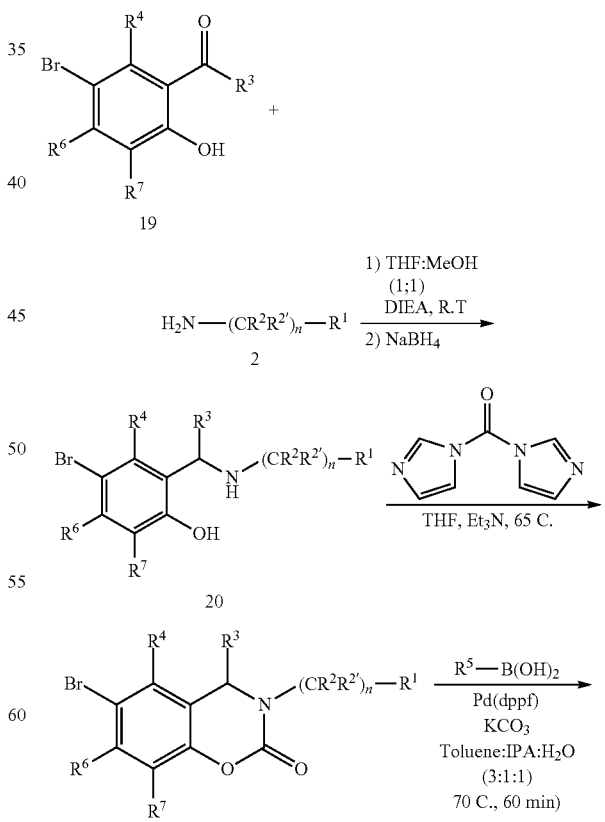

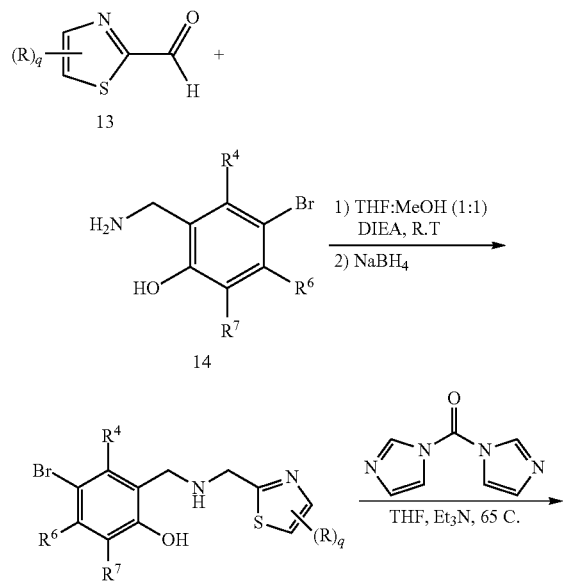

-continued

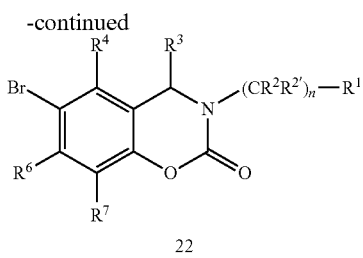

22

For example, scheme 4 shows the formation of compound (22), a compound Formula (I) starting with the ketone (19).

The ketone (19) is reductively aminated with the amine (2) to produce the coupled secondary amine (19) following procedures described previously. The amine (19) is carbonylated to form the carbamate (20). The carbamate (20) is coupled with an $R^5$ group introduced as the boronic acid or ester to afford the compound (22).

Compounds of formula (I) wherein $R^6$ combines with the phenyl ring of $R^5$ to form a tetracyclic ring optionally substituted with 1 or 2 groups may be prepared following the procedure of Scheme 5 below or modifications thereof known to one of skill in the art.

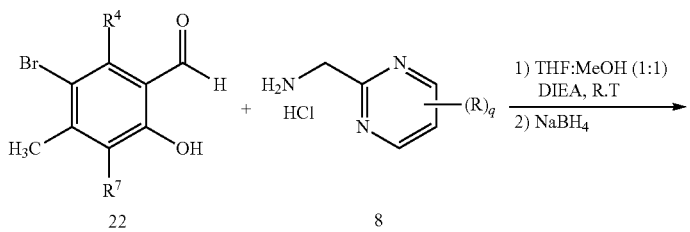

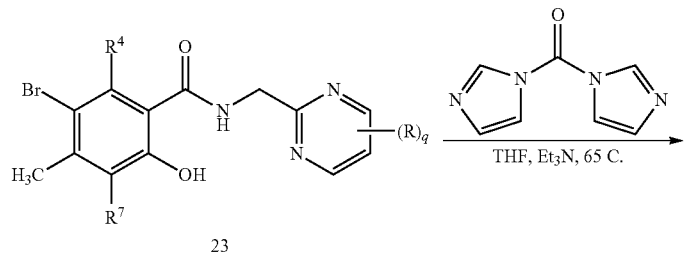

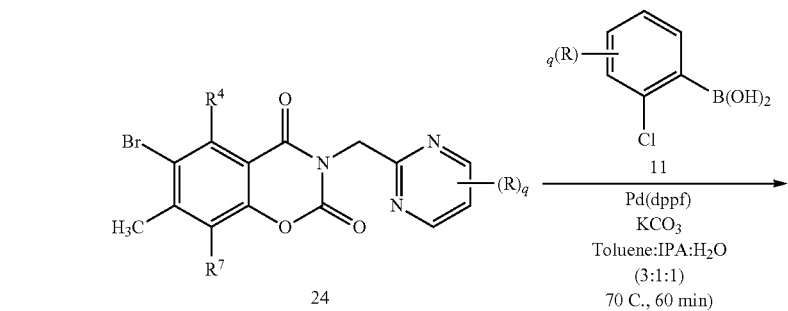

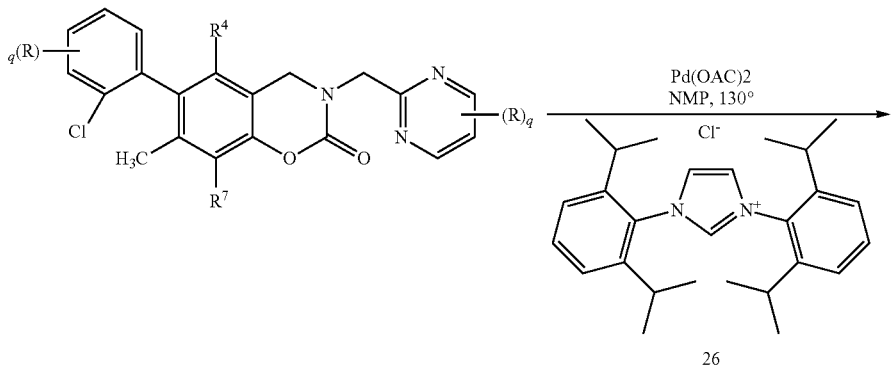

-continued

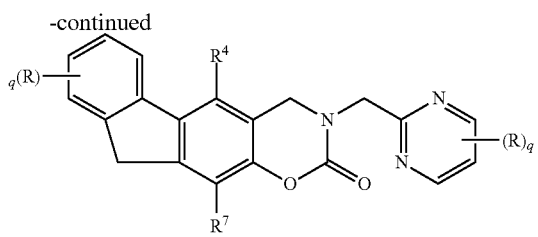

27

R is an optional substitutent as disclosed herein and q is 1, 2 or 3.

As shown in Scheme 5, an appropriately substituted salicyladehyde derivative having an alkyl e.g. methyl substituent on the $R^6$ position of compound formula (I) may be reacted with the amine (8) under reductive amination conditions to produce compound (23). Compound (23) is then cyclized to form the carbamate (24) using carbonyl insertion procedures described herein. The carbamate (24) is then coupled to a boronic acid source having an appropriately substituted leaving group, e.g. halogen, to form the intermediate (25) using previously described Suzuki coupling procedures. The coupled product (25) is then cyclized via palladium catalyzed activation of the benzylic C—H bond to the tetracyclic ring product (27) using appropriate ligands (e.g. 1,3-bis(2,6-diisopropylphenyl)-1H-imidazol-3-ium chloride) and reaction conditions as disclosed herein or known to one of skill in the art. See for example, Tao, TinWu et al., Synthesized of methylene-bridge Polyarenes through Palladium Catalyzed Activation of Benzylic Carbon-Hydrogen Bond, *Adv. Synth. Catal.* 2010, 352, 3267-3274. In the above provided schemes, it will also be appreciated that the reactions may result in the production of a number of isomeric products any or all of which may be isolated and purified using conventional techniques.

EXAMPLES

The following examples are included to demonstrate embodiments of the disclosure. It should be appreciated by those of skill in the art that the techniques disclosed in the examples which follow represent techniques discovered by the inventors to function well in the practice of the disclosure, and thus can be considered to constitute preferred modes for its practice. However, those of skill in the art should, in light of the present disclosure, appreciate that changes can be made in the specific embodiments which are disclosed and still obtain a like or similar result without departing from the spirit and scope of the disclosure.

LIST OF ABBREVIATIONS AND ACRONYMS

Abbreviation Meaning
° C. Degree Celsius
anal Analytical
ATP Adenosine-5'-triphosphate
ATX II Anemonia sulcata toxin
ACN Acetonitrile
CHO Chinese hamster ovary
conc. Concentrated
d Doublet
DABCO 1,4-Diazabicyclo[2.2.2]octane
dd Doublet of doublets
DCM Dichloromethane
DIPEA N,N-diisopropylethylamine
DMF Dimethylformamide
DMSO Dimethylsulfoxide
dppf 1,1'-Bis(diphenylphosphino)ferrocene
EA Ethyl alcohol
ECF Extracellular fluid
EDTA Ethylenediaminetetraacetic acid
EGTA Ethylene glycol tetraacetic acid
equiv/eq Equivalents
ESI Electrospray ionization
Ac Acetate
Et Ethyl
g Grams
HEPES (4-(2-Hydroxyethyl)-1-piperazineethanesulfonic acid)
HATU 2-(7-Aza-1H-Benzotriazole-1-yl)-1,1,3,3-tetramethyluronium hexafluorophosphate
hERG human Ether-à-go-go Related Gene
HPLC High-performance liquid chromatography
h Hours
Hz Hertz
$IC_{50}$ The half maximal inhibitory concentration
IMR-32 Human neuroblastoma cell line
J Coupling constant
Kg Kilogram
kHz Kilohertz
LCMS/LC-MS Liquid chromatography-mass spectrometry
M Molar
m multiplet
m/z mass-to-charge ratio
M+ Mass peak
M+H Mass peak plus hydrogen
Me Methyl
mg Milligram
MHz Megahertz
min/m Minute
ml/mL Milliliter
mM Millimolar
mmol Millimole
nmol Nanomole
mOsmol Milliosmole
MRM Magnetic Resonance Microscopy
MS Mass spectroscopy
ms Millisecond
mV Millivolt
mw Microwave
N Normal
mol Mole
NMR Nuclear magnetic resonance
pA Picoamps
Ph Phenyl
prep Preparative
q.s. Quantity sufficient to achieve a stated function Rf Retention factor
RT/rt Room temperature
s Second
s Singlet
SEM Standard error of the mean
t Triplet
TB Tonic Block
TEA Triethylamine
TFA Trifluoroacetic acid
THF Tetrahydrofuran
TLC Thin layer chromatography
TTX Tetrodotoxin
UDB Use Dependent Block
WT Wild type
δ Chemical shift
μg Microgram
μL/μl Microliter
μM Micromolar
μm Micrometer
μmol Micromole

EXAMPLES

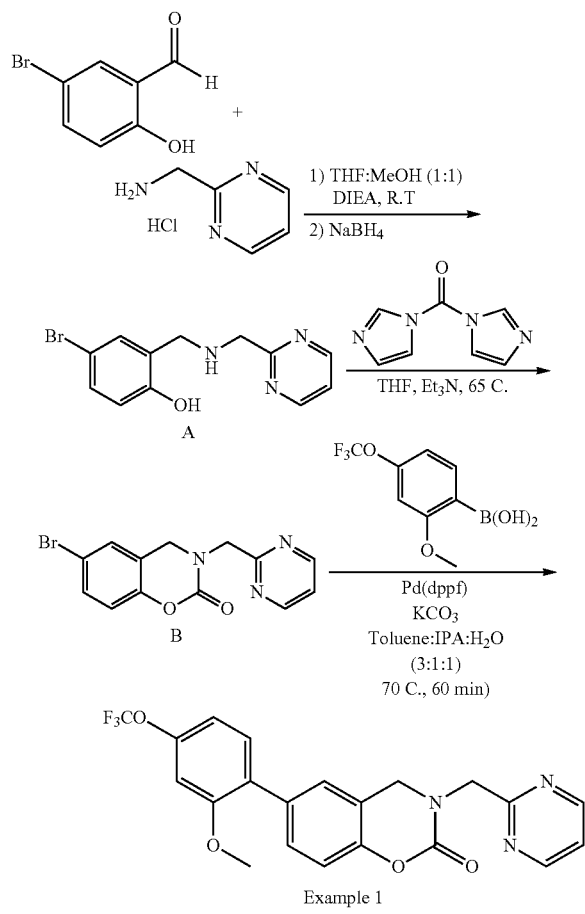

Scheme 2

Example 1

6-(2-methoxy-4-(trifluoromethoxy)phenyl)-3-(pyrimidin-2-ylmethyl)-3,4-dihydro-2H-benzo[e][1,3]oxazin-2-one

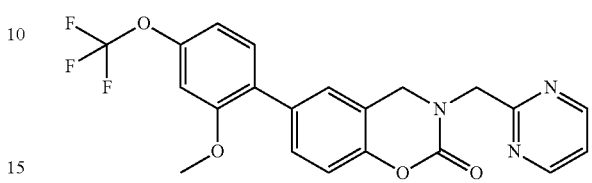

5-bromosalicylaldehyde (2.49 mmol) and 2-aminomethylpyrimidine HCl (3.73 mmol) were combined in THF:MeOH (20:2 mL) mixture followed by addition of N,N-diisopropylethylamine (5-7 mmol). The mixture was stirred under $N_2$ at RT for several hours. After the reaction was complete or substantially complete, 1 equiv. of $NaBH_4$ was added and the mixture was stirred at room temperature overnight. The excess hydride was quenched with 1N HCl. The mixture was concentrated to remove most of organic solvents. Water was added and the organic phase was extracted with DCM. The organic phase was concentrated to give A.

A (2.49 mmol) was dissolved in THF (50 mL) followed by addition of carbonyldiimidazole (CDI) (3.73 mmol) and triethylamine (2 mL). The resulting mixture was refluxed for 2-4 hours. LCMS showed complete conversion to desired product B. The reaction mixture was concentrated and dissolved in DCM. The concentrate was washed with 1N HCl. Organic solvent was removed and the residue was used in next step without further purification.

B (0.625 mmol), (2-methoxy-4-(trifluoromethoxy)phenyl)boronic acid (0.75 mmol), 1,1'-bis(diphenylphosphino)ferrocene-palladium(II)dichloride dichloromethane complex [Pd(dppf)$CH_2Cl_2$] (0.031 mmol), and potassium carbonate (1.25 mmol) were combined with Toluene (3 ml), 2-propanol (1 ml), and water (1 ml) in a microwave reaction tube (round 2-5 mL size). The biphasic reaction mixture was heated at 70 C for 1 hr. LCMS showed complete conversion to desired product. The reaction mixture was filtered through a plug of celite with ethyl acetate. The filtrate was concentrated and purified by preparative TLC (5% MeOH:$CH_2Cl_2$) followed by preparative HPLC to give the compound of Example 1.

m/z (ESI)=432 [M+H]$^+$.

$^1$H NMR (400 MHz, DMSO-d6) δ 8.82 (d, J=4.9 Hz, 2H), 7.53-7.28 (m, 4H), 7.20-7.08 (m, 2H), 7.02 (dd, J=8.5, 1.2 Hz, 1H), 4.81 (s, 2H), 4.74 (s, 2H), 3.81 (s, 3H).

Procedures similar to preparing the compound of Example 1 were employed for the following example compounds. One of ordinary skill in the art is aware to use the analogous starting materials necessary to introduce the variations corresponding to the groups in the compound of example 1 to obtain the desired product. For example, an appropriately substituted 5-bromosalicylaldehyde may be used to introduce substituents on the phenyl group of the benzoisoxazinone core. Similarly, an appropriately optionally substituted amine in place of 2-aminomethyl pyridine is employed to achieve the desired —(CR$^2$R$^{2'}$)$_n$—R$^1$ group, just as an appropriately substituted boronic acid reagent or analog is employed to achieve desired substituent R$^5$ of formula I.

Example 2

3-(pyridin-4-ylmethyl)-6-(4-(trifluoromethyl)phenyl)-3,4-dihydro-2H-benzo[e][1,3]oxazin-2-one

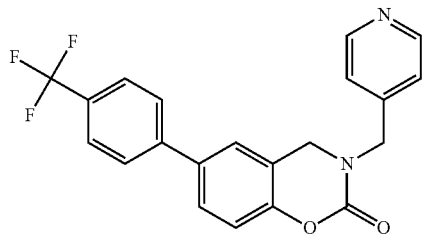 [SMILES: O=C1Oc2ccc(-c3ccc(C(F)(F)F)cc3)cc2CN1Cc1ccncc1]

m/z (ESI)=385.1 [M+H]+.
1H NMR (400 MHz, DMSO-d6) δ 8.72-8.59 (m, 2H), 7.95-7.75 (m, 4H), 7.70 (dd, J=8.5, 2.3 Hz, 1H), 7.64 (d, J=2.2 Hz, 1H), 7.58 (d, J=5.6 Hz, 2H), 7.21 (d, J=8.5 Hz, 1H), 4.75 (s, 2H), 4.62 (s, 2H).

Example 3

3-(pyrimidin-2-ylmethyl)-6-(4-(trifluoromethoxy)phenyl)-3,4-dihydro-2H-benzo[e][1,3]oxazin-2-one

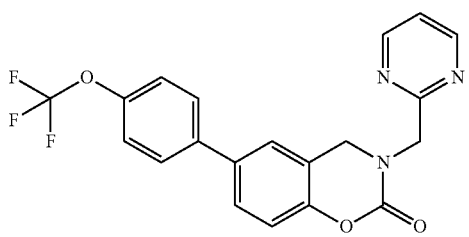 [SMILES: O=C1Oc2ccc(-c3ccc(OC(F)(F)F)cc3)cc2CN1Cc1ncccn1]

m/z (ESI)=402 [M+H]+.
1H NMR (400 MHz, DMSO-d6) δ 8.80 (d, J=4.9 Hz, 2H), 7.88-7.68 (m, 2H), 7.70-7.50 (m, 2H), 7.51-7.38 (m, 3H), 7.17 (d, J=8.5 Hz, 1H), 4.81 (s, 2H), 4.75 (s, 2H).

Example 4

3-(pyrimidin-2-ylmethyl)-6-(4-(trifluoromethyl)phenyl)-3,4-dihydro-2H-benzo[e][1,3]oxazin-2-one

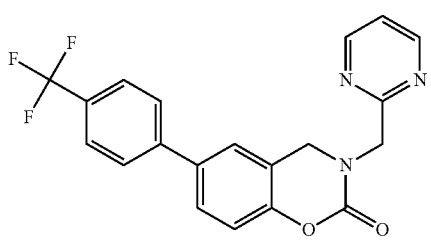 [SMILES: O=C1Oc2ccc(-c3ccc(C(F)(F)F)cc3)cc2CN1Cc1ncccn1]

m/z (ESI)=386 [M+H]+.
1H NMR (400 MHz, DMSO-d6) δ 8.80 (d, J=4.9 Hz, 2H), 7.87 (d, J=8.3 Hz, 2H), 7.80 (d, J=8.4 Hz, 2H), 7.76-7.61 (m, 2H), 7.44 (t, J=4.9 Hz, 1H), 7.20 (d, J=8.5 Hz, 1H), 4.81 (s, 2H), 4.77 (s, 2H).

Example 5

6-(3-methyl-4-(trifluoromethoxy)phenyl)-3-(pyrimidin-2-ylmethyl)-3,4-dihydro-2H-benzo[e][1,3]oxazin-2-one

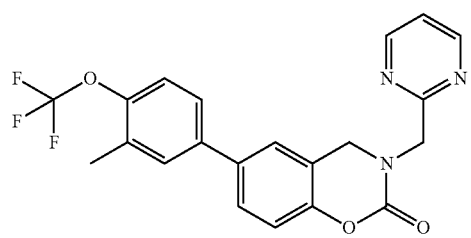 [SMILES: Cc1cc(-c2ccc3c(c2)CN(Cc2ncccn2)C(=O)O3)ccc1OC(F)(F)F]

m/z (ESI)=416.1 [M+H].
1H NMR (400 MHz, DMSO-d6) δ 8.81 (d, J=4.9 Hz, 2H), 7.73-7.51 (m, 4H), 7.51-7.33 (m, 2H), 7.18 (d, J=8.5 Hz, 1H), 4.82 (s, 2H), 4.76 (s, 2H), 2.34 (s, 3H).

Example 6

6-(4-chloro-3-fluorophenyl)-3-(pyrimidin-2-ylmethyl)-3,4-dihydro-2H-benzo[e][1,3]oxazin-2-one

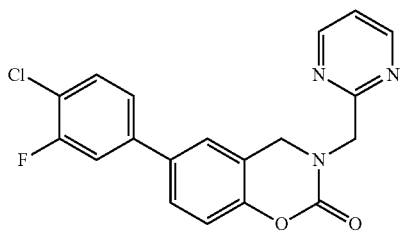 [SMILES: O=C1Oc2ccc(-c3ccc(Cl)c(F)c3)cc2CN1Cc1ncccn1]

m/z (ESI)=370.0 [M+H]+.
1H NMR (400 MHz, DMSO-d6) δ 8.81 (d, J=4.9 Hz, 2H), 7.81-7.61 (m, 4H), 7.60-7.48 (m, 1H), 7.45 (t, J=4.9 Hz, 1H), 7.18 (d, J=8.5 Hz, 1H), 4.82 (s, 2H), 4.76 (s, 2H).

Example 7

6-(2-fluoro-4-(trifluoromethoxy)phenyl)-3-(pyrimidin-2-ylmethyl)-3,4-dihydro-2H-benzo[e][1,3]oxazin-2-one

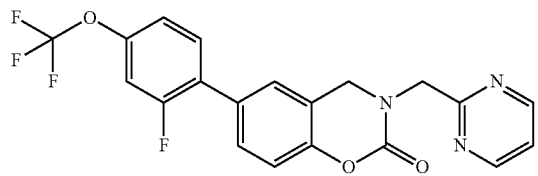 [SMILES: O=C1Oc2ccc(-c3ccc(OC(F)(F)F)cc3F)cc2CN1Cc1ncccn1]

m/z (ESI)=420.0 [M+H]+.
1H NMR (400 MHz, DMSO-d6) δ 8.81 (d, J=4.9 Hz, 2H), 7.67 (t, J=8.8 Hz, 1H), 7.62-7.40 (m, 4H), 7.40-7.30 (m, 1H), 7.21 (d, J=8.5 Hz, 1H), 4.82 (s, 2H), 4.76 (s, 2H).

Example 8

6-(2-methyl-4-(trifluoromethoxy)phenyl)-3-(pyrimidin-2-ylmethyl)-3,4-dihydro-2H-benzo[e][1,3]oxazin-2-one

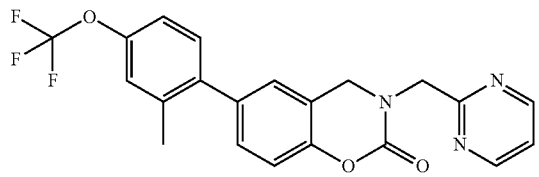 [SMILES: Cc1cc(OC(F)(F)F)ccc1-c1ccc2c(c1)CN(Cc1ncccn1)C(=O)O2]

m/z (ESI)=416.1 [M+H]⁺.

¹H NMR (400 MHz, DMSO-d₆) δ 8.81 (d, J=4.9 Hz, 2H), 7.45 (t, J=4.9 Hz, 1H), 7.38-7.28 (m, 3H), 7.26 (d, 1=2.1 Hz, 2H), 7.16 (d, J=8.4 Hz, 1H), 4.81 (s, 2H), 4.74 (s, 2H), 2.27 (s, 3H).

Example 9

6-(2-methoxy-4-(trifluoromethoxy)phenyl)-3-(pyrimidin-2-ylmethyl)-3,4-dihydro-2H-benzo[e][1,3]oxazin-2-one

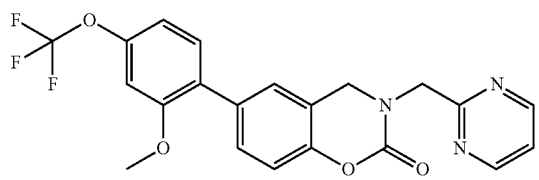 [SMILES: COc1cc(OC(F)(F)F)ccc1-c1ccc2c(c1)CN(Cc1ncccn1)C(=O)O2]

m/z (ESI)=432.1 [M+H]⁺.

¹H NMR (400 MHz, DMSO-d₆) δ 8.86-8.74 (m, 2H), 7.50-7.29 (m, 4H), 7.18-7.07 (m, 2H), 7.02 (dt, J=8.6, 1.2 Hz, 1H), 4.81 (s, 2H), 4.73 (s, 2H), 3.80 (s, 3H).

Example 10

6-(3-fluoro-4-(trifluoromethoxy)phenyl)-3-(pyrimidin-2-ylmethyl)-3,4-dihydro-2H-benzo[e][1,3]oxazin-2-one

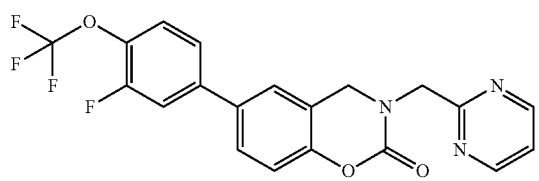 [SMILES: O=C1Oc2ccc(-c3ccc(OC(F)(F)F)c(F)c3)cc2CN1Cc1ncccn1]

m/z (ESI)=420.0 [M+H]⁺.

¹H NMR (400 MHz, DMSO-d₆) δ 8.81 (d, J=4.9 Hz, 2H), 7.84 (dd, J=11.9, 2.0 Hz, 1H), 7.76-7.55 (m, 4H), 7.45 (t, J=4.9 Hz, 1H), 7.20 (d, J=8.5 Hz, 1H), 4.82 (s, 2H), 4.76 (s, 2H).

Example 11

6-(4-chloro-3-fluorophenyl)-4-methyl-3-(pyrimidin-2-ylmethyl)-3,4-dihydro-2H-benzo[e][1,3]oxazin-2-one

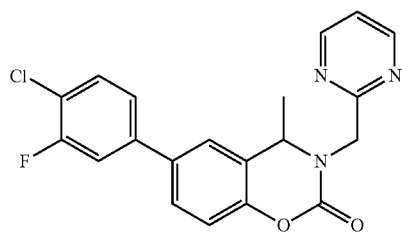 [SMILES: CC1c2cc(-c3ccc(Cl)c(F)c3)ccc2OC(=O)N1Cc1ncccn1]

m/z (ESI)=384.0 [M+H]⁺.

1H NMR (400 MHz, DMSO-d6) δ 8.77 (d, J=4.9 Hz, 2H), 7.80 (dd, J=11.1, 2.1 Hz, 1H), 7.76-7.62 (m, 3H), 7.62-7.52 (m, 1H), 7.41 (t, J=4.9 Hz, 1H), 7.19 (d, J=9.2 Hz, 1H), 5.01 (d, J=17.2 Hz, 1H), 4.80 (d, J=6.5 Hz, 1H), 4.71 (d, J=17.2 Hz, 1H), 1.53 (d, J=6.5 Hz, 3H).

Example 12

3-((5-methylpyrimidin-2-yl)methyl)-6-(4-(trifluoromethoxy)phenyl)-3,4-dihydro-2H-benzo[e][1,3]oxazin-2-one

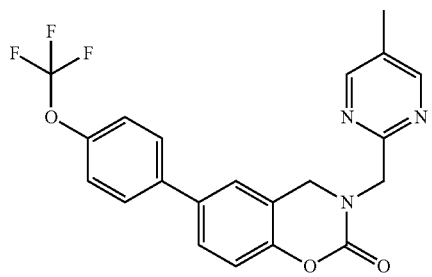 [SMILES: Cc1cnc(CN2Cc3cc(-c4ccc(OC(F)(F)F)cc4)ccc3OC2=O)nc1]

m/z (ESI)=416.1 [M+H].

1H NMR (400 MHz, DMSO-d6) δ 8.65 (d, J=0.9 Hz, 2H), 7.83-7.70 (m, 2H), 7.71-7.52 (m, 2H), 7.51-7.38 (m, 2H), 7.18 (d, J=8.5 Hz, 1H), 4.75 (s, 2H), 4.72 (s, 2H), 2.27 (s, 3H).

Example 13

3-((5-methylpyrimidin-2-yl)methyl)-6-(4-(trifluoromethyl)phenyl)-3,4-dihydro-2H-benzo[e][1,3]oxazin-2-one

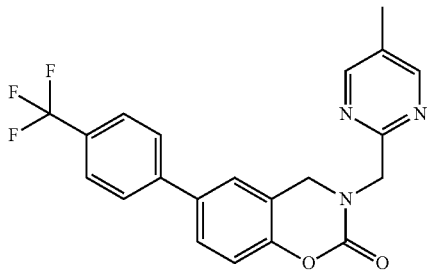 [SMILES: Cc1cnc(CN2Cc3cc(-c4ccc(C(F)(F)F)cc4)ccc3OC2=O)nc1]

m/z (ESI)=400.1 [M+H]$^+$.
1H NMR (400 MHz, DMSO-d6) δ 8.65 (d, J=0.9 Hz, 2H), 7.94-7.76 (m, 4H), 7.76-7.61 (m, 2H), 7.21 (d, J=8.5 Hz, 1H), 4.76 (s, 2H), 4.74 (s, 2H), 2.27 (s, 3H).

Example 14

6-(2-fluoro-4-(trifluoromethoxy)phenyl)-3-((5-methylpyrimidin-2-yl)methyl)-3,4-dihydro-2H-benzo[e][1,3]oxazin-2-one

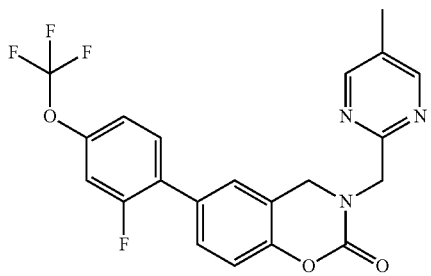 [SMILES: Cc1cnc(CN2Cc3cc(-c4ccc(OC(F)(F)F)cc4F)ccc3OC2=O)nc1]

m/z (ESI)=434.1 [M+H]$^+$.
1H NMR (400 MHz, DMSO-d6) δ 8.65 (d, J=0.9 Hz, 2H), 7.67 (t, J=8.8 Hz, 1H), 7.59-7.41 (m, 3H), 7.41-7.29 (m, 1H), 7.20 (d, J=8.5 Hz, 1H), 4.75 (s, 2H), 4.72 (s, 2H), 2.27 (s, 3H).

Example 15

3-((2-methylpyrimidin-4-yl)methyl)-6-(4-(trifluoromethoxy)phenyl)-3,4-dihydro-2H-benzo[e][1,3]oxazin-2-one

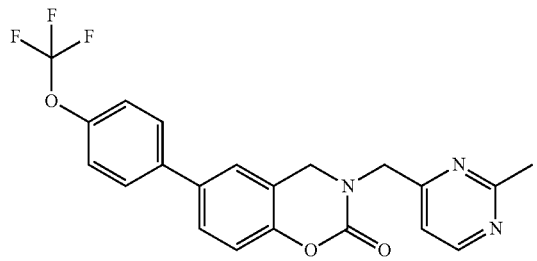 [SMILES: Cc1nccc(CN2Cc3cc(-c4ccc(OC(F)(F)F)cc4)ccc3OC2=O)n1]

m/z (ESI)=416.1 [M+H]$^+$.
1H NMR (400 MHz, DMSO-d6) δ 8.66 (d, J=5.2 Hz, 1H), 7.83-7.71 (m, 2H), 7.71-7.53 (m, 2H), 7.52-7.40 (m, 2H), 7.34 (d, J=5.2 Hz, 1H), 7.19 (d, J=8.5 Hz, 1H), 4.69 (s, 2H), 4.67 (s, 2H), 2.60 (s, 3H).

Example 16

3-(2-(pyrimidin-2-yl)ethyl)-6-(4-(trifluoromethoxy)phenyl)-3,4-dihydro-2H-benzo[e][1,3]oxazin-2-one

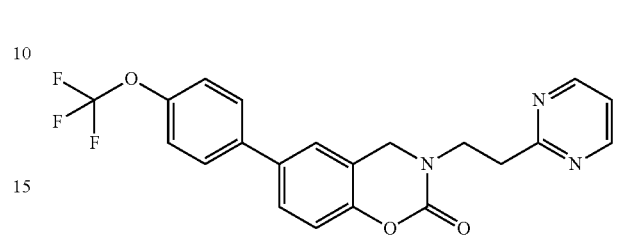

m/z (ESI)=416.1 [M+H]$^+$.
1H NMR (400 MHz, DMSO-d6) δ 8.74 (d, J=4.9 Hz, 2H), 7.84-7.70 (m, 2H), 7.66-7.52 (m, 2H), 7.51-7.40 (m, 2H), 7.37 (t, J=4.9 Hz, 1H), 7.12 (d, J=8.4 Hz, 1H), 4.63 (s, 2H), 3.85 (t, J=7.3 Hz, 2H), 3.25 (t, J=7.3 Hz, 2H).

Example 17

3-(2-(pyrimidin-2-yl)ethyl)-6-(4-(trifluoromethyl)phenyl)-3,4-dihydro-2H-benzo[e][1,3]oxazin-2-one

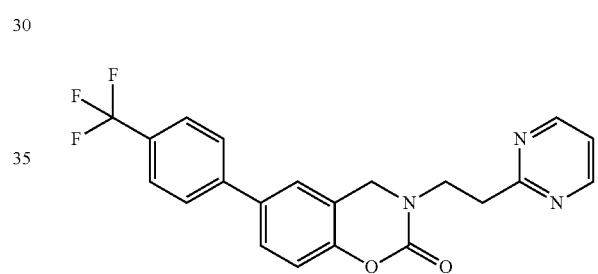

m/z (ESI)=400.2 [M+H]$^+$.
1H NMR (400 MHz, DMSO-d6) δ 8.74 (d, J=4.9 Hz, 1H), 7.98-7.73 (m, 4H), 7.75-7.55 (m, 2H), 7.37 (t, J=4.9 Hz, 1H), 7.15 (d, J=8.4 Hz, 1H), 4.65 (s, 2H), 3.85 (t, J=7.3 Hz, 2H), 3.25 (t, J=7.3 Hz, 2H).

Example 18

6-(2-methoxy-4-(trifluoromethoxy)phenyl)-3-(2-(pyrimidin-2-yl)ethyl)-3,4-dihydro-2H-benzo[e][1,3]oxazin-2-one

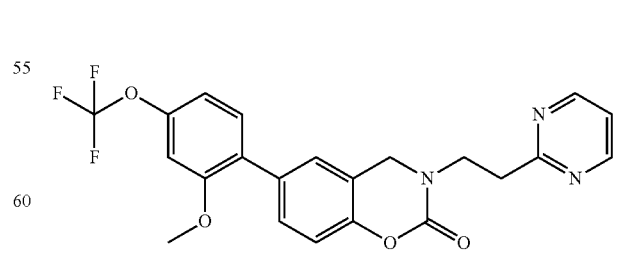

m/z (ESI)=446.1 [M+H]$^+$.
1H NMR (400 MHz, DMSO-d6) δ 8.73 (m, 2H), 7.42-7.30 (m, 3H), 7.21-7.08 (m, 4H), 4.60 (s, 2H), 3.90-3.75 (m, 5H), 3.24 (m, 2H).

Example 19

6-(2-propoxy-4-(trifluoromethyl)phenyl)-3-(2-(pyrimidin-2-yl)ethyl)-3,4-dihydro-2H-benzo[e][1,3]oxazin-2-one

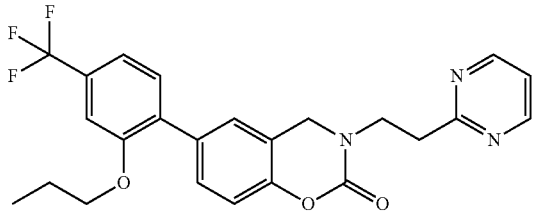 [SMILES: CCCOc1cc(C(F)(F)F)ccc1-c1ccc2c(c1)CN(CCc1ncccn1)C(=O)O2]

m/z (ESI)=458.1 [M+H]⁺.

1H NMR (400 MHz, DMSO-d6) δ 8.74 (d, J=4.9 Hz, 2H), 7.57-7.43 (m, 2H), 7.44-7.31 (m, 4H), 7.08 (d, J=8.5 Hz, 1H), 4.60 (s, 2H), 4.05 (t, J=6.3 Hz, 2H), 3.84 (t, J=7.3 Hz, 2H), 3.24 (t, J=7.3 Hz, 2H), 1.68 (m, 2H), 0.93 (t, J=7.4 Hz, 3H).

Example 20

3-(pyridin-2-ylmethyl)-6-(4-(trifluoromethoxy)phenyl)-3,4-dihydro-2H-benzo[e][1,3]oxazin-2-one

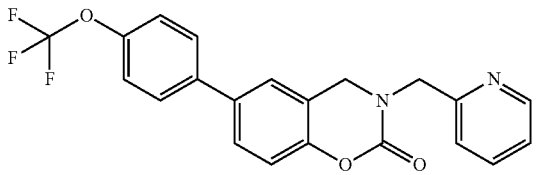 [SMILES: O=C1Oc2ccc(-c3ccc(OC(F)(F)F)cc3)cc2CN1Cc1ccccn1]

m/z (ESI)=401.2 [M+H]⁺.

1H NMR (400 MHz, Chloroform-d) δ 8.78-8.71 (m, 1H), 8.08 (m, 1H), 7.86 (d, J=7.9 Hz, 1H), 7.63-7.55 (m, 1H), 7.56-7.48 (m, 2H), 7.46 (dd, J=8.5, 2.2 Hz, 1H), 7.31-7.23 (m, 3H), 7.12 (d, J=8.5 Hz, 1H), 5.00 (s, 2H), 4.73 (s, 2H).

Example 21

6-(2-fluoro-4-(trifluoromethoxy)phenyl)-3-(pyridin-2-ylmethyl)-3,4-dihydro-2H-benzo[e][1,3]oxazin-2-one

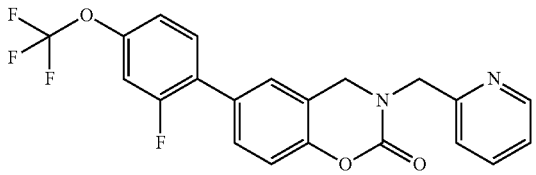

m/z (ESI)=419.2 [M+11]⁺.

1H NMR (400 MHz, Chloroform-d) δ 8.76 (d, J=5.4 Hz, 1H), 8.13-8.05 (m, 1H), 7.86 (d, J=8.0 Hz, 1H), 7.62-7.56 (m, 1H), 7.47-7.35 (m, 2H), 7.26 (s, 1H), 7.17-7.01 (m, 3H), 5.00 (s, 2H), 4.72 (s, 2H).

Example 22

6-(2-methoxy-4-(trifluoromethoxy)phenyl)-3-(pyridin-2-ylmethyl)-3,4-dihydro-2H-benzo[e][1,3]oxazin-2-one

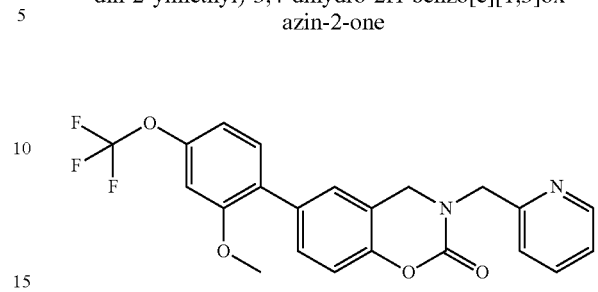

m/z (ESI)=431.2 [M+H]⁺.

1H NMR (400 MHz, Chloroform-d) δ 8.82-8.73 (m, 1H), 8.20-8.08 (m, 1H), 7.96-7.86 (m, 1H), 7.70-7.59 (m, 1H), 7.38 (dd, J=8.4, 2.0 Hz, 1H), 7.24 (m, 1H), 7.09 (d, J=8.5 Hz, 1H), 6.93-6.85 (m, 1H), 6.81 (m, 1H), 5.03 (s, 2H), 4.70 (s, 2H), 3.81 (s, 3H).

Example 23

6-(2-methyl-4-(trifluoromethoxy)phenyl)-3-(pyridin-2-ylmethyl)-3,4-dihydro-2H-benzo[e][1,3]oxazin-2-one

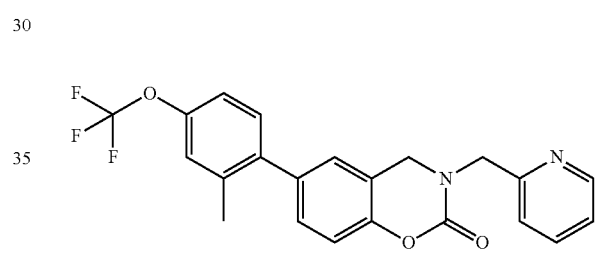

m/z (ESI)=415.2 [M+H]⁺.

1H NMR (400 MHz, Chloroform-d) δ 8.84-8.72 (m, 1H), 8.14 (m, 1H), 7.94 (m, 1H), 7.72-7.59 (m, 1H), 7.24-6.97 (m, 6H), 5.03 (s, 2H), 4.73 (s, 2H), 2.24 (s, 3H).

Example 24

3-(pyridin-2-ylmethyl)-6-(4-(trifluoromethyl)phenyl)-3,4-dihydro-2H-benzo[e][1,3]oxazin-2-one

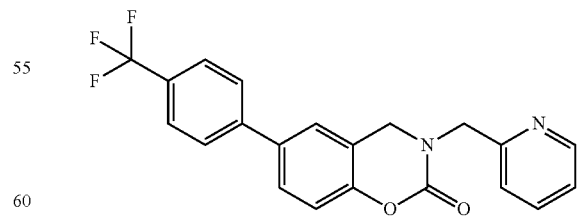

m/z (ESI)=385.2 [M+H]⁺.

1H NMR (400 MHz, Chloroform-d) δ 8.79 (d, J=5.3 Hz, 1H), 8.22-8.08 (m, 1H), 7.98-7.88 (m, 1H), 7.75-7.56 (m, 5H), 7.51 (dd, J=8.5, 2.0 Hz, 1H), 7.33 (d, J=2.1 Hz, 1H), 7.14 (d, J=8.5 Hz, 1H), 5.03 (s, 2H), 4.76 (s, 2H).

Example 25

6-(2-isopropoxy-4-(trifluoromethyl)phenyl)-3-(pyrimidin-2-ylmethyl)-3,4-dihydro-2H-benzo[e][1,3]oxazin-2-one

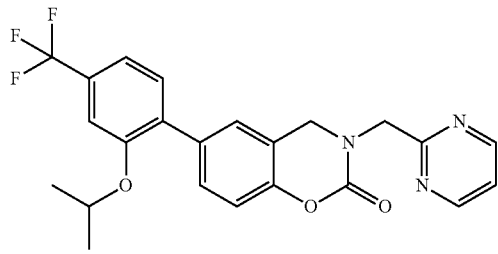 [SMILES: CC(C)Oc1cc(C(F)(F)F)ccc1-c1ccc2c(c1)CN(Cc1ncccn1)C(=O)O2]

m/z (EST)=444.1 [M+H]⁺.
1H NMR (400 MHz, DMSO-d6) δ 8.81 (d, J=4.9 Hz, 2H), 7.59-7.26 (m, 6H), 7.15 (d, J=8.5 Hz, 1H), 4.80 (s, 2H), 4.79-4.66 (m, 3H), 1.23 (d, J=6.0 Hz, 5H).

Example 26

6-(2,2-difluorobenzo[d][1,3]dioxol-5-yl)-3-(pyrimidin-2-ylmethyl)-3,4-dihydro-2H-benzo[e][1,3]oxazin-2-one

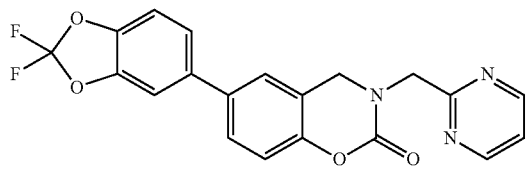 [SMILES: O=C1Oc2ccc(-c3ccc4c(c3)OC(F)(F)O4)cc2CN1Cc1ncccn1]

m/z (ESI)=498.1 [M+H]⁺.
1H NMR (400 MHz, DMSO-d6) δ 8.81 (d, J=4.9 Hz, 2H), 7.73 (m, 1H), 7.70-7.52 (m, 2H), 7.52-7.38 (m, 3H), 7.17 (d, J=8.5 Hz, 1H), 4.82 (s, 2H), 4.76 (s, 2H).

Example 27

6-(2-propoxy-4-(trifluoromethyl)phenyl)-3-(pyrimidin-2-ylmethyl)-3,4-dihydro-2H-benzo[e][1,3]oxazin-2-one

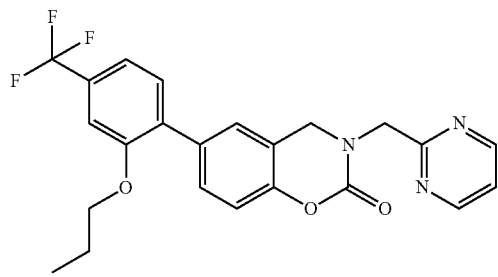 [SMILES: CCCOc1cc(C(F)(F)F)ccc1-c1ccc2c(c1)CN(Cc1ncccn1)C(=O)O2]

m/z (ESI)=444.1 [M+H]⁺.
1H NMR (400 MHz, DMSO-d6) δ 8.81 (d, J=4.9 Hz, 2H), 7.60-7.28 (m, 6H), 7.15 (d, J=8.5 Hz, 1H), 4.82 (s, 2H), 4.74 (s, 2H), 4.05 (t, J=6.3 Hz, 2H), 1.68 (m, 2H), 0.92 (t, J=7.4 Hz, 3H).

Example 28

6-(2-propoxy-4-(trifluoromethoxy)phenyl)-3-(pyrimidin-2-ylmethyl)-3,4-dihydro-2H-benzo[e][1,3]oxazin-2-one

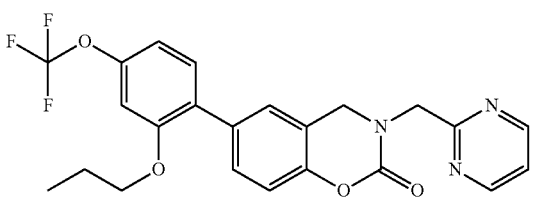 [SMILES: CCCOc1cc(OC(F)(F)F)ccc1-c1ccc2c(c1)CN(Cc1ncccn1)C(=O)O2]

m/z (ESI)=460.1 [M+H]⁺.
1H NMR (400 MHz, DMSO-d6) δ 8.81 (d, J=4.9 Hz, 2H), 7.54-7.31 (m, 5H), 7.20-7.05 (m, 2H), 7.00 (d, J=8.4 Hz, 1H), 4.81 (s, 2H), 4.73 (s, 2H), 3.99 (t, J=6.3 Hz, 2H), 1.67 (m, 2H), 0.91 (t, J=7.4 Hz, 3H).

Example 29

3-((4-methylpyrimidin-2-yl)methyl)-6-(4-(trifluoromethoxy)phenyl)-3,4-dihydro-2H-benzo[e][1,3]oxazin-2-one

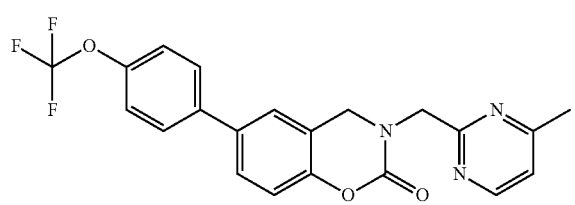 [SMILES: Cc1ccnc(CN2Cc3cc(-c4ccc(OC(F)(F)F)cc4)ccc3OC2=O)n1]

m/z (ESI)=416.1 [M+H]⁺.
1H NMR (400 MHz, DMSO-d6) δ 8.63 (d, J=5.1 Hz, 1H), 7.84-7.72 (m, 2H), 7.70-7.54 (m, 2H), 7.50-7.40 (m, 2H), 7.31 (d, J=5.1 Hz, 1H), 7.18 (d, J=8.5 Hz, 1H), 4.76 (m, 4H), 2.46 (s, 3H).

Example 30

3-((4-methylpyrimidin-2-yl)methyl)-6-(4-(trifluoromethyl)phenyl)-3,4-dihydro-2H-benzo[e][1,3]oxazin-2-one

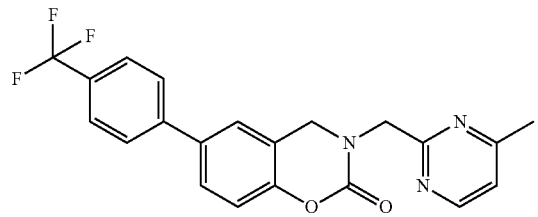 [SMILES: Cc1ccnc(CN2Cc3cc(-c4ccc(C(F)(F)F)cc4)ccc3OC2=O)n1]

m/z (ESI)=400.1 [M+H]⁺.
1H NMR (400 MHz, DMSO-d6) δ 8.63 (d, J=5.1 Hz, 1H), 7.88 (m, 2H), 7.81 (m, 2H), 7.76-7.63 (m, 2H), 7.31 (d, J=5.1 Hz, 1H), 7.22 (d, J=8.5 Hz, 1H), 4.77 (m, 4H), 2.46 (s, 3H).

Example 31

6-(2-methoxy-4-(trifluoromethoxy)phenyl)-3-((4-methylpyrimidin-2-yl)methyl)-3,4-dihydro-2H-benzo[e][1,3]oxazin-2-one

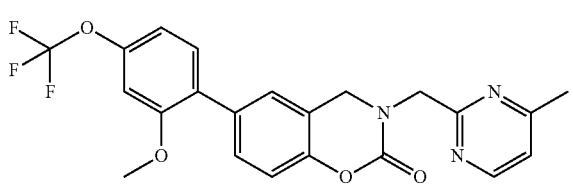 [SMILES: COc1cc(OC(F)(F)F)ccc1-c1ccc2c(c1)CN(Cc1nccc(C)n1)C(=O)O2]

m/z (ESI)=446.1 [M+H]⁺.
1H NMR (400 MHz, DMSO-d6) δ 8.61 (d, J=5.1 Hz, 1H), 7.42-7.36 (m, 2H), 7.34-7.27 (m, 2H), 7.12-7.08 (m, 2H), 7.00 (d, J=7.0 Hz, 1H), 4.72 (m, 4H), 3.79 (s, 3H), 2.44 (s, 3H).

Example 32

6-(2-fluoro-4-(trifluoromethoxy)phenyl)-3-((4-methylpyrimidin-2-yl)methyl)-3,4-dihydro-2H-benzo[e][1,3]oxazin-2-one

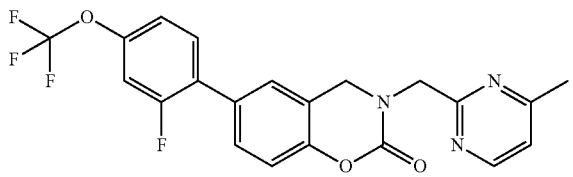 [SMILES: Cc1ccnc(CN2Cc3cc(-c4ccc(OC(F)(F)F)cc4F)ccc3OC2=O)n1]

m/z (ESI)=434.1 [M+H]⁺.
1H NMR (400 MHz, DMSO-d6) δ 8.61 (d, J=5.1 Hz, 1H), 7.65 (m, 1H), 7.57-7.41 (m, 3H), 7.37-7.24 (m, 2H), 7.19 (d, J=8.5 Hz, 1H), 4.74 (m, 4H), 2.44 (s, 3H).

Example 33

6-(2-methyl-4-(trifluoromethoxy)phenyl)-3-((4-methylpyrimidin-2-yl)methyl)-3,4-dihydro-2H-benzo[e][1,3]oxazin-2-one

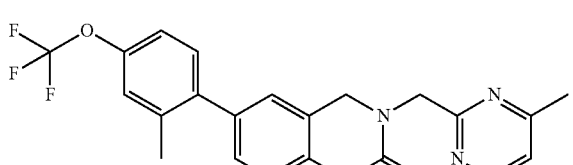

m/z (ESI)=430.1 [M+H]⁺.
1H NMR (400 MHz, DMSO-d6) δ 8.63 (d, J=5.1 Hz, 1H), 7.37-7.20 (m, 6H), 7.15 (d, J=8.4 Hz, 1H), 4.74-4.72 (m, 4H), 2.46 (s, 3H), 2.27 (s, 3H).

Example 34

6-(2-methoxy-4-(trifluoromethyl)phenyl)-3-(pyrimidin-2-ylmethyl)-3,4-dihydro-2H-benzo[e][1,3]oxazin-2-one

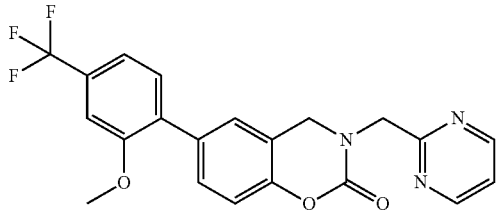 [SMILES: COc1cc(C(F)(F)F)ccc1-c1ccc2c(c1)CN(Cc1ncccn1)C(=O)O2]

m/z (ESI)=416.1 [M+H]⁺.
1H NMR (400 MHz, DMSO-d6) δ 8.80 (d, J=4.9 Hz, 2H), 7.55-7.40 (m, 3H), 7.37-7.36 (m, 3H), 7.13 (d, J=8.4 Hz, 1H), 4.79 (s, 2H), 4.73 (s, 2H), 3.84 (s, 3H).

Example 35

6-(2-ethoxy-4-(trifluoromethyl)phenyl)-3-(pyrimidin-2-ylmethyl)-3,4-dihydro-2H-benzo[e][1,3]oxazin-2-one

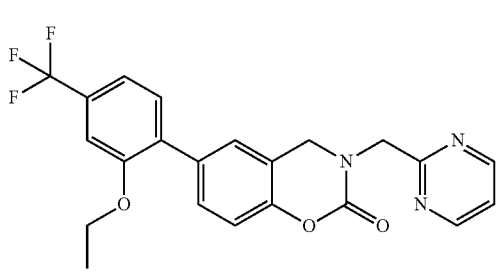 [SMILES: CCOc1cc(C(F)(F)F)ccc1-c1ccc2c(c1)CN(Cc1ncccn1)C(=O)O2]

m/z (ESI)=430.1 [M+H]⁺.
1H NMR (400 MHz, DMSO-d6) δ 8.81 (d, J=4.9 Hz, 2H), 7.51-7.48 (m, 2H), 7.50-7.38 (m, 2H), 7.35-7.33 (m, 2H), 7.15 (d, J=8.5 Hz, 1H), 4.82 (s, 2H), 4.75 (s, 2H), 4.15 (q, J=6.9 Hz, 2H), 1.29 (t, J=6.9 Hz, 3H).

Example 36

6-(2-fluoro-4-(trifluoromethyl)phenyl)-3-(pyrimidin-2-ylmethyl)-3,4-dihydro-2H-benzo[e][1,3]oxazin-2-one

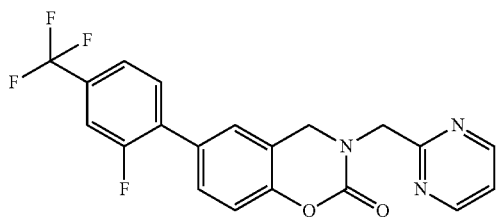 [SMILES: Cc1cc(C(F)(F)F)ccc1-c1ccc2c(c1)CN(Cc1ncccn1)C(=O)O2]

m/z (ESI)=404.1 [M+H]⁺.
1H NMR (400 MHz, DMSO-d6) δ 8.82 (d, J=4.9 Hz, 2H), 7.86-7.73 (m, 2H), 7.69-7.66 (m, 1H), 7.63-7.49 (m, 2H), 7.45-7.42 (m, 1H), 7.24 (d, J=8.5 Hz, 1H), 4.82 (s, 2H), 4.78 (s, 2H).

Example 37

6-(2-methyl-4-(trifluoromethyl)phenyl)-3-(pyrimidin-2-ylmethyl)-3,4-dihydro-2H-benzo[e][1,3]oxazin-2-one

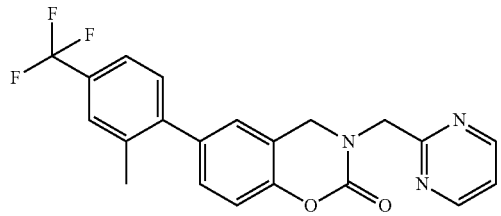

m/z (ESI)=400.1 [M+H]+.

1H NMR (400 MHz, DMSO-d6) δ 8.82 (d, J=4.9 Hz, 2H), 7.69 (d, J=1.9 Hz, 1H), 7.61 (d, J=7.5 Hz, 1H), 7.50-7.40 (m, 2H), 7.35 (dd, J=8.4, 2.1 Hz, 1H), 7.29 (d, J=2.0 Hz, 1H), 7.18 (d, J=8.4 Hz, 1H), 4.82 (s, 2H), 4.76 (s, 2H), 2.32 (s, 3H).

Example 38

3-(pyrimidin-2-ylmethyl)-6-(4-(1-(trifluoromethyl)cyclopropyl)phenyl)-3,4-dihydro-2H-benzo[e][1,3]oxazin-2-one

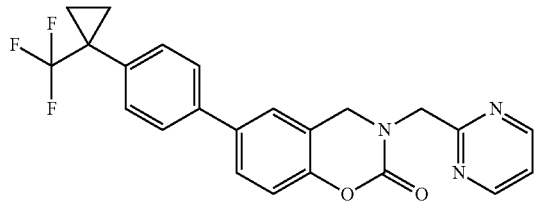 [SMILES: O=C1Oc2ccc(-c3ccc(C4(C(F)(F)F)CC4)cc3)cc2CN1Cc1ncccn1]

m/z (ESI)=426.1 [M+H]+.

1H NMR (400 MHz, DMSO-d6) δ 8.81 (d, J=4.9 Hz, 2H), 7.71-7.49 (m, 6H), 7.45 (s, 1H), 7.17 (d, J=8.5 Hz, 1H), 4.82 (s, 2H), 4.77 (s, 2H), 1.36 (d, J=2.0 Hz, 2H), 1.16 (s, 2H).

Example 39

6-(2-isopropoxy-4-(trifluoromethoxy)phenyl)-3-(pyrimidin-2-ylmethyl)-3,4-dihydro-2H-benzo[e][1,3]oxazin-2-one

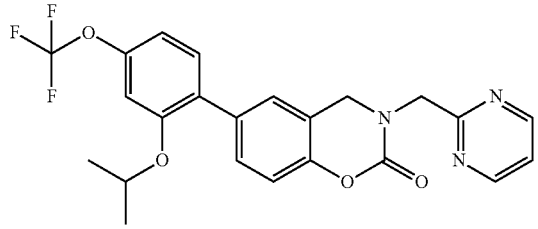 [SMILES: CC(C)Oc1cc(OC(F)(F)F)ccc1-c1ccc2c(c1)CN(Cc1ncccn1)C(=O)O2]

m/z (ESI)=460.2 [M+H]+.

1H NMR (400 MHz, DMSO-d6) δ 8.81 (d, J=4.9 Hz, 2H), 7.54-7.32 (m, 4H), 7.20-7.04 (m, 2H), 7.06-6.93 (m, 1H), 4.81 (s, 2H), 4.78-4.59 (m, 3H), 1.23 (d, J=6.0 Hz, 6H).

Example 40

6-(2-ethoxy-4-(trifluoromethoxy)phenyl)-3-(pyrimidin-2-ylmethyl)-3,4-dihydro-2H-benzo[e][1,3]oxazin-2-one

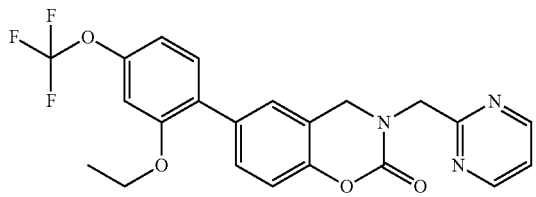 [SMILES: CCOc1cc(OC(F)(F)F)ccc1-c1ccc2c(c1)CN(Cc1ncccn1)C(=O)O2]

m/z (ESI)=446.2 [M+H]+.

1H NMR (400 MHz, DMSO-d6) δ 8.81 (d, J=4.9 Hz, 2H), 7.50-7.35 (m, 4H), 7.15-7.07 (m, 2H), 7.03-6.97 (m, 1H), 4.81 (s, 2H), 4.73 (s, 2H), 4.08 (m, 2H), 1.27 (t, J=6.9 Hz, 3H).

Example 41

6-(2-fluoro-4-(trifluoromethyl)phenyl)-3-((5-methylpyrimidin-2-yl)methyl)-3,4-dihydro-2H-benzo[e][1,3]oxazin-2-one

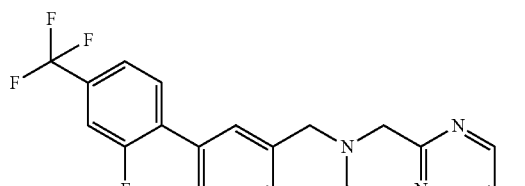

m/z (ESI)=418.1 [M+H]+.

1H NMR (400 MHz, DMSO-d6) δ 8.65 (d, J=1.0 Hz, 2H), 7.88-7.72 (m, 2H), 7.69-7.65 (m, 1H), 7.64-7.46 (m, 2H), 7.23 (d, J=8.5 Hz, 1H), 4.76-4.73 (m, 4H), 2.27 (s, 3H).

Example 42

6-(2-methoxy-4-(trifluoromethyl)phenyl)-3-((5-methylpyrimidin-2-yl)methyl)-3,4-dihydro-2H-benzo[e][1,3]oxazin-2-one

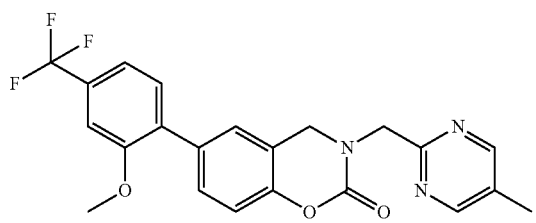 [SMILES: COc1cc(C(F)(F)F)ccc1-c1ccc2c(c1)CN(Cc1ncc(C)cn1)C(=O)O2]

m/z (ESI)=430.1 [M+H]+.

1H NMR (400 MHz, DMSO-d6) δ 8.65 (d, J=0.9 Hz, 2H), 7.49-7.43 (m, 2H), 7.38-7.36 (m, 3H), 7.15 (d, J=8.5 Hz, 1H), 4.77 (s, 2H), 4.72 (s, 2H), 3.86 (s, 3H), 2.27 (s, 3H).

Example 43

6-(2-methyl-4-(trifluoromethyl)phenyl)-3-((5-methylpyrimidin-2-yl)methyl)-3,4-dihydro-2H-benzo[e][1,3]oxazin-2-one

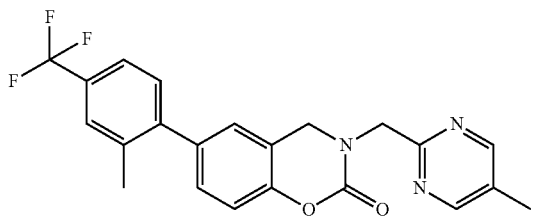 [SMILES: Cc1cnc(CN2Cc3cc(-c4ccc(C(F)(F)F)cc4C)ccc3OC2=O)nc1]

m/z (ESI)=414.1 [M+H].
1H NMR (400 MHz, DMSO-d6) δ 8.65 (d, J=0.9 Hz, 2H), 7.68 (d, J=1.8 Hz, 1H), 7.64-7.55 (m, 1H), 7.42 (d, J=8.0 Hz, 1H), 7.35 (dd, J=8.4, 2.1 Hz, 1H), 7.28 (d, J=2.1 Hz, 1H), 7.18 (d, J=8.4 Hz, 1H), 4.75-4.71 (m, 4H), 2.29 (s, 3H) 2.25 (s, 3H).

Example 44

6-(2-methoxy-4-(trifluoromethyl)phenyl)-3-((6-methylpyridin-2-yl)methyl)-3,4-dihydro-2H-benzo[e][1,3]oxazin-2-one

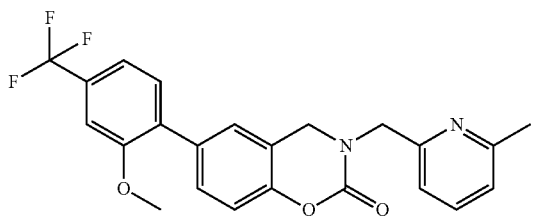 [SMILES: COc1cc(C(F)(F)F)ccc1-c1ccc2c(c1)CN(Cc1cccc(C)n1)C(=O)O2]

m/z (ESI)=429.1 [M+H].
1H NMR (400 MHz, DMSO-d6) δ 7.86-7.80 (m, 1H), 7.56-7.42 (m, 2H), 7.42-7.28 (m, 5H), 7.14 (d, J=8.5 Hz, 1H), 4.72 (s, 2H), 4.67 (s, 2H), 3.85 (s, 3H), 2.53 (s, 3H).

Example 45

6-(2-fluoro-4-(trifluoromethyl)phenyl)-3-((6-methylpyridin-2-yl)methyl)-3,4-dihydro-2H-benzo[e][1,3]oxazin-2-one

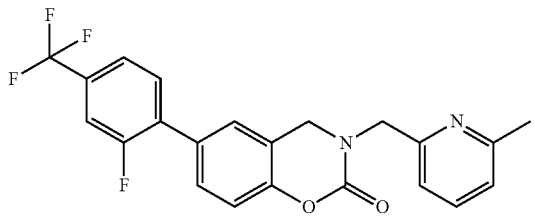 [SMILES: Cc1cccc(CN2Cc3cc(-c4ccc(C(F)(F)F)cc4F)ccc3OC2=O)n1]

m/z (ESI)=417.1 [M+H].
1H NMR (400 MHz, DMSO-d6) δ 7.93-7.64 (m, 4H), 7.63-7.48 (m, 2H), 7.34 (d, J=2.8 Hz, 2H), 7.23 (d, J=8.5 Hz, 1H), 4.71-4.67 (m, 4H), 2.52 (s, 3H).

Example 46

6-(2-methoxy-4-(trifluoromethoxy)phenyl)-3-((6-methylpyridin-2-yl)methyl)-3,4-dihydro-2H-benzo[e][1,3]oxazin-2-one

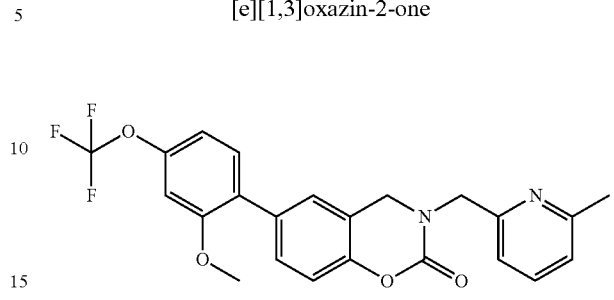

m/z (ESI)=445.1 [M+H]$^+$.
1H NMR (400 MHz, DMSO-d6) δ 7.87 (t, J=7.8 Hz, 1H), 7.47-7.28 (m, 5H), 7.12 (d, J=8.4 Hz, 2H), 7.01-6.99 (m, 1H), 4.72 (s, 2H), 4.66 (s, 2H), 2.53 (s, 3H).

Example 47

6-(2-fluoro-4-(trifluoromethoxy)phenyl)-3-((6-methylpyridin-2-yl)methyl)-3,4-dihydro-2H-benzo[e][1,3]oxazin-2-one

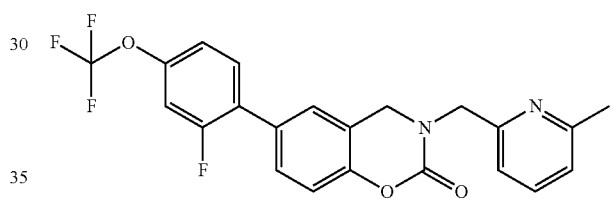

m/z (ESI)=433.1 [M+H]$^+$.
1H NMR (400 MHz, DMSO-d6) δ 7.89-7.80 (m, 1H), 7.65 (t, J=8.7 Hz, 1H), 7.55-7.43 (m, 3H), 7.43-7.29 (m, 3H), 7.20 (d, J=8.5 Hz, 1H), 4.74 (s, 2H), 4.69 (s, 2H), 2.53 (s, 3H).

Compounds of Examples 48-51 were prepared in a similar manner as the compound o Example 1-47 except that 5'-bromo-2'-hydroxyacetone was employed in place of 5-bromosalicylaldehyde.

Example 48

4-methyl-3-(pyrimidin-2-ylmethyl)-6-(4-(trifluoromethoxy)phenyl)-3,4-dihydro-2H-benzo[e][1,3]oxazin-2-one

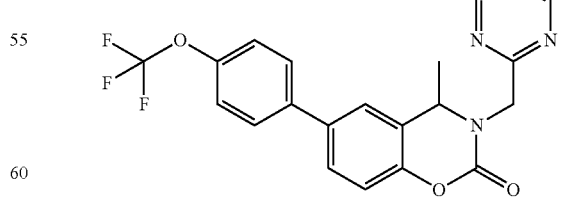

m/z (ESI)=416.1 [M+H]$^+$.
$^1$H NMR (400 MHz, DMSO-d$_6$) δ 8.75 (d, J=4.9 Hz, 2H), 7.84-7.73 (m, 2H), 7.68-7.57 (m, 2H), 7.49-7.33 (m, 3H), 7.23-7.13 (m, 1H), 5.00 (d, J=17.2 Hz, 1H), 4.80 (q, J=6.5 Hz, 1H), 4.69 (d, J=17.2 Hz, 1H), 1.51 (d, J=6.5 Hz, 3H).

Example 49

4-methyl-3-(pyrimidin-2-ylmethyl)-6-(4-(trifluoromethyl)phenyl)-3,4-dihydro-2H-benzo[e][1,3]oxazin-2-one

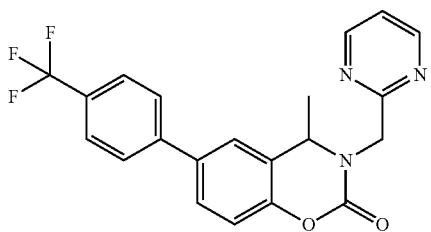 [SMILES: CC1c2cc(-c3ccc(C(F)(F)F)cc3)ccc2OC(=O)N1Cc1ncccn1]

m/z (ESI)=400.1 [M+H]$^+$.
$^1$H NMR (400 MHz, DMSO-d$_6$) δ 8.76 (d, J=4.9 Hz, 2H), 7.95-7.83 (m, 2H), 7.80 (d, J=8.3 Hz, 2H), 7.75-7.64 (m, 2H), 7.40 (t, J=4.9 Hz, 1H), 7.21 (d, J=9.1 Hz, 1H), 5.01 (d, J=17.2 Hz, 1H), 4.82 (q, J=6.5 Hz, 1H), 4.70 (d, J=17.2 Hz, 1H), 1.52 (d, J=6.5 Hz, 3H).

Example 50

4-methyl-3-(pyrimidin-2-ylmethyl)-6-(3-(trifluoromethoxy)phenyl)-3,4-dihydro-2H-benzo[e][1,3]oxazin-2-one

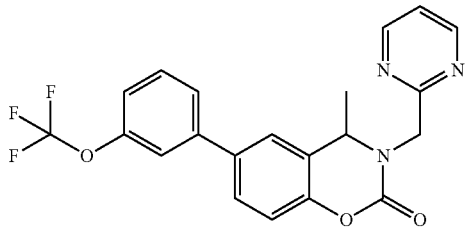 [SMILES: CC1c2cc(-c3cccc(OC(F)(F)F)c3)ccc2OC(=O)N1Cc1ncccn1]

m/z (ESI)=416.1 [M+H]$^+$.
$^1$H NMR (400 MHz, DMSO-d$_6$) δ 8.75 (d, J=4.9 Hz, 2H), 7.78-7.62 (m, 4H), 7.58 (t, J=8.0 Hz, 1H), 7.46-7.29 (m, 2H), 7.23-7.11 (m, 1H), 5.00 (d, J=17.2 Hz, 1H), 4.81 (q, J=6.5 Hz, 1H), 4.69 (d, J=17.2 Hz, 1H), 1.52 (d, J=6.5 Hz, 3H).

Example 51

4-methyl-6-(3-phenoxyphenyl)-3-(pyrimidin-2-ylmethyl)-3,4-dihydro-2H-benzo[e][1,3]oxazin-2-one

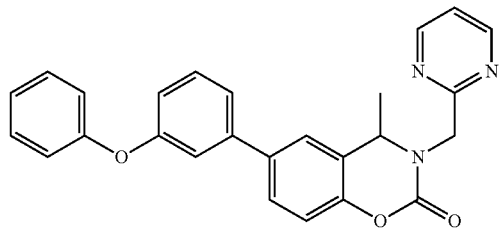 [SMILES: CC1c2cc(-c3cccc(Oc4ccccc4)c3)ccc2OC(=O)N1Cc1ncccn1]

m/z (ESI)=424.1 [M+H]$^+$.
$^1$H NMR (400 MHz, DMSO-d$_6$) δ 8.77 (d, J=4.9 Hz, 2H), 7.62 (d, J=8.0 Hz, 2H), 7.52-7.32 (m, 6H), 7.15 (ddt, J=8.4, 7.2, 1.1 Hz, 2H), 7.10-7.02 (m, 2H), 7.02-6.92 (m, 1H), 5.01 (d, J=17.2 Hz, 1H), 4.81 (q, J=6.3 Hz, 1H), 4.70 (d, J=17.2 Hz, 1H), 1.52 (d, J=6.5 Hz, 3H).

Example 52

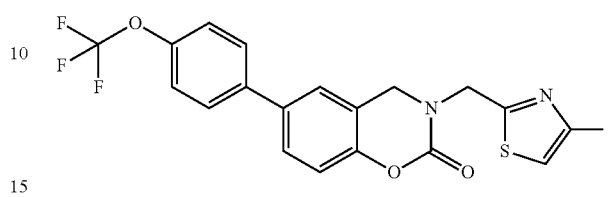

Compound of Example 52 was prepared following the procedure below

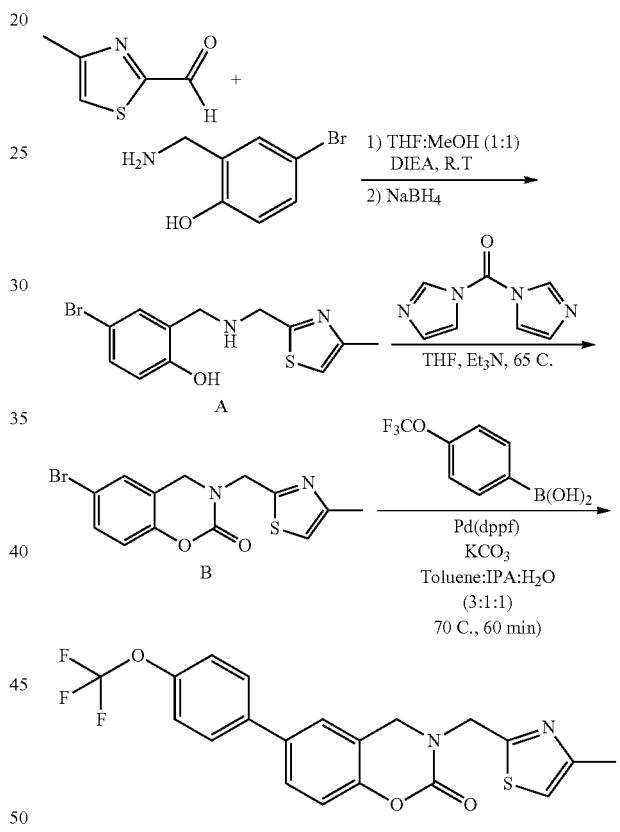

4-methyl-2-thiazolecarboxaldehyde (1.98 mmol) and 2-Aminomethyl-4-bromophenol (2.97 mmol) were added to a THF:MeOH (20:2 ml) mixture followed by addition of N,N-diisopropylethylamine (5-7 mmol) and stirred under N$_2$ at RT. The resulting mixture was stirred for several hours. 1.0 equiv. of NaBH$_4$ was added and the mixture was stirred at room tempt overnight. The excess hydride was quenched with 1N HCl. The mixture was concentrated to remove most of the organic solvent. Water was added and the organic phase was extracted with DCM. The organic phase was concentrated to give A.

A (1.60 mmol) was dissolved in THF (20 mL) followed by additions of carbonyldiimidazole (CDI) (2.40 mmol) and triethylamine (2 mL). The resulting mixture was refluxed for 2-4 hours. LCMS showed complete conversion to desired product B. The reaction mixture was concentrated and dissolved in DCM. The concentrate was washed with 1N HCl. The organic solvent was removed and the residue was used in next step without further purification.

B (0.074 mmol), (4-(trifluoromethoxy)phenyl)boronic acid (0.088 mmol), 1,1'-Bis(diphenylphosphino)ferrocene-palladium(II)dichloride dichloromethane complex [Pd(dppf)CH2C12] (0.004 mmol), and potassium carbonate (0.148 mmol) were combined with Toluene (3 ml), 2-propanol (1 mL) and water (1 mL) in a microwave reaction tube (round 2-5 mL size). The biphasic reaction mixture was heated at 70 C for 1 hr. LCMS showed complete conversion to desired product. The reaction mixture was filtered through a plug of celite with ethyl acetate. The filtrate was concentrated and purified by preparative TLC (5% MeOH:CH$_2$Cl$_2$) followed by preparative HPLC to give desired compound of Example 59.

m/z (ESI)=421.1 [M+H]$^+$.

$^1$H NMR (400 MHz, DMSO-d$_6$) δ 7.82-7.73 (m, 2H), 7.68-7.60 (m, 2H), 7.51-7.40 (m, 2H), 7.27 (d, J=1.1 Hz, 1H), 7.18 (d, J=9.2 Hz, 1H), 4.88 (s, 2H), 4.69 (s, 2H), 2.36 (d, J=1.0 Hz, 3H).

The following examples were prepared according to the procedure of Example 52 using the appropriate analogous reagents to obtain the respective desired compound.

Example 53

6-(3-fluoro-4-(trifluoromethoxy)phenyl)-3-((4-methylthiazol-2-yl)methyl)-3,4-dihydro-2H-benzo[e][1,3]oxazin-2-one

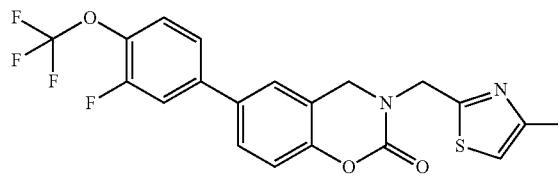 [SMILES: Cc1csc(CN2Cc3cc(-c4ccc(OC(F)(F)F)c(F)c4)ccc3OC2=O)n1]

m/z (ESI)=439.0 [M+H]$^+$.

$^1$H NMR (400 MHz, DMSO-d$_6$) δ 7.83 (dd, J=12.0, 2.1 Hz, 1H), 7.75-7.55 (m, 4H), 7.26 (q, J=1.0 Hz, 1H), 7.18 (d, J=9.1 Hz, 1H), 4.87 (s, 2H), 4.68 (s, 2H), 2.35 (d, J=1.0 Hz, 3H).

Example 54

6-(3-methyl-4-(trifluoromethoxy)phenyl)-3-((4-methylthiazol-2-yl)methyl)-3,4-dihydro-2H-benzo[e][1,3]oxazin-2-one

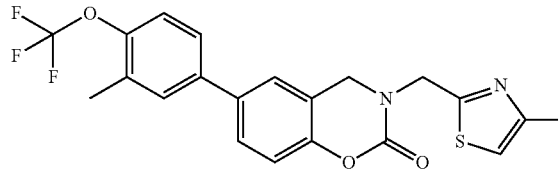 [SMILES: Cc1csc(CN2Cc3cc(-c4ccc(OC(F)(F)F)c(C)c4)ccc3OC2=O)n1]

m/z (ESI)=435.1 [M+H]$^+$.

$^1$H NMR (400 MHz, DMSO-d$_6$) δ 7.72-7.65 (m, 1H), 7.66-7.60 (m, 2H), 7.60-7.52 (m, 1H), 7.38 (dd, J=8.6, 1.6 Hz, 1H), 7.26 (q, J=1.0 Hz, 1H), 7.17 (d, J=9.1 Hz, 1H), 4.87 (s, 2H), 4.68 (s, 2H), 2.38-2.28 (m, 6H).

Example 55

6-(2-fluoro-4-(trifluoromethoxy)phenyl)-3-((4-methylthiazol-2-yl)methyl)-3,4-dihydro-2H-benzo[e][1,3]oxazin-2-one

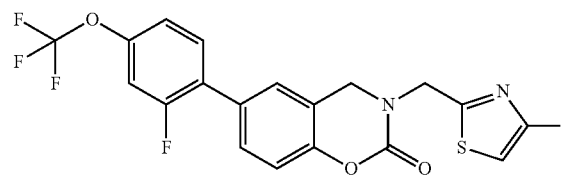 [SMILES: Cc1csc(CN2Cc3cc(-c4ccc(OC(F)(F)F)cc4F)ccc3OC2=O)n1]

m/z (ESI)=439.0 [M+H]$^+$.

HNMR (400 MHz, DMSO-d6) δ 7.66 (t, J=8.8 Hz, 1H), 7.60-7.41 (m, 3H), 7.41-7.31 (m, 1H), 7.29-7.12 (m, 2H), 4.87 (s, 2H), 4.69 (s, 2H), 2.35 (d, J=1.0 Hz, 3H).

Example 56

6-(3,4-dichlorophenyl)-3-((4-methylthiazol-2-yl)methyl)-3,4-dihydro-2H-benzo[e][1,3]oxazin-2-one

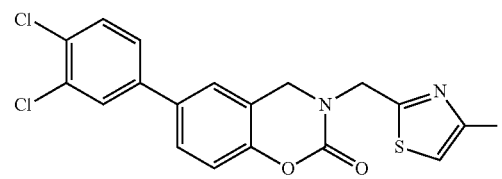 [SMILES: Cc1csc(CN2Cc3cc(-c4ccc(Cl)c(Cl)c4)ccc3OC2=O)n1]

m/z (ESI)=405.0 [M+H]$^+$.

1H NMR (400 MHz, DMSO-d6) δ 7.94 (d, J=2.1 Hz, 1H), 7.79-7.55 (m, 4H), 7.26 (d, J=1.0 Hz, 1H), 7.17 (d, J=8.6 Hz, 1H), 4.87 (s, 2H), 4.68 (s, 2H), 2.36 (d, J=1.0 Hz, 3H).

Example 57

6-(2-chloro-4-(trifluoromethoxy)phenyl)-3-((4-methylthiazol-2-yl)methyl)-3,4-dihydro-2H-benzo[e][1,3]oxazin-2-one

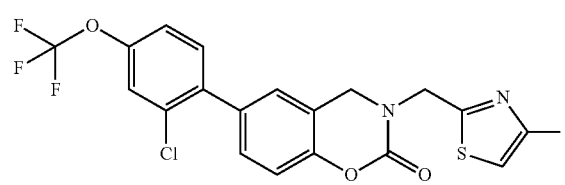 [SMILES: Cc1csc(CN2Cc3cc(-c4ccc(OC(F)(F)F)cc4Cl)ccc3OC2=O)n1]

m/z (ESI)=455.0 [M+H]$^+$.

1H NMR (400 MHz, DMSO-d6) δ 7.70 (d, J=2.3 Hz, 1H), 7.55 (d, J=8.6 Hz, 1H), 7.48 (d, J=2.1 Hz, 1H), 7.44-7.35 (m,

2H), 7.26 (s, 1H), 7.18 (d, J=8.2 Hz, 1H), 4.86 (s, 2H), 4.68 (s, 2H), 2.35 (s, 3H).

Example 58

6-(2-methoxy-4-(trifluoromethoxy)phenyl)-3-((4-methylthiazol-2-yl)methyl)-3,4-dihydro-2H-benzo[e][1,3]oxazin-2-one

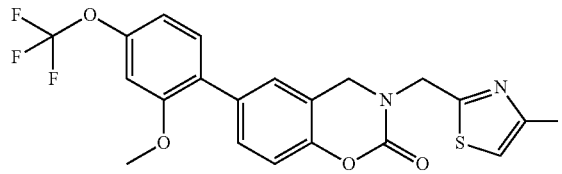 [SMILES: COc1cc(OC(F)(F)F)ccc1-c1ccc2c(c1)CN(Cc1nc(C)cs1)C(=O)O2]

m/z (ESI)=451.1 [M+H]+.

1H NMR (400 MHz, DMSO-d6) δ 7.50-7.32 (m, 3H), 7.26 (d, J=1.4 Hz, 1H), 7.12 (d, J=8.5 Hz, 2H), 7.06-6.93 (m, 1H), 4.86 (s, 2H), 4.66 (s, 2H), 2.35 (s, 3H).

Example 59

6-(4-chloro-3-fluorophenyl)-3-((4-methylthiazol-2-yl)methyl)-3,4-dihydro-2H-benzo[e][1,3]oxazin-2-one

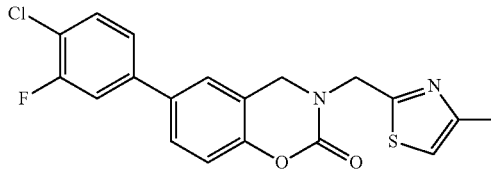 [SMILES: Cc1csc(CN2Cc3cc(-c4ccc(Cl)c(F)c4)ccc3OC2=O)n1]

m/z (ESI)=389.0 [M+H]+.

¹H NMR (400 MHz, DMSO-d₆) δ 7.81-7.59 (m, 4H), 7.54 (dd, J=8.5, 2.0 Hz, 1H), 7.26 (d, J=1.3 Hz, 1H), 7.18 (d, J=9.1 Hz, 1H), 4.87 (s, 2H), 4.68 (s, 2H), 2.36 (d, J=1.1 Hz, 3H).

Example 60

3-(pyrimidin-2-ylmethyl)-8-(trifluoromethoxy)-3,4-dihydrofluoreno[3,2-e][1,3]oxazin-2(10H)-one

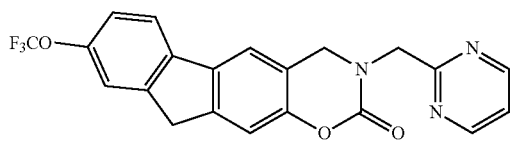 [SMILES: O=C1Oc2cc3c(cc2CN1Cc1ncccn1)-c1ccc(OC(F)(F)F)cc1C3]

The compound of Example 47 is prepared following the procedure below.

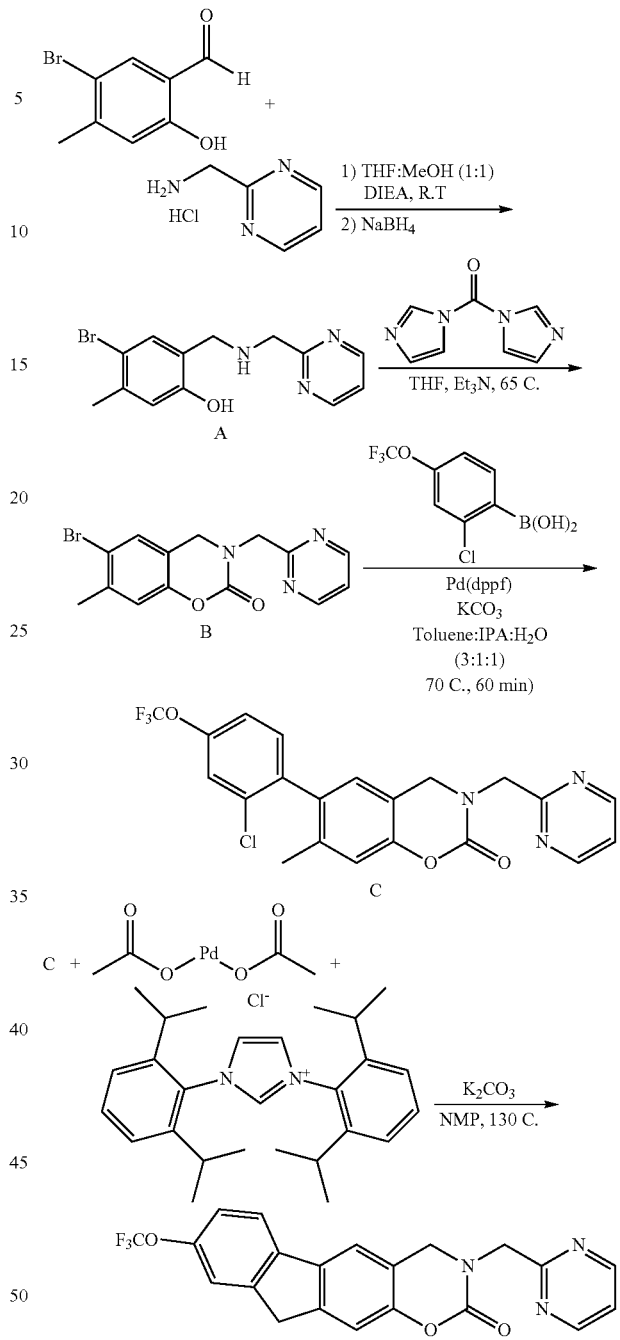

5-bromo-2-hydroxy-4-methylbenzaldehyde (0.94 mmol) and 2-Aminomethylpyridine HCl (1.4 mmol) were combined in THF:MeOH (10:1 mL) followed by addition of N,N-diisopropylethylamine (2 mmol) and stirred under N₂ at RT. The resulting mixture was stirred for 2 hr. Then 1.0 equiv. of NaBH4 was added and the mixture was stirred at room temperature overnight. The excess hydride was quenched with 1N HCl. The mixture was concentrated to remove most of the organic solvents. Water was added and the organic phase was extracted with DCM. The organic phase was concentrated to give A. A (0.79 mmol) was dissolved in THF (10 mL) followed by addition of carbonyldiimidazole (CDI) (1.2 mmol) and triethylamine (2 mL). The resulting mixture was refluxed for 2-4 hours. LCMS showed complete conversion to desired product B. The reaction mixture was concentrated and the concentrate was dissolved in DCM. The DCM solution was washed with 1N HCl. The organic solvent was removed and the residue was used in the next step without further purifications.

B (0.287 mmol), (2-chloro-4-(trifluoromethoxy)phenyl) boronic acid (0.345 mmol), 1,1'-bis(diphenylphosphino)ferrocene-palladium(II)dichloride dichloromethane complex [Pd(dppf)CH$_2$Cl$_2$] (0.014 mmol), and potassium carbonate (0.431 mmol) were combined with Toluene (3 ml), 2-propanol (1 ml), and water (1 ml) in a microwave reaction tube (round 2-5 mL size). The biphasic reaction mixture was heated at 70 C for 1 hr. LCMS showed complete conversion to desired product. The reaction mixture was filtered through a plug of celite with ethyl acetate. The filtrate was concentrated and purified by preparative TLC (5% MeOH:CH$_2$Cl$_2$) followed by preparative HPLC to give C.

C (0.11 mmol), 1,3-bis(2,6-diisopropylphenyl)-1H-imidazol-3-ium chloride (IPr-HCl)(0.004), palladium acetate (0.002 mmol), K$_2$CO$_3$ (0.11 mmol), and NMP were combined in a microwave reaction tube (round 2-5 mL size). The mixture was heated at 130 C overnight. After cooling, the solution was extracted with toluene and washed with water. The organics were concentrated down and purified with prep HPLC to yield compound of Example 60.

m/z (ESI)=414.1 [M+H]$^+$.

1H NMR (400 MHz, DMSO-d6) δ 8.81 (d, J=4.9 Hz, 2H), 7.94 (d, J=8.4 Hz, 1H), 7.81 (s, 1H), 7.60 (d, J=2.2 Hz, 1H), 7.51-7.27 (m, 3H), 4.81 (d, J=14.5 Hz, 4H), 4.01 (s, 2H).

Examples 61 through 70 below are illustrative of formulations that may be prepared using a compound of formula I, II, other novel compounds or novel combinations thereof disclosed herein.

Example 61

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Example 62

A tablet Formula comprising a compound of the disclosure is prepared using for example, the ingredients below:

| Ingredient | Quantity (mg/capsule) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Example 63

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

Example 64

Tablets, each containing 30 mg of active ingredient, are prepared as follows:

| Ingredient | Quantity (mg/capsule) |
| --- | --- |
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Example 65

Suppositories, each containing 25 mg of active ingredient are made as follows:

| Ingredient | Amount |
| --- | --- |
| Active Ingredient | 25 mg |
| Saturated fatty acids glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Example 66

Suspensions, each containing 50 mg of active ingredient per 5.0 mL dose are made as follows:

| Ingredient | Amount |
| --- | --- |
| Active Ingredient | 50.0 mg |
| Xanthan gum | 4.0 mg |
| Sodium carboxymethyl cellulose (11%) Microcrystalline cellulose (89%) | 500 mg |
| Sucrose | 1.75 g |

-continued

| Ingredient | Amount |
|---|---|
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Example 67

A subcutaneous formulation may be prepared as follows:

| Ingredient | Quantity |
|---|---|
| Active Ingredient | 5.0 mg |
| Corn Oil | 1.0 mL |

Example 68

An injectable preparation is prepared having the following composition:

| Ingredients | Amount |
|---|---|
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Example 69

A topical preparation is prepared having the following composition:

| Ingredients | grams |
|---|---|
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to 100 |

All of the above ingredients, except water, are combined and heated to 60° C. with stirring. A sufficient quantity of water at 60° C. is then added with vigorous stirring to emulsify the ingredients and water then added q.s. 100 g.

Example 70

Sustained Release Composition

| Ingredient | Weight Range % |
|---|---|
| Active ingredient | 50-95 |
| Macrocrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

The sustained release formulations of this disclosure are prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Example 71

Activity testing is conducted in the illustrative Examples below using methods described herein and/or well known in the art.

Cardiac Sodium Current Screening Assays:

The cardiac late sodium current (Late $I_{Na}$) and peak sodium current (Peak $I_{Na}$) assays are performed on an automated electrophysiology platform, QPatch 16X or QPatch HT (Sophion Bioscience, Copenhagen, Denmark) using the whole cell patch clamp technique to measure currents through the cell membrane. The assay uses an HEK293 (human embryonic kidney) cell line heterologously expressing the wild-type human cardiac sodium channel, hNa$_V$1.5, purchased from Millipore (Billerica, Mass.). No beta subunits were coexpressed with the Na channel alpha subunit. Cells are maintained with standard tissue culture procedures and stable channel expression is maintained with 400 µg/mL Geneticin in the culture medium. Experiments are carried out at 23-25° C.

For both the Late I$_{Na}$ and Peak I$_{Na}$ assays, series resistance compensation is set to 100% and series resistance and whole-cell compensation are performed automatically. Currents are digitized at 25 kHz and low-pass filtered at 5 kHz and stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. The extracellular solution for screening Late I$_{Na}$ is composed of: 140 mM NaCl, 4 mM KCl, 1.8 mM CaCl$_2$, 1 mM MgCl$_2$, 10 mM HEPES and 10 mM Dextrose with pH adjusted to 7.35 using NaOH. The intracellular solution contains: 105 mM CsF, 20 mM CsCl, 10 NaF, 2 mM EGTA, 10 mM HEPES and 10 mM Dextrose with pH adjusted to 7.35 with CsOH. Compounds are diluted in extracellular solution using a MicroLab Nimbus (Hamilton Robotics, Reno, Nev.) to between 0.3 and 3 µM in glass vials and transferred to glass well plates before robotic addition to the cells. The 0 mM Na extracellular solution (0Na-ECF) used at the end of each experiment for the Late I$_{Na}$ and Peak I$_{Na}$ assays to measure baseline current contains: 140 Choline-Cl; 4 mM KCl, 1.8 mM CaCl$_2$; 1 mM MgCl$_2$; 10 mM HEPES and 10 mM Dextrose with pH was adjusted to 7.35 with CsOH.

Late I$_{Na}$ Screening Assay:

For the Late I$_{Na}$ assay, sodium channels are activated every 10 seconds (0.1 Hz) by depolarizing the cell membrane to −20 mV for 250 milliseconds (ms) from a holding potential of −120 mV.

Compounds were tested to determine their activity in blocking the late sodium current. Late I$_{Na}$ was generated by adding 10 µM Tefluthrin (pyrethroid) to the extracellular solution. For the purposes of the screening, Late I$_{Na}$ is defined as the mean current between 240 ms and 265 ms during the voltage step to −20 mV. After establishing the whole cell recording configuration, Late I$_{Na}$ activator is added to each well 4 times over a 15 minute period so that the late component of the Na current reaches a stable value. Compounds were then added (typically at 0.3 or 1 µM), in the presence of the Late I$_{Na}$ activator, with 3 additions over the course of 5 minutes. Measurements were made at the end of exposure to the third compound addition and values were normalized to the current level when all Na$^+$ was removed from the extracellular solution after two additions of 0Na-ECF.

Results are reported as percent block of late I$_{Na}$ and results were analyzed by incorporating rundown correction for the Late I$_{Na}$. For example the compound of Example 19 inhibited (or reduced) the late sodium current by 68% at a 1 µM concentration (see Table 1 for additional compound data).

Peak I$_{Na}$ Screening Assay:

Compounds were evaluated for their effect Na$_V$ 1.5 Peak I$_{Na}$. It is contemplated that the compounds of Formula I avoid significant block of peak I$_{Na}$. Since the peak I$_{Na}$ in the cells used herein can be very large, introducing artifacts in the recording, the concentration of Na$^+$ in the bath can be reduced to 40 mM by isosmotic replacement of Na$^+$ with Choline (see below).

Tonic Block (TB) of Peak I$_{Na}$ was measured using a voltage step to −20 mV from a holding potential of −100 mV at a low stimulation frequency of 0.1 Hz. Use-Dependent Block (UDB) of Peak I$_{Na}$ was measured during pulse number 50 of a pulse train (−20 mV, 20 ms, 50 pulses, 3 Hz) from a holding potential of −100 mV.

Block of cardiac Peak I$_{Na}$ by compounds of this disclosure is typically increased with an increase in the frequency of stimulation from 0.1 to 3 Hz (frequencies encountered either in the normal heart or during tachycardia).

The extracellular solution for screening Peak I$_{Na}$ is composed of: 40 mM NaCl, 100 mM Choline-Cl, 4 mM KCl, 1.8 mM CaCl$_2$, 1 mM MgCl$_2$ 10 mM HEPES and 10 mM Dextrose with pH adjusted to 7.35 using NaOH. The intracellular solution used for the Peak I$_{Na}$ assay is the same as outlined for the Late I$_{Na}$ assay (see above).

After establishing the whole cell recording configuration, channels were stimulated to open with low frequency (0.1 Hz) for so that the recording can be monitored and the extent to which the recording has stabilized can be assessed.

The test compound is then applied at 1 or 3 µM was added 2 times at 60 second intervals. After the second compound addition, a 200 second wait period was imposed to allow for equilibration. Voltage protocols for TB and UDB are were performed in the absence and presence of compound and TB and UDB are calculated with respect to the compound free condition. Both TB and UDB were analyzed by incorporating rundown correction for the peak I$_{Na}$. For example, the compound of example 19 exhibited peak I$_{Na}$ TB of 26.7% and peak I$_{Na}$ UDB of 9.6%, both measured at 3 µM. Additional data is provided in Table 1.

The above data demonstrates the selectivity of Compound of Example 1 to block Late INa compared to peak I$_{Na}$ (68.3% versus 26.7% for peak I$_{Na}$ TB; and 68.3% versus 9.6% for peak INa UDB) and suggests that Compound of Example 1 should show minimal to no effects on conduction through the heart (which is driven by peak INa) at concentrations that effectively block Late I$_{Na}$.

Compounds were tested using the herein described assay methods. Data are obtained by testing the listed compounds at 1 or 3 µM concentration in the Late I$_{Na}$ and Peak I$_{Na}$ assays (and other concentrations as needed as presented below). The data is provided as % inhibition in Table 1.

TABLE 1

Late I$_{Na}$, Peak I$_{Na}$, Na$_V$1.1 and Na$_V$1.2 Assay results

| Example | Nav1.5 Late I$_{Na}$ 1 uM | Nav1.5 Peak TB 3 uM | Nav1.5 Peak UDB 3 Hz 3 uM | Nav1.1 UDB 25 Hz 1 uM | Nav1.1 UDB 25 Hz 10 uM | Nav1.2 UDB 25 Hz 1 uM | Nav1.2 UDB 25 Hz 10 uM |
|---|---|---|---|---|---|---|---|
| 1 | 45.0 | 18.9 | <5 | <5 | 34.4 | 7.9 | 37.0 |
| 2 | 41.5 | 18.5 | 16.2 | 9.7 | 22.6 | 19.8 | 28.1 |
| 3 | 51.8 | | | 42.6 | 91.6 | | |
| 4 | 53.9 | | | 49.9 | 76.5 | | |
| 5 | 37.3 | 10.1 | <5 | <5 | 15.3 | <5 | 24.9 |
| 6 | 43.3 | 19.9 | <5 | 26.7 | 65.2 | | |
| 7 | 42.3 | 14.9 | <5 | 5.7 | 42.4 | 18.0 | 56.3 |
| 8 | 52.7 | 12.5 | <5 | <5 | 11.6 | <5 | 11.0 |
| 9 | 45.0 | 18.9 | <5 | <5 | 34.4 | 7.9 | 37.0 |
| 10 | 57.2 | 14.2 | 10.8 | 35.0 | 75.9 | 30.2 | 75.0 |
| 11 | 32.5 | 19.4 | 5.6 | 21.0 | 81.1 | 29.9 | 77.2 |
| 12 | 50.5 | 16.6 | <5 | 7.5 | 73.9 | 15.4 | 68.8 |
| 13 | 49.6 | 29.4 | 5.6 | 37.5 | 88.8 | 21.4 | 63.4 |

TABLE 1-continued

Late $I_{Na}$, Peak $I_{Na}$, Na$_V$1.1 and Na$_V$1.2 Assay results

| Example | Nav1.5 Late $I_{Na}$ 1 uM | Nav1.5 Peak TB 3 uM | Nav1.5 Peak UDB 3 Hz 3 uM | Nav1.1 UDB 25 Hz 1 uM | Nav1.1 UDB 25 Hz 10 uM | Nav1.2 UDB 25 Hz 1 uM | Nav1.2 UDB 25 Hz 10 uM |
|---|---|---|---|---|---|---|---|
| 14 | 39.3 | 24.0 | <5 | <5 | 43.8 | <5 | 59.9 |
| 15 | 30.0 | | | | | | |
| 16 | 48.5 | 22.1 | 5.3 | 17.3 | 52.2 | 23.4 | 52.9 |
| 17 | 45.0 | 12.9 | <5 | 34.8 | 60.9 | 34.2 | 56.6 |
| 18 | 31.4 | 12.1 | <5 | 16.9 | 73.4 | 9.1 | 54.9 |
| 19 | 68.3 | 26.7 | 9.6 | 30.8 | 78.4 | 30.6 | 64.0 |
| 20 | 53.7 | 32.8 | 5.1 | 29.1 | 82.0 | 30.2 | 69.8 |
| 21 | 44.7 | 23.0 | <5 | <5 | 50.8 | <5 | 59.4 |
| 22 | 48.3 | 24.9 | <5 | <5 | 56.3 | <5 | 55.6 |
| 23 | 30.5 | 19.4 | <5 | 5.2 | 75.2 | <5 | 56.0 |
| 24 | 55.8 | 28.5 | 5.9 | 44.9 | 79.6 | 32.7 | 71.4 |
| 25 | 54.0 | 29.7 | <5 | 31.7 | 75.3 | 29.9 | 72.1 |
| 26 | 35.2 | 20.7 | <5 | 14.8 | 66.1 | 28.0 | 71.1 |
| 27 | 60.1 | 32.0 | 8.1 | 28.4 | 77.5 | 42.2 | 80.6 |
| 28 | 45.4 | 12.9 | 6.9 | 25.2 | 67.4 | 17.1 | 58.0 |
| 29 | 61.6 | 36.1 | 14.1 | 44.7 | 86.8 | 36.1 | 81.7 |
| 30 | 54.5 | 36.5 | 13.2 | 49.7 | 87.5 | 47.1 | 79.6 |
| 31 | 34.4 | 12.2 | <5 | 6.0 | 53.3 | 13.2 | 45.7 |
| 32 | 43.4 | 33.1 | <5 | 10.8 | 61.8 | 8.1 | 41.0 |
| 33 | 33.0 | 27.8 | <5 | 5.5 | 61.4 | 17.2 | 55.2 |
| 34 | 44.6 | 27.7 | <5 | 26.9 | 76.1 | 38.8 | 78.5 |
| 35 | 49.4 | 20.2 | 9.7 | 37.6 | 80.4 | 39.3 | 75.1 |
| 36 | 43.6 | 11.5 | 5.9 | 22.8 | 68.7 | 19.1 | 55.9 |
| 37 | 41.1 | 14.0 | <5 | 7.3 | 67.7 | 7.8 | 27.1 |
| 38 | 54.2 | 55.6 | <5 | 49.0 | 78.1 | 34.1 | 71.8 |
| 39 | 33.7 | 17.5 | 5.9 | 39.1 | 73.4 | 16.0 | 59.3 |
| 40 | 49.4 | 22.4 | 10.2 | 22.6 | 71.3 | 16.7 | 62.5 |
| 41 | 45.7 | 17.5 | <5 | <5 | 29.0 | 7.1 | 36.2 |
| 42 | 42.7 | 12.7 | <5 | 11.5 | 47.9 | 13.3 | 47.4 |
| 43 | 37.9 | 19.2 | <5 | <5 | 51.4 | <5 | 48.9 |
| 44 | 44.8 | 21.6 | <5 | 25.0 | 84.5 | 20.9 | 68.4 |
| 45 | 53.6 | 33.5 | <5 | 19.9 | 72.8 | 10.4 | 62.3 |
| 46 | 51.3 | 34.7 | <5 | 19.0 | 78.6 | 22.4 | 77.2 |
| 47 | 52.8 | 44.3 | <5 | <5 | 69.2 | 14.1 | 55.6 |
| 48 | 53.2 | 12.1 | | 32.5 | 73.3 | | |
| 49 | 41.5 | | | 21.5 | 82.4 | | |
| 50 | 34.9 | 17.7 | 12.1 | 10.1 | 71.2 | | |
| 51 | 41.6 | | | | | | |
| 52 | 58.0 | 11.9 | <5 | 32.9 | 57.6 | 20.8 | 63.7 |
| 53 | 60.3 | 19.8 | <5 | 52.7 | 87.6 | 32.3 | 73.6 |
| 54 | 31.0 | 11.2 | <5 | <5 | 36.7 | 6.1 | 43.5 |
| 55 | 35.3 | 16.1 | <5 | <5 | 55.0 | 22.6 | 61.8 |
| 56 | 39.0 | <5 | <5 | <5 | 10.7 | <5 | 15.2 |
| 57 | 34.1 | <5 | <5 | <5 | 48.8 | 12.8 | 61.5 |
| 58 | 44.1 | 7.9 | <5 | 7.8 | 68.7 | 10.6 | 58.7 |
| 59 | 50.3 | 13.0 | <5 | 20.7 | 39.9 | <5 | 41.2 |
| 60 | 11.2 | | | | | | |

The assay results shown in the above table illustrate that compounds tested showed activity as modulators of late sodium current, for example by inhibiting (or reducing) the late sodium current.

In some embodiments the effects of a compound of Formula I are specific for the late sodium current and show little or no activity with respect to one or more other ion channels. Thus, in some embodiments, a compound having an activity of reducing late sodium current will also exhibit little or no activity with regard to the peak sodium current.

Example 72

Use-Dependent Inhibition of the CNS Na$_V$1.1 Sodium Channel

Expression of Human Na$_V$1.1 cDNA

HEK-293 cells stably expressing wild-type (WT) hNa$_V$1.1 (SCN1A, NCBI# AB09354) were obtained from Millipore (Cat. # CYL3009) were used to record $I_{Na}$. Cells are maintained with standard tissue culture procedures and stable channel expression is maintained with 400 ug/mL G418 in the culture medium. Unless otherwise noted, all reagents are purchased from Sigma-Aldrich (St Louis, Mo., U.S.A.).

Electrophysiology

Assays measuring Use-Dependent Block (UDB) of Na$_V$1.2 are performed on an automated electrophysiology platform, QPatch 16X or QPatch HT (Sophion Bioscience, Copenhagen, Denmark), using the whole cell patch clamp technique to measure currents through the cell membrane. Series resistance compensation is set to 100% and series resistance and whole-cell compensation are performed automatically. Currents stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

The internal (pipette) solution consists of (in mM) 105 CsF, 10 NaF, 20 CsCl, 2 EGTA, 10 HEPES, 10 Dextrose with a pH of 7.35 and osmolarity of 300 mOsmol/kg. The external (bath) solution contains in (mM): 145 NaCl, 4 KCl, 1.8 CaCl$_2$, 1 MgCl$_2$, 10 dextrose, 10 HEPES, with a pH of 7.35 and osmolarity of 310 mOsmol/kg. Experiments are carried out at 23-25° C.

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. Compounds are diluted in extracellular solution using a MicroLab Nimbus (Hamilton Robotics, Reno, Nev.) to between 0.3 and 3 µM in glass vials and transferred to glass well plates before robotic addition to the cells.

Cells are allowed to stabilize for 10 min after establishment of the whole-cell configuration before current is measured. The test compound is applied 2 times at 60 second intervals. After the second compound addition, a 200 second wait period was imposed to allow for equilibration.

Leak currents are subtracted by using an online P/4 procedure and all currents are low-pass Bessel filtered at 5 kHz and digitized at 525 kHz.

Use-dependent block of Na$_V$1.2 peak current is measured during pulse number 20 of a voltage pulse train (0 mV, 20 ms, 20 pulses, 25 Hz) from a holding potential of −120 mV. Currents are normalized to the peak current recorded in response to the first pulse in each frequency train. The voltage protocol for UDB was performed in the absence and presence of compound and percentage inhibition was calculated with respect to the compound free condition. Results are presented as mean percentage inhibition and data analysis is performed using QPatch Assay Software 4.0, and Excel 2002 (Microsoft, Seattle, Wash., U.S.A.).

Example 73

Use-Dependent Inhibition of the CNS Na$_V$1.2 Sodium Channel

Expression of Human Na$_V$1.2 cDNA

HEK-293 cells stably expressing wild-type (WT) hNaV1.2 (SCN2A NCBI # NM_021007.2, SCN1B NCBI # NM_001037.4, SCN2B NCBI # NM_004588.2) were used to record $I_{Na}$. Cells are maintained with standard tissue culture procedures and stable channel expression is maintained with 800 ug/mL G418 and 3 ug/mL Puromycin in the culture medium. Unless otherwise noted, all reagents are purchased from Sigma-Aldrich (St Louis, Mo., U.S.A.).

Electrophysiology

Assays measuring Use-Dependent Block (UDB) of $Na_V1.2$ are performed on an automated electrophysiology platform, QPatch 16X or QPatch HT (Sophion Bioscience, Copenhagen, Denmark), using the whole cell patch clamp technique to measure currents through the cell membrane. Series resistance compensation is set to 100% and series resistance and whole-cell compensation are performed automatically. Currents stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.). The internal (pipette) solution consists of (in mM) 105 CsF, 10 NaF, 20 CsCl, 2 EGTA, 10 HEPES, 10 Dextrose with a pH of 7.35 and osmolarity of 300 mOsmol/kg. The external (bath) solution contains in (mM): 145 NaCl, 4 KCl, 1.8 $CaCl_2$, 1 $MgCl_2$, 10 dextrose, 10 HEPES, with a pH of 7.35 and osmolarity of 310 mOsmol/kg. Experiments are carried out at 23-25° C.

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. Compounds are diluted in extracellular solution using a MicroLab Nimbus (Hamilton Robotics, Reno, Nev.) to between 0.3 and 3 µM in glass vials and transferred to glass well plates before robotic addition to the cells.

Cells are allowed to stabilize for 10 min after establishment of the whole-cell configuration before current is measured. The test compound is applied 2 times at 60 second intervals. After the second compound addition, a 200 second wait period was imposed to allow for equilibration. Leak currents are subtracted by using an online P/4 procedure and all currents are low-pass Bessel filtered at 5 kHz and digitized at 525 kHz.

Results are presented as mean percentage inhibition.

Use-dependent block of $Na_V1.2$ peak current is measured during pulse number 20 of a voltage pulse train (0 mV, 20 ms, 20 pulses, 25 Hz) from a holding potential of −120 mV.

Currents are normalized to the peak current recorded in response to the first pulse in each frequency train. The voltage protocol for UDB was performed in the absence and presence of compound and percentage inhibition was calculated with respect to the compound free condition.

Data analysis is performed using QPatch Assay Software 4.0, and Excel 2002 (Microsoft, Seattle, Wash., U.S.A.). Results are provided in Table 1 above.

When tested in the assay disclosed above for $hNa_V1.1$ and $hNa_V1.2$ sodium channel isoforms at a frequency of 25 Hz, the compound of Example 19 blocked both $hNa_V1.1$ and $hNa_V1.2$ isoforms with 78.4 and 64.0% inhibition respectively. The inhibition of $hNa_V1.1$ and $hNa_V1.2$ isoforms or the inhibition of both channels when stimulated at these frequencies support the utility of compounds of this disclosure to treat patients with epilepsy.

Example 74

Voltage-Dependent Inhibition of the $Na_V1.3$ Sodium Channel

Expression of Human $Na_V1.3$ cDNA

HEK-293 cells stably expressing wild-type (WT) $hNa_V1.3$ (SCN3A NCBI # NP_001075, SCN1B NCBI # NM_001037.4, SCN2B NCBI # NM_004588.2) were used to record $I_{Na}$. Cells are maintained with standard tissue culture procedures and stable channel expression is maintained with 800 ug/mL G418 and 3 ug/mL Puromycin in the culture medium. Unless otherwise noted, all reagents are purchased from Sigma-Aldrich (St Louis, Mo., U.S.A.).

Electrophysiology

Assays measuring Voltage-Dependent Block (VDB) of $Na_V1.3$ are performed on an automated electrophysiology platform, QPatch 16X or QPatch HT (Sophion Bioscience, Copenhagen, Denmark), using the whole cell patch clamp technique to measure currents through the cell membrane. Series resistance compensation is set to 100% and series resistance and whole-cell compensation are performed automatically. Currents stored in the Sophion Bioscience Oracle database (Sophion Bioscience, Copenhagen, Denmark). Analysis is performed using QPatch Assay software and data are compiled in Excel 2010 (Microsoft, Seattle, Wash., U.S.A.).

The internal (pipette) solution consists of (in mM) 105 CsF, 10 NaF, 20 CsCl, 2 EGTA, 10 HEPES, 10 Dextrose with a pH of 7.35 and osmolarity of 300 mOsmol/kg. The external (bath) solution contains in (mM): 80 NaCl, 60 Choline-Cl, 4 KCl, 1.8 $CaCl_2$, 1 $MgCl_2$, 10 dextrose, 10 HEPES, with a pH of 7.35 and osmolarity of 310 mOsmol/kg. Experiments are carried out at 23-25° C.

Compound stocks are routinely made by the Gilead Sample Bank in vials to 10 mM in dimethyl sulfoxide (DMSO). In some cases, when compounds are not soluble in DMSO, they are made in 100% ethanol. Stocks are sonicated as necessary. Compounds are diluted in extracellular solution using a MicroLab Nimbus (Hamilton Robotics, Reno, Nev.) to 1 µM in glass vials and transferred to glass well plates before robotic addition to the cells. Cells are allowed to stabilize for 10 min after establishment of the whole-cell configuration before current is measured. The test compound is applied 3 times at 120 second intervals to allow for equilibration. Currents were leak subtracted using a P/4 procedure, low-pass Bessel filtered at 5 kHz and digitized at 25 kHz. Results are presented as mean percentage inhibition.

Voltage-dependent block of $Na_V1.3$ peak current was measured during a voltage step to 0 mV (20 ms) following a voltage step pre-conditioning steps (−55 mV for 10 sec followed by −120 mV for 10 ms). The holding potential was −120 mV and this voltage protocol induces half maximal inactivation of $Na_V1.3$. The voltage protocol for VDB was performed every 45 seconds in the absence and presence of compound and percentage inhibition was calculated with respect to the compound free condition.

Data for sample tested compounds are provided below in Table 2.

TABLE 2

| $Na_V1.3$ Assay Results | |
|---|---|
| Example No. | $Na_V1.3$ VDB % inhibition at 1 uM |
| 8 | 13.8 |
| 7 | 32 |
| 5 | 31 |

Example 75

Ischemia-Induced ST Segment Elevation in Anesthetized Rabbits

This study was undertaken to determine the anti-ischemic effects of compounds of the present disclosure in an in vivo rabbit model.

Methods:

Female New Zealand rabbits (3.0-4.0 kg) were purchased from Western Oregon Rabbitry. Animals were housed on a 12-h light and dark cycle and received standard laboratory chow and water. All experiments were performed in accordance with the Guide for the Care and Use of Laboratory Animals published by The National Research Council and with the experimental protocol approved by the Institutional Animal Care Committee of Gilead Sciences, Inc.

Rabbits were anesthetized with ketamine (35 mg/kg) and xylazine (5 mg/kg) intramuscular injection (im). A tracheotomy was performed and the trachea was intubated with an endotracheal tube. The animal was ventilated with room air supplemented with oxygen using a pressure control animal ventilator (Kent Scientific Corp., Torrington, Conn.) at a respiratory rate of 40 strokes/min and peak inspiration pressure of 10 mmH$_2$O, which was adjusted to keep blood gases and pH within the physiological range (iSTAT clinic analyzer, Heska Corp.; Waukesha, Wis.). The left femoral artery was cannulated for the measurement of blood pressure (BP). Blood samples were also withdrawn from femoral artery. The right external jugular vein was cannulated for drug/vehicle administration. Needle electrodes were inserted subcutaneously into the limbs for recording of the surface electrocardiogram (ECG).

The heart was exposed via an incision in the 4$^{th}$ intercostal space (4$^{th}$ and/or 5$^{th}$ ribs were cut for a clear surgical vision). The chest was opened and a pericardial cradle was formed using 4 retractors. A coronary artery occluder, comprised of a snare made of 5 cm PE-10 tubing with a 6-0 Prolene polypropylene suture in it, was placed loosely around the left anterior descending artery (LAD) at its origin. Two unipolar electrodes, made with teflon coated silver wire attached to a small patch of filter paper, were attached on the surface of the ischemic and normal regions of the left ventricle to record epicardial electrocardiogram.

Reference electrodes were placed in the open incision of the neck. The body temperature of the animal was monitored via a rectal thermometer and maintained at 37-40° C. by adjusting the surface temperature of the surgical table. Regional ischemia (15 min) was induced by ligating the LAD followed by 15 min of reperfusion caused by releasing the ligation. The heart was excised at the end of the experiment and the LAD was re-ligated. The ischemic area was visualized by perfusing the heart with 1% Evans blue in saline and calculated as a percentage of total ventricular weight. Rabbits with ischemic area less than 10% or larger than 25% were excluded from the analysis. Animals were randomly assigned to vehicle and test compound groups. Test compounds were dissolved in 15% NMP, 10% Solutol and 75% de-ionized water (dH$_2$O). Test compounds were given as an iv infusion at a rate targeted to reach plasma concentrations of 1 μM. After 30 min of compound administration the heart was subjected to 15 min of ischemia followed by 15 min of reperfusion.

Results:

The compound of Example 1 or other compound examples disclosed herein may prevent the ischemia-induced ST segment elevation. The compound of Example 1 exhibited a 58% inhibition at 0.9 uM concentration in the rabbit ST segment elevation assay.

What is claimed is:

1. A compound of Formula I:

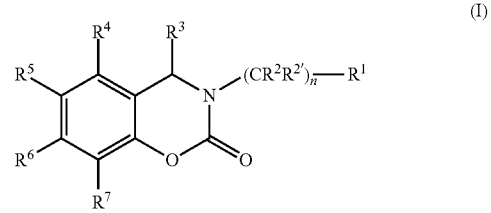

wherein $R^1$ is a 5 or 6 membered aryl, heteroaryl or heterocyclic group wherein each heteroaryl or heterocyclic group contains from 1 to 3 heteroatoms independently selected from the group consisting of nitrogen, oxygen and sulfur; and wherein the aryl, heteroaryl or heterocyclic group is optionally substituted with 1 or 2 groups independently selected from the group consisting of —C$_1$-C$_6$ alkyl, —C$_3$-C$_6$ cycloalkyl, C$_1$-C$_6$ alkylC$_3$-C$_6$ cycloalkyl, halogen, —C$_1$-C$_6$ haloalkyl, —OC$_1$-C$_6$ alkyl, —OC$_1$-C$_6$ haloalkyl, and —C(O)C$_1$-C$_6$ alkyl;

$R^2$ and $R^{2'}$ are at each occurrence independently H or —C$_1$-C$_6$ alkyl; or one set of $R^2$ and $R^{2'}$ combine with the carbon atom to which they are both attached to from a C$_3$-C$_6$ cycloalkyl group;

$R^3$ is H, —C$_1$-C$_6$ alkyl or C$_3$-C$_6$ cycloalkyl, $R^4$ is H, —C$_1$-C$_6$ alkyl, —OC$_1$-C$_6$ alkyl, —OC$_1$-C$_6$ haloalkyl, —C$_3$-C$_6$ cycloalkyl, or halo;

$R^5$ is a 5 or 6 membered aryl, heteroaryl or heterocyclic group optionally substituted with one, two or three groups independently selected from the group consisting of —C$_1$-C$_6$ alkyl, —C$_2$-C$_6$ alkenyl, —C$_2$-C$_6$ alkynyl, C$_3$-C$_6$ cycloalkyl, C$_1$-C$_6$ alkylC$_3$-C$_6$ cycloalkyl, —C$_1$-C$_6$ haloalkyl, —OC$_1$-C$_6$ alkyl,—OC$_1$-C$_6$ haloalkyl, —O-aryl, and halo; wherein the cycloalkyl group is optionally substituted with —C$_1$-C$_6$ alkyl or —C$_1$-C$_6$ haloalkyl; and wherein the substituent —O-aryl group is optionally substituted with —C$_1$-C$_6$ alkyl, halo, C$_1$-C$_6$ haloalkyl, —OC$_1$-C$_6$ alkyl, or —OC$_1$-C$_6$ haloalkyl; and wherein two substituents on the aryl, heteroaryl, or heterocyclic ring of $R^5$ optionally combine to form a 8-12 membered bicyclic ring optionally containing one or two oxygen atoms; and wherein the bicyclic ring is optionally substituted with 1 or 2 groups independently selected from the group consisting of —C$_1$-C$_6$ alkyl, —C$_1$-C$_6$ haloalkyl, —OC$_1$-C$_6$ alkyl, —OC$_1$-C$_6$ haloalkyl, —C$_3$-C$_6$ cycloalkyl, and halo;

$R^6$ is H, —C$_1$-C$_6$ alkyl, —C$_1$-C$_6$ haloalkyl,—OC$_1$-C$_6$ alkyl, —OC$_1$-C$_6$ haloalky, or halo; or $R^6$ combines with a substituent on the aryl, heteroaryl or heterocyclic ring of $R^5$ to form a ring optionally substituted with 1 or 2 groups independently selected from C$_1$-C$_6$ alkyl, —C$_1$-C$_6$ haloalkyl, —OC$_1$-C$_6$ alkyl, —OC$_1$-C$_6$ haloalkyl, —C$_3$-C$_6$ cycloalkyl, and halo;

$R^7$ is H, —C$_1$-C$_6$ alkyl, —C$_1$-C$_6$ haloalkyl, —OC$_1$-C$_6$ alkyl, —C$_1$-C$_6$ haloalkyl or halo;

n =1-4;

or a pharmaceutically acceptable salt thereof.

2. A coumpound of Formula 1

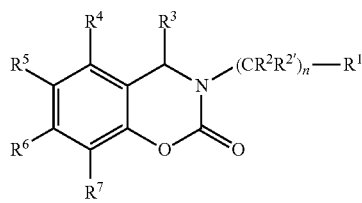

wherein
- $R^1$ is a pyrimidinyl, pyridinyl, imidazolyl thiazolyl, oxazolyl, or triazolyl group optionally substituted with 1, or 2 groups independently selected from the group consisting of $C_1$-$C_6$ alkyl, $C_3$-$C_6$cycloalkyl, halogen, $C_1$-$C_6$ haloalkyl, $C_1$-$C_6$ alkoxy, —$OC_1$-$C_6$ haloalkyl, and —$C(O)C_1$-$C_6$ alkyl;
- $R^2$ and $R^{2'}$ are at each occurrence independently H or $C_1$-$C_6$ alkyl; or one set of $R^2$ and $R^{2'}$ combines with the carbon atom to which they are both attached to form a cycloalkyl group having from 3 to 6 carbon atoms;
- $R^3$ is H or —$C_1$-$C_6$ alkyl;
- $R^4$ is H, —$C_1$-$C_6$ alkyl, or halo;
- $R^5$ is a phenyl group substituted with one or two groups independently selected from the group consisting of —$C_1$-$C_6$ alkyl, $C_3$-$C_6$ cycloalkyl, —$C_1$-$C_6$ alkyl$C_3$-$C_6$ cycloalkyl, —$C_1$-$C_6$ haloalkyl, —$OC_1$-$C_6$ alkyl, —$OC_1$-$C_6$ haloalkyl, —O-aryl, and halo; wherein the cycloalkyl group is optionally substituted with $C_1$-$C_6$ alkyl or $C_1$-$C_6$ haloalkyl; wherein the substituent —O-aryl group is optionally substituted with $C_1$-$C_6$ alkyl, halo, $C_1$-$C_6$ haloalkyl, —$OC_1$-$C_6$ alkyl, or —$OC_1$-$C_6$ haloalkyl;
- wherein two substituents on the phenyl ring of $R^5$ optionally combine to form a bicyclic ring optionally containing one or two oxygen atoms; and wherein the bicyclic ring is optionally substituted with 1 or 2 groups independently selected from the group consisting of —$C_1$-$C_6$ alkyl and halogen;
- $R^6$ is H, —$C_1$-$C_6$ alkyl, —$C_1$-$C_6$ haloalkyl, —$OC_1$-$C_6$ alkyl, —$OC_1$-$C_6$ haloalkyl, or halo;
- $R^7$ is H, —$C_1$-$C_6$ alkyl, —$C_1$-$C_6$haloalkyl, —$OC_1$-$C_6$ alkyl, —$C_1$-$C_6$ haloalkyl, or halo;
- n=1-4;
- or a pharmaceutically acceptable salt thereof.

3. The compound according to claim 2 wherein:
- $R^1$ is a pyrimidinyl, pyridinyl, imidazolyl, thiazolyl, oxazolyl, or triazolyl group optionally substituted with 1 or 2 groups independently selected from the group consisting of $C_1$-$C_3$ alkyl, and $C_3$-$C_6$ cycloalkyl;
- $R^2$ and $R^{2'}$ are at each occurrence independently H or $C_1$-$C_3$ alkyl; or one set of $R^2$ and $R^{2'}$optionally combine with the carbon atom to which they are both attached to form a cycloalkyl group having from 3 to 6 carbon atoms;
- $R^3$ is H or —$C_1$-$C_6$ alkyl;
- $R^4$ is H, or —$C_1$-$C_6$ alkyl;
- $R^5$ is a phenyl group substituted with one or two groups independently selected from the group consisting of —$C_1$-$C_3$ alkyl, $C_3$-$C_6$ cycloalkyl, —$C_1$-$C_6$ alkyl$C_3$-$C_6$ cycloalkyl, —$C_1$-$C_3$ haloalkyl, —$OC_1$-$C_3$ alkyl, —$OC_1$-$C_3$ haloalkyl, —O-aryl, and halo;
- $R^6$ is H, —$C_1$-$C_3$ alkyl, —$C_1$-$C_3$ haloalkyl, —$OC_1$-$C_6$ alkyl, —$OC_1$-$C_3$ haloalkyl, or halo;
- $R^7$ is H, —$C_1$-$C_3$ alky, —$C_1$-$C_3$ haloalkyl, —$OC_1$-$C_3$ alkyl, —$C_1$-$C_3$ haloalkyl or halo;
- n=1-2;
- or a pharmaceutically acceptable salt thereof.

4. The compound according to claim 2 wherein,
- $R^1$ is a pyrimidinyl, pyridinyl, imidazolyl, or thiazolyl group optionally substituted with 1 or 2 groups independently selected from the group consisting of $C_1$-$C_3$ alkyl, $C_3$-$C_6$ cycloalkyl and halo;
- $R^2$ and $R^{2'}$ are at each occurrence independently H or $C_1$-$C_3$ alkyl; or one set of $R^2$ and $R^2$ optionally combine with the carbon atom to which they are both attached to form a cyclopropyl group;
- $R^3$ is H or —$C_1$-$C_6$ alkyl;
- $R^4$ is H;
- $R^5$ is a phenyl group substituted with one or two groups independently selected from the group consisting of —$C_1$-$C_3$ alkyl, —$C_1$-$C_3$ haloalkyl, —$OC_1$-$C_3$ alkyl,—$OC_1$-$C_3$ haloalkyl, and halo;
- $R^6$ is H, or —$C_1$-$C_3$ alkyl;
- $R^7$ is H, or —$C_1$-$C_3$ alkyl;
- n=1-2;
- or a pharmaceutically acceptable salt thereof.

5. The compound according to claim 2 wherein $R^1$ is pyridinyl or pyrimidinyl.

6. The compound according to claim 2 wherein $R^1$ is thiazolyl or imidazolyl.

7. The compound according to claim 2 wherein $R^1$ is pyridinyl or thiazolyl.

8. The compound of according to claim 2 wherein:
- $R^1$ is a pyridine, pyrimidine, imidazolyl, or thiazolyl group each optionally substituted with 1 or 2 groups independently selected from the group consisting of $C_1$-$C_6$ alkyl, $C_3$-$C_6$ cycloalkyl, halogen, $C_1$-$C_6$ haloalkyl, —$OC_1$-$C_6$ alkyl, —$OC_1$-$C_6$ haloalkyl, and —$C(O)C_1$-$C_6$ alkyl;
- $R^2$ and $R^{2'}$ are at each occurrence independently H or $C_1$-$C_6$ alkyl; or one set of $R^2$ and $R^2$ combine with the carbon atom to which they are both attached to form a $C_3$-$C_6$ cycloalkyl group;
- $R^3$ is H or —$C_1$-$C_6$ alkyl;
- $R^4$ is H, or —$C_1$-$C_6$ alkyl;
- $R^5$ is phenyl optionally substituted with one, two or three groups independently selected from the group consisting of —$C_1$-$C_6$ alkyl, —$C_0$-$C_6$ alkyl$C_3$-$C_6$ cycloalkyl, —$C_1$-$C_6$ haloalkyl, —$OC_1$-$C_6$ alkyl, —$OC_1$-$C_6$ haloalkyl, —O-aryl, and halo; wherein the cycloalkyl group is optionally substituted with —$C_1$-$C_6$ alkyl or —$C_1$-$C_6$ haloalkyl;
- n is 1 or 2; or a pharmaceutically acceptable salt thereof.

9. The compound according to claim 2 wherein $R^3$ and $R^4$ independently hydrogen or methyl.

10. A compound selected from the group consisting of:
- 6-[3-fluoro-4-(trifluoromethoxy)phenyl]-3-(pyrimidin-2-ylmethyl)-4H-1,3-benzoxazin-2-one;
- 6-[2-methoxy-4-(trifluoromethoxy)phenyl]-3-(pyrimidin-2-ylmethyl)-4H-1,3-benzoxazin-2-one;
- 6-[2-methyl-4-(trifluoromethoxy)phenyl]-3-(pyrimidin-2-ylmethyl)-4H-1,3-benzoxazin-2-one;
- 6-[2-fluoro-4-(trifluoromethoxy)phenyl]-3-(pyrimidin-2-ylmethyl)-4H-1,3-benzoxazin-2-one;
- 8-fluoro-3-(pyrimidin-2-ylmethyl)-6-[4-(trifluoromethoxy)phenyl]-4H-1,3-benzoxazin-2-one;
- 8-fluoro-6-[3-methyl-4-(trifluoromethoxy)phenyl]-3-(pyrimidin-2-ylmethyl)-4H-1,3-benzoxazin-2-one;
- 6-(3-chloro-4fluorophenyl)-3-(pyrimidin-2-ylmethyl)-4H-1,3-benzoxazin-2-one;

6-(4-chloro-3-fluorophenyl)-3-(pyrimidin-2-ylmethyl)-4H-1,3-benzoxazin-2-one;
6-[3-methyl-4-(trifluoromethoxy)phenyl]-3-(pyrimidin-2-ylmethyl)-4H-1,3-benzoxazin-2-one;
3-[(3-fluoropyridin-2-yl)methyl]-4-methyl-6-[4-(trifluoromethoxy)phenyl]-4H-1,3-benzoxazin-2-one;
4-methyl-6-(3-phenoxyphenyl)-3-(pyrimidin-2-ylmethyl)-4H-1,3-benzoxazin-2-one;
6-[2-fluoro-4-(trifluoromethyl)phenyl]-4-methyl-3-(pyrimidin-2-ylmethyl)-4H-1,3-benzoxazin-2-one;
6- [3-(difluoromethoxy)phenyl]-4-methyl -3-(pyrimidin-2-ylmethyl)-4H-1,3-benzoxazin-2-one;
4-methyl-3--(pyrimidin-2-ylmethyl)-6-[3-(trifluoromethoxy)phenyl]-4H1,3-benzoxazin-2-one;
1-[4-[4-methyl-2-oxo-3-(pyrimidin-2-ylmethyl)-4H-1,3-benzoxazin-6-yl]phenyl]cyclopropane-1-carbonitrile;
4-methyl-3-(pyrimidin-2-ylmethyl)-6-[4-(trifluoromethyl)phenyl]-4H-1 ,3-benzoxazin-2-one;
4-methyl-3-(pyrimidin-2-ylmethyl)-6-[4-(trifluoromethoxy)phenyl]-4H -1,3-benzoxazin-2-one;
3-(pyrimidin-2-ylmethyl)-6-[4(trifluoromethyl)phenyl]-4H-1,3-benzoxazin-2-one;
3-(pyrimidin-2-ylmethyl)-6-[4-(trifluoromethoxy)phenyl]-4H-1,3-benzoxazin-2-one;
3-(pyridin-4-ylmethyl)-6-[4-(trifluoromethyl)phenyl]-4H-1,3-benzoxazin-2-one; or a pharmaceutically acceptable salt thereof.

11. The compound according to claim 2 wherein $R^6$ and $R^7$ are independently selected from the group consisting of hydrogen, methyl, and flouro.

12. The compound according to claim 2 wherein:
$R^1$ is a 5-membered heterocyclic group;
one set of $R^2$ and $R^{2'}$ combine to form a cyclopropyl group;
$R^3$ and $R^4$ are each H;
$R^5$ is a phenyl group optionally substituted with one or two groups independently selected from $C_1$-$C_3$alkyl,—$C_1$-$C_3$ haloalkyl, —$OC_1$-$C_3$ alkyl, —$OC_1$-$C_3$ haloalkyl, and halo;
$R^6$ and $R^7$ are both H; and
n is 3; or a pharmaceutically acceptable salt thereof.

13. The compound according to claim 2 wherein $R^1$ is selected from the group consisting of: imidazolyl and thiazolyl, optionally substituted with a $C_1$-$C_6$ alkyl group.

14. The compound according to claim 13 wherein the optional $C_1$-$C_6$ alkyl group substituent is methyl.

15. A compound selected from the group consisting of:
3-[[1-[(2-methylimidazol-1-yl)methyl]cyclopropyl]methyl]-6-[4-(trifluoromethoxy)phenyl]-4H-1,3-benzoxazin-2-one;
3-[[1[(2-methylimidazol-1-yl)methyl]cyclopropyl]methyl]-6-[4-(trifluoromethyl)phenyl]-4H-1,3-benzoxazin-2-one;
6-[2-fluoro-4-(trifluoromethoxy)phenyl]-3-[[1-[(2-methylimidazol-1-yl)methyl]cyclopropyl]methyl]-4H-1,3-benzoxazin-2-one;
3-[[1-[(2-methylimidazol-1-yl)methyl]cyclopropyl]methyl]-6-[3-methyl-4-(trifluoromethoxy)phenyl]-4H-1,3-benzoxazin-2-one;
6-[2-methoxy-4-(trifluoromethoxy)phenyl]-3-[[1-[(2-methylimidazol-1-yl)methyl]cyclopropyl]methyl]-4H-1,3-benzoxazin-2-one; or a pharmaceutically acceptable salt thereof.

16. The compound according to claim 2 wherein:
$R^1$ is a 5-membered heterocyclic group;
one set of $R^2$ and $R^{2'}$ combine to form a cyclopropyl group;
$R^3$ and $R^4$ are each H;
$R^5$ is a phenyl group optionally substituted with one or two groups independently selected from $C_1$-$C_3$ alkyl, —$C_1$-$C_3$ haloalkyl, —$OC_1$-$C_3$ alkyl,—$OC_1$-$C_3$ haloalkyl, and halo;
$R^6$ and $R^7$ are both H; and
n is 1; or a pharmaceutically acceptable salt thereof.

17. The compound according to claim 2 selected from the group consisting of:
6-[2-methoxy-4-(trifluoromethoxy)phenyl]-3-(1-pyridin-2-ylcyclopropyl)-4H-1,3-benzoxazin-2-one;
6- [3-methyl-4-(trifluoromethoxy)phenyl]-3-(1-pyridin-2-ylcyclopropyl)-4H-1,3-benzoxazin-2-one;
6-[2-fluoro-4-(trifluoromethoxy)phenyl]-3-(1-pyridin-2-ylcyclopropyl)-4H-1,3-benzoxazin-2-one;
3-(1-pyridin-2-ylcyclopropyl)-6-[4-(trifluoromethyl)phenyl]-4H-1,3-benzoxazin-2-one;
3-(1-pyridin-2-ylcyclopropyl)-6-[4-trifluoromethoxy)phenyl]-4H-1,3-benzoxazin-2-one;
or a pharmaceutically acceptable salt thereof.

18. The compound according to claim 2 wherein:
$R^1$ is a 6-membered heterocyclic
$R^2$ and $R^{2'}$ are both H;
$R^3$ is H or $C_1$-$C_6$ alkyl;
$R^4$ is H or $C_1$-$C_6$ alkyl;
$R^5$ is a phenyl group optionally substituted with one or two groups independently selected from $C_1$-$C_3$alkyl, —$C_1$-$C_3$haloalkyl, —$OC_1$-$C_3$ alkyl, —$OC_1$-$C_3$ haloalkyl, and halo
$R^6$ and $R^7$ are both H; and
n is 1; or a pharmaceutically acceptable salt thereof.

19. The compound according to claim 2 wherein:
$R^1$ is a pyrimidinyl optionally substituted with $C_1$-$C_6$ alkyl;
$R^{2a}$ and $R^{2b}$ are both H;
$R^3$ is $CH_3$;
$R^4$ is H;
$R^5$ is a phenyl group optionally substituted with one or two groups independently selected from —$OCF_3$, halogen, $CH_3$, or —$OCH_3$;
$R^6$ and $R^7$ are both H; and
n is 1; or a pharmaceutically acceptable salt thereof.

20. The compound according to claim 2 selected from the group consisting of:
6[2-fluoro-4-(trifluoromethoxy)phenyl]-4-methyl-3-(pyrimidin-2-ylmethyl)-4H-1,3-benzoxazin-2-one;
4-methyl-6-[2-methyl-4-(trifluoromethoxy)phenyl]-3-(pyrimidin-2-ylmethyl)-4H-1,3-benzoxazin-2-one;
4-methyl-6-[3-methyl-4-(trifluoromethoxy)phenyl]-3-(pyrimidin-2-ylmethyl)-4H-1,3-benzoxazin-2-one;
6-(4-chloro-3-fluorophenyl)-4-methyl-3-(pyrimidin-2-ylmethyl)-4H-1,3-benzoxazin-2-one;
6-(3,4-dichlorophenyl)-4-methyl-3-(pyrimidin-2-ylmethyl)-4H-1,3-benzoxazin-2-one;
6-[2-methoxy-4-(trifluoromethoxy)phenyl]-4-methyl-3-(pyrimidin-2-ylmethyl)-4H-1,3-benzoxazin-2-one;
6-[2-fluoro-4-(trifluoromethyl)phenyl]-4-methyl-3-(pyrimidin-2-ylmethyl)-4H-1,3-benzoxazin-2-one;
6-[3-(difluoromethoxy)phenyl]-4-methyl-3-(pyrimidin-2-ylmethyl)4H1,3-benzoxazin-2-one;
4-methyl-3-(pyrimidin-2-ylmethyl)-6-[3-(trifluoromethoxy)phenyl]4H-1,3-benzoxazin-2-one;
1-[4-[4-methyl-2-oxo-3-(pyrimidin-2-ylmethyl)-4H-1,3-benzoxazin-6-yl]phenyl]cyclopropane-1-carbonitrile;
4-methyl-3-(pyrimidin-2-ymethyl)-6-[4-(trifluoromethyl)phenyl]-4H-1,3-berizoxazin-2-one;
4-methyl-3-(pyrimidin-2-ylmethyl)-6-[4-(trifluoromethoxy)phenyl]-4H-1,3-benzoxazin-2-one; or a pharmaceutically acceptable salt thereof.

21. The compound according to claim 2 wherein
R¹ is a pyrimidinyl optionally substituted with $C_1$-$C_6$ alkyl;
R²ᵃ and R²ᵇ are both H;
R³ is H;
R⁴ is H;
R⁵ is a phenyl group optionally substituted with one or two groups independently selected from —OCF₃, halogen, CH₃, or —OCH₃;
R⁶ and R⁷ are both H; and
n is 1; or a pharmaceutically acceptable salt thereof.

22. A compound according to claim 2 selected from the group consisting of:
3-[(5-methylpyrimidin-2-yl)methyl]-6-[2-methyl-4-(trifluoromethyl)phenyl]4H-1,3-benzoxazin-2-one;
6-[2-methoxy-4-(trifluoromethyl)phenyl]-3-[(5-methylpyrimidin-2-yl)methyl]-4H-1,3benzoxazin-2-one;
6-[2-fluoro-4-(trifluoromethyl)phenyl]-3-[(5-methylpyrimidin-2-yl)methyl]-4H-1,3-benzoxazin-2-one;
6-[2-ethoxy-4-(trifluoromethoxy)phenyl]-3-(pyrimidin-2-ylmethyl)-4H-1,3-benzoxazin-2-one;
6[2-propan-2-yloxy-4-(trifluoromethoxy)phenyl]-3-(pyrimidin-2-ylmethyl)-4H-1,3-benzoxazin-2-one;
3-(pyrimidin-2-ylmethyl)-6-[4-[1-(trifluoromethyl)cyclopropyl]phenyl]-4H-1,3-benzoxazin-2-one;
6[2-methyl-4-(trifluoromethyl)phenyl]-3-(pyrimidin-2-ylmethyl)-4H-1,3-benzoxazin-2-one;
6-[2-fluoro-4-(trifluoromethyl)phenyl]-3-(pyrimidin-2-ylmethyl)-4H-1,3-benzoxazin-2-one;
6[2-ethoxy-4-(trifluoromethyl)phenyl]-3-(pyrimidin-2-ylmethyl)-4H-1,3-benzoxazin-2-one;
6-[2-methoxy-4-(trifluoromethyl)phenyl]-3-(pyrimdin-2-ylmethyl)-4H-1,3-benzoxazin-2-one;
3-[(4-methylpyrimidin-2-yl)methyl]-6-[2-methyl-4-(trifluoromethoxy)phenyl]-4H-1,3-benzoxazin-2-one;
6-[2-fluoro-4-(trifluoromethoxy)phenyl]-3-[(4-methylpyrimidin-2-yl)methyl]-4H-1,3-benzoxazin-2-one;
6-[2-methoxy-4-(trifluoromethoxy)phenyl]-3-[(4-methylpyrimidin-2-yl)methyl]-4H-1,3-benzoxazin-2-one;
3-[(4-methylpyrimidin-2-methyl)-6-[4-(trifluoromethyl)phenyl]4H-1,3-benzoxazin-2-one;
3-[(4-methylpyrimidin-2-yl)methyl]-6-[4-(trifluoromethyl)phenyl]-4H-1,3-benzoxazin-2-one;
6-[2-propoxy-4-(trifluoromethoxy)phenyl]-3-(pyrimidin-2-ylmethyl)-4H-1,3-benzoxazin-2-one;
6[2-propoxy-4-(trifluoromethyl)phenyl]-3-(pyrimidin-2-ylmethyl)-4H-1,3-benzoxazin-2-one; and
6-(2,2-difluoro-1,3-benzodioxol-5-yl)-3-(pyrimidin-2-ylmethyl)-4H-1,3-benzoxazin-2-one;
or a pharmaceutically acceptable salt thereof.

23. The compound according to claim 2 wherein:
R¹ is thiazolyl optionally substituted with $C_1$-$C_6$ alkyl;
R² and R²' are both H;
R³ is H;
R⁴ is H;
R⁵ is a phenyl group optionally substituted with one or two groups independently selected from CH₃, —OCF₃, halogen, or —OCH₃;
R⁶ and R⁷ are both H; and
n is 1; or a pharmaceutically acceptable salt thereof.

24. The compound according to claim 2 selected from the group consisting of:
6-(4-chloro-3-fluorophenyl)-3-[(4-methyl-1,3-thiazol-2-yl)methyl]-4H-1,3-benzoxazin-2-one;
6-[2-methoxy-4-(trifluoromethoxy)phenyl]-3-[(4-methyl-1,3-thiazol-2-yl)methyl]-4H-1,3-benzoxazin-2-one;
6-[2-chloro-4-(trifluoromethoxy)phenyl]-3-[(4-methyl-1,3-thiazol-2-yl)methyl]-4H-1,3-benzoxazin-2-one;
6-(3,4-dichlorophenyl)-3-[(4-methyl-1,3-thiazol-2-yl)methyl]-4H-1,3-benzoxazin-2-one;
6-[2-fluoro-4-(trifluoromethoxy)phenyl]-3-[(4-methyl-1,3-thiazol-2-yl)methyl]-4H-1,3-benzoxazin-2-one;
3-[(4-methyl-1,3-thiazol-2-yl)methyl]-6-[3-methyl-4-(trifluoromethoxy)phenyl]-4H-1,3-benzoxazin-2-one;
6-[3-fluoro-4-(trifluoromethoxy)phenyl]-3-[(4-methyl-1,3-thiazol-2-yl)methyl]-4H-1,3-benzoxazin-2-one; and
3-[(4-methyl-1,3-thiazol-2-yl)methyl]-6-[4-(trifluoromethoxy)phenyl]-4H-1,3-benzoxazin-2-one; or a pharmaceutically acceptable salt thereof.

25. The compound according to claim 2 wherein:
R¹ is pyridinyl optionally substituted with $C_1$-$C_6$ alkyl;
R² and R²' are both H;
R³ is H;
R⁴ is H;
R⁵ is a phenyl group optionally substituted with one or two groups independently selected from CH₃, —OCF₃, halogen, or —OCH₃;
R⁶ and R⁷ are both H; and
n is 1; or a pharmaceutically acceptable salt thereof.

26. The compound according to claim 2 selected from the group consisting of
6-[2-fluoro-4-(trifluoromethoxy)phenyl]-3-[(6-methylpyridin-2-yl)methyl]-4H-1,3-benzoxazin-2one;
6-[2-methoxy-4-(trifluoromethoxy)phenyl]-3[(6-methylpyridin-2-yl)methyl]-4H-1,3-benzoxazin-2-one;
6-[2-fluoro-4-(trifluoromethyl)phenyl]-3-[(6-methylpridin-2-yl)methyl]-4H-1,3-benzoxazin-2-one;
6-[2-methoxy-4-(trifluoromethyl)phenyl]-3-[(6-methylpyridin-2-yl)methyl]-4H-1,3-benzoxazin-2-one;
3-(pyridin-2-ylmethyl)-6-[4-(trifluoromethyl)phenyl]-4H-1,3-benzoxazin-2-one;
6[3-methyl-4-(trifluoromethoxy)phenyl]-3-(pyridin-2-ylmethyl)-4H-1,3-benzoxazin-2-one;
6-[2-methyl-4-(trifluoromethoxy)phenyl]-3-(pyridin-2-ylmethyl)-4H-1,3-benzoxazin-2-one;
6[2-methoxy-4-(trifluoromethoxy)phenyl]-3-(pyridin-2-ylmethyl)-4-H-1,3-benzoxazin-2-one;
6[2-fluoro-4-(trifluoramethoxy)phenyl]-3-(pyridin-2-ylmethyl)-4H-1,3-benzoxazin-2-one;
3-(pyridin-2-ylmethyl)-6-[4-(trifluoromethoxy)phenyl]-4H-1,3-benzoxazin-2-one;
6-[2-methoxy-4-(trifluoromethoxy)phenyl]-3-(1-pyridin-2-ylcyclopropyl)-4H-1,3-benzoxazin)-2-one;
6[3-methyl-4-(trifluoromethoxy)phenyl]-3-(1-pyridin-2-ylcyclopropyl)-4H-1,3-benzoxazin-2-one;
6-[2-fluoro4-(trifluoromethoxy)phenyl]-3-(1-pyridin-2-ylcyclopropyl)-4H-1,3-benzoxazin-2-one;
3-(1-pyridin-2-ylcyclopropyl)-6-[4-(trifluoromethyl)phenyl]-4H-1,3-benzoxazin-2-one;
3-(1-pyridin-2-ylcyclopropyl)-6-[4-(trifluoromethoxy)phenyl]-4H-1,3-benzoxazin-2-one;
3-(pyridin-4-ylmethyl)-6-[4-(trifluoromethyl)phenyl]-4H-1,3 benzoxazin-2-one; and
3-(pyridine-4-ylmethyl)-6-[4-(trifluoromethoxy)phenyl]-4H-1,3-benzoxazin-2-one;
or a pharmaceutically acceptable salt thereof.

27. A compound represented by the structure:

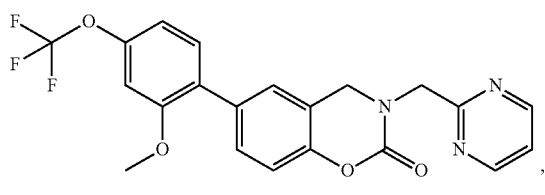 [SMILES: COc1cc(OC(F)(F)F)ccc1-c1ccc2c(c1)CN(Cc1ncccn1)C(=O)O2]

or a pharmaceutically acceptable salt thereof.

28. A compound represented by the structure:

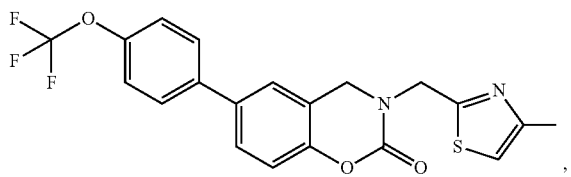 [SMILES: Cc1csc(CN2Cc3cc(-c4ccc(OC(F)(F)F)cc4)ccc3OC2=O)n1]

or a pharmaceutically acceptable salt thereof.

29. A compound represented by the structure:

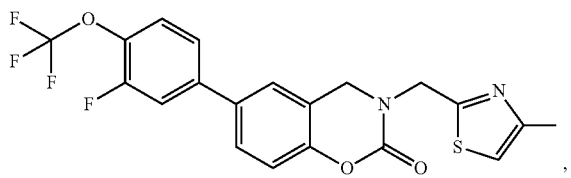 [SMILES: Cc1csc(CN2Cc3cc(-c4ccc(OC(F)(F)F)c(F)c4)ccc3OC2=O)n1]

or a pharmaceutically acceptable salt thereof.

30. A compound represented by the structure:

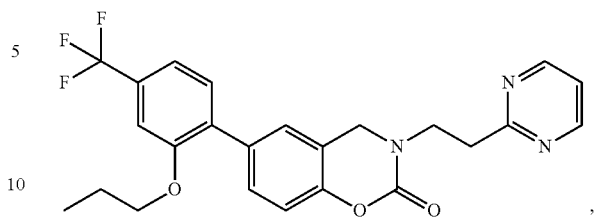

or a pharmaceutically acceptable salt thereof.

31. A pharmaceutical composition comprising a therapeutically effective amount of the compound of any one of claim 2, and a pharmaceutically acceptable excipient.

32. A method of treating cardiovascular disease selected from atrial arrhythmias, ventricular arrhythmias, heart failure (including congestive heart failure, diastolic heart failure, systolic heart failure, acute heart failure), Prinzmetal's (variant) angina, stable angina, unstable angina, exercise induced angina, congestive heart disease, ischemia, recurrent ischemia, reperfusion injury, myocardial infarction, acute coronary syndrome, peripheral arterial disease, pulmonary hypertension and intermittent claudication.

33. The method according to claim 32, wherein the disease is diabetes or diabetic peripheral neuropathy.

34. The method according to claim 32, wherein the disease state results in one or more of neuropathic pain, epilepsy, migraine, seizures or paralysis.

35. The method according to claim 32 wherein the disease state is Long QT syndrome.

36. The method of claim 35 wherein the Long QT syndrome is LQT1, LQT2, or LQT3.

37. The method according to claim 32 wherein the disease state is hypertrophic cardiomyopathy.

38. The method according to claim 32 wherein the disease state is ventricular tachycardia or ventricular fibrillation.

* * * * *